United States Patent
Kim et al.

(10) Patent No.: US 11,667,626 B2
(45) Date of Patent: Jun. 6, 2023

(54) COMPOUND AND ORGANIC LIGHT-EMITTING DEVICE COMPRISING SAME

(71) Applicant: LG CHEM, LTD., Seoul (KR)

(72) Inventors: Minjun Kim, Daejeon (KR);
Kongkyeom Kim, Daejeon (KR);
Hyoung Seok Kim, Daejeon (KR);
Min Woo Lee, Daejeon (KR)

(73) Assignee: LG CHEM, LTD., Seoul (KR)

(*) Notice: Subject to any disclaimer, the term of this patent is extended or adjusted under 35 U.S.C. 154(b) by 576 days.

(21) Appl. No.: 16/630,797

(22) PCT Filed: Nov. 19, 2018

(86) PCT No.: PCT/KR2018/014219
§ 371 (c)(1),
(2) Date: Jan. 13, 2020

(87) PCT Pub. No.: WO2019/098796
PCT Pub. Date: May 23, 2019

(65) Prior Publication Data
US 2020/0165234 A1    May 28, 2020

(30) Foreign Application Priority Data
Nov. 17, 2017   (KR) .................. 10-2017-0154169

(51) Int. Cl.
*C07D 409/14*       (2006.01)
*C07D 403/14*       (2006.01)

(52) U.S. Cl.
CPC .......... *C07D 409/14* (2013.01); *C07D 403/14* (2013.01); *H10K 85/654* (2023.02); *H10K 85/6572* (2023.02); *H10K 85/6576* (2023.02); *H10K 50/15* (2023.02); *H10K 50/16* (2023.02); *H10K 50/171* (2023.02)

(58) Field of Classification Search
CPC .. C07D 409/14; C07D 403/14; C07D 209/56; C07D 251/24; C07D 333/76; H01L 51/0067; H01L 51/0072; H01L 51/0074; H01L 51/5056; H01L 51/5072; H01L 51/5092; H01L 51/0085; H01L 51/5016; H01L 51/0052; H01L 51/0058; H01L 51/5048; H01L 51/5088; C09K 11/06; C09K 2211/1029; C09K 2211/1059; H10K 85/654; H10K 85/6572; H10K 85/6576; H10K 50/15; H10K 50/16; H10K 50/171; H10K 50/11; H10K 85/342; H10K 2101/10; H10K 85/615; H10K 85/626; H10K 50/14; H10K 50/17

USPC ......................................................... 428/690
See application file for complete search history.

(56) References Cited

U.S. PATENT DOCUMENTS

| | | | |
|---|---|---|---|
| 2004/0251816 A1 | 12/2004 | Leo et al. | |
| 2017/0005276 A1* | 1/2017 | Kim ..................... | C07D 487/04 |
| 2018/0148641 A1 | 5/2018 | Cha et al. | |
| 2018/0315930 A1 | 11/2018 | Han et al. | |
| 2019/0131542 A1 | 5/2019 | Kim et al. | |
| 2019/0288222 A1 | 9/2019 | Moon et al. | |
| 2020/0136059 A1* | 4/2020 | Hong ..................... | C09K 11/06 |

FOREIGN PATENT DOCUMENTS

| | | | |
|---|---|---|---|
| CN | 104812750 | 7/2015 | |
| CN | 106892901 | 6/2017 | |
| CN | 111052428 | 4/2020 | |
| KR | 10-20110107681 | 10/2011 | |
| KR | 10-20140046541 | 4/2014 | |
| KR | 10-20170049441 | 5/2017 | |
| KR | 10-20170057849 | 5/2017 | |
| WO | 2003012890 | 2/2003 | |
| WO | 2014-054912 | 4/2014 | |
| WO | WO-2015142040 A1 * | 9/2015 | ........... C07D 401/04 |
| WO | 2017183859 | 10/2017 | |
| WO | 2018105888 | 6/2018 | |
| WO | WO-2021261977 A1 * | 12/2021 | |

OTHER PUBLICATIONS

CAS reg. No. 2330849-32-4, Jun. 12, 2019. (Year: 2019).*
International Search Report and the Written Opinion of PCT/KR2018/014219, dated Feb. 22, 2019.

* cited by examiner

*Primary Examiner* — Douglas J McGinty
(74) *Attorney, Agent, or Firm* — Dentons US LLP

(57) ABSTRACT

Provided is a compound of Formula 1:

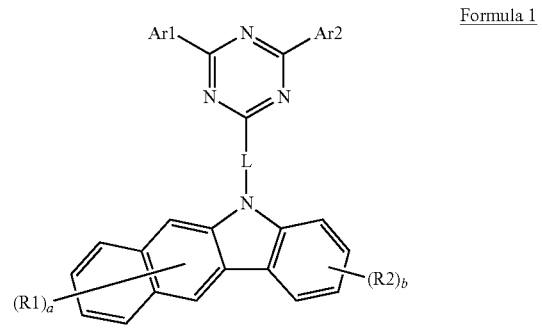

Formula 1 and an organic light emitting device including the same.

12 Claims, 4 Drawing Sheets

[Figure 1]
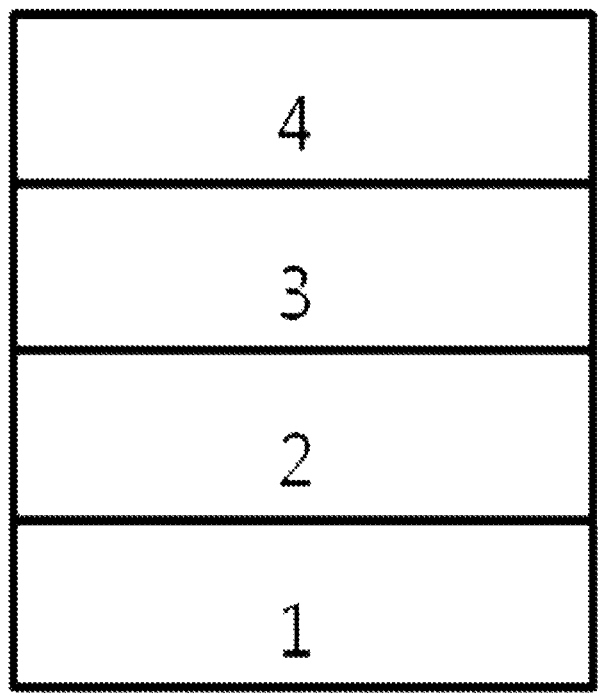

[Figure 2]
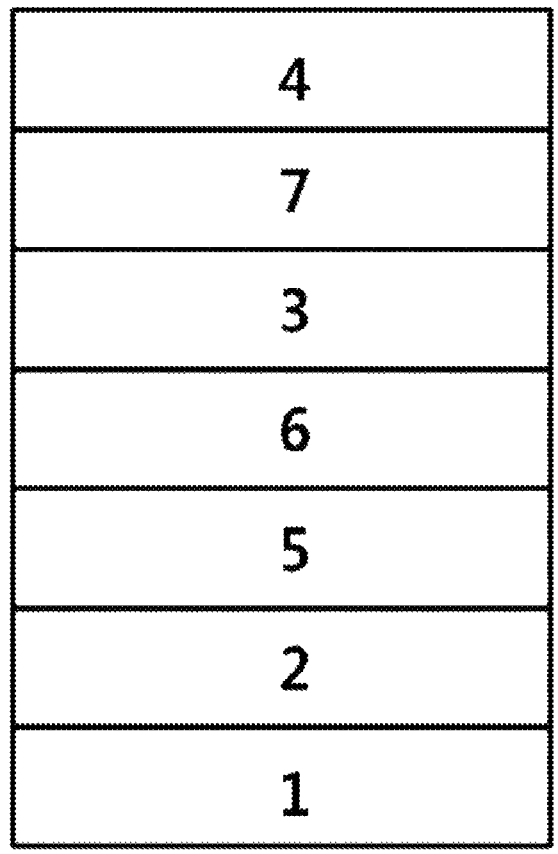

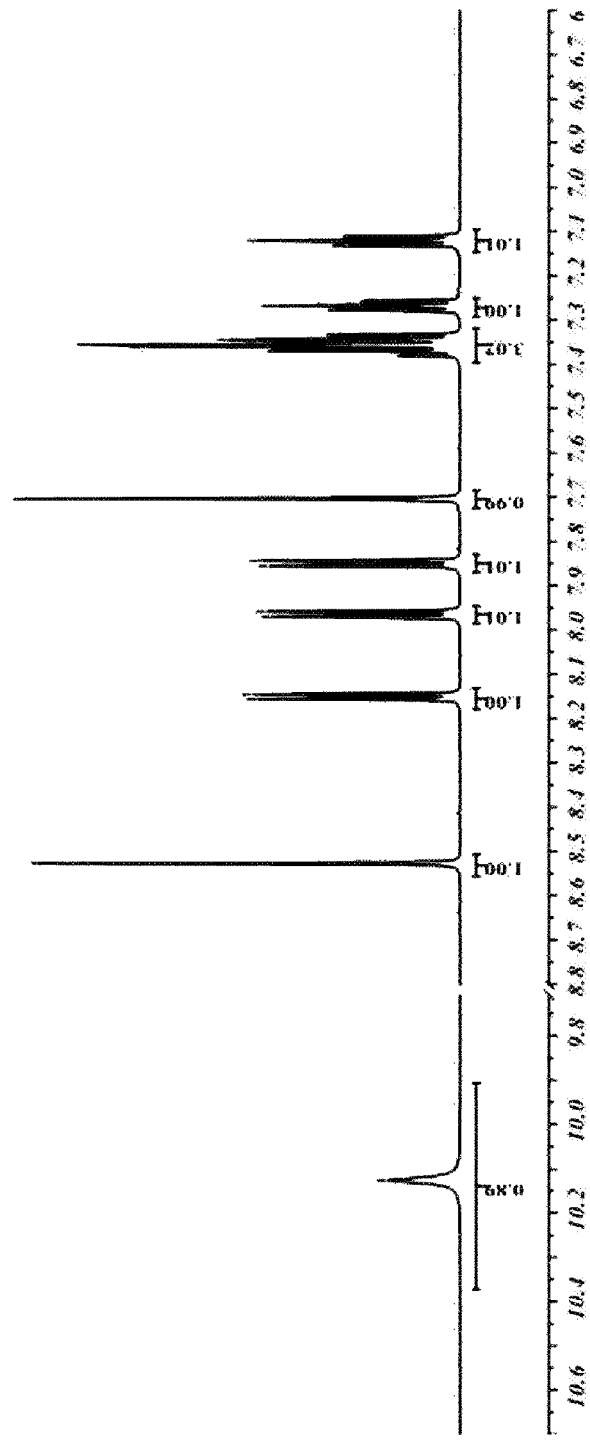
[Figure 3]

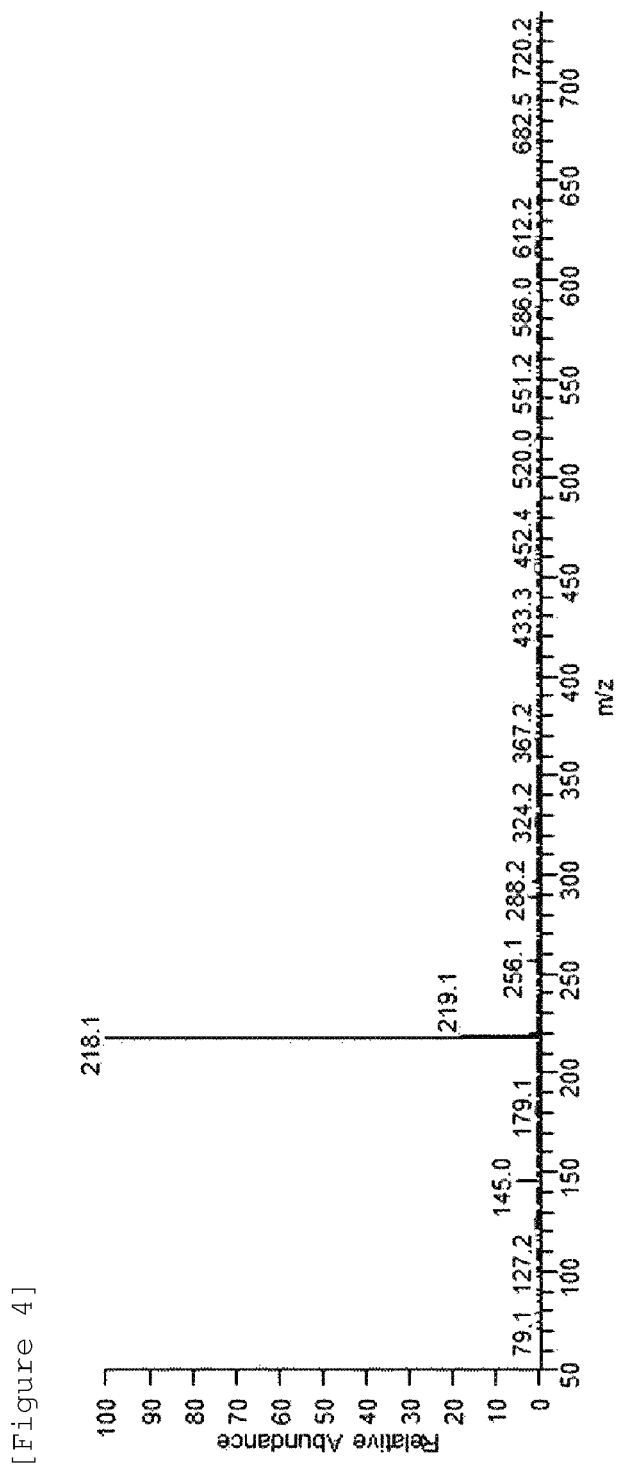
[Figure 4]

COMPOUND AND ORGANIC LIGHT-EMITTING DEVICE COMPRISING SAME

CROSS-REFERENCE TO RELATED APPLICATIONS

This application is a National Stage Application of International Application No. PCT/KR2018/014219 filed on Nov. 19, 2018, which claims priority to and the benefit of Korean Patent Application No. 10-2017-0154169 filed in the Korean Intellectual Property Office on Nov. 17, 2017, the entire contents of which are incorporated herein by reference.

TECHNICAL FIELD

The present application relates to a compound and an organic light emitting device including the same.

BACKGROUND

In general, an organic light emitting phenomenon refers to a phenomenon in which electric energy is converted into light energy by using an organic material. An organic light emitting device using the organic light emitting phenomenon usually has a structure including a first electrode, a second electrode, and an organic material layer interposed therebetween. Here, the organic material layer has in many cases a multi-layered structure composed of different materials in order to improve the efficiency and stability of the organic light emitting device, and for example, can be composed of a hole injection layer, a hole transport layer, a light emitting layer, an electron transport layer, an electron injection layer, and the like. In the structure of the organic light emitting device, if a voltage is applied between the two electrodes, holes are injected from the first electrode into the organic material layer and electrons are injected from the second electrode into the organic material layer, and when the injected holes and electrons meet each other, an exciton is formed, and light is emitted when the exciton falls down again to a ground state.

There is a continuous need for developing a new material for the aforementioned organic light emitting device.

Prior Art document—Korean Patent Application Laid-Open No. 10-2011-0107681

DETAILED DESCRIPTION OF INVENTION

Technical Problem

The present application provides a compound and an organic light emitting device including the same.

Technical Solution

The present application provides a compound of Formula 1:

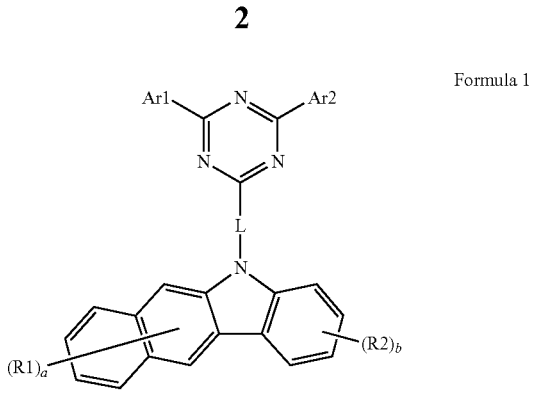

Formula 1

In Formula 1:
L is a direct bond or a substituted or unsubstituted arylene group; and
one of Ar1 and Ar2 is a substituted or unsubstituted aryl group having 6 to 15 carbon atoms, and the other is a substituent of Formula 2:

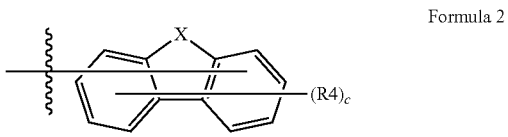

Formula 2 wherein in Formulae 1 and 2:
X is S or NR3;
R1 to R4 are each independently hydrogen, deuterium, a halogen group, a substituted or unsubstituted silyl group, a substituted or unsubstituted alkyl group, a substituted or unsubstituted amine group, a substituted or unsubstituted arylamine group, a substituted or unsubstituted alkylamine group, a substituted or unsubstituted aryl group, or a substituted or unsubstituted heterocyclic group;
a is an integer from 0 to 6;
b is an integer from 0 to 4;
c is an integer from 0 to 7;
when a to c are each 2 or more, two or more substituents in the parenthesis are the same as or different from each other; and
when c is 2 or more, adjacent R4's can be bonded to each other to form a ring.

Further, the present application provides an organic light emitting device including: a first electrode; a second electrode provided to face the first electrode; and an organic material layer having one or more layers provided between the first electrode and the second electrode, in which one or more layers of the organic material layer include the above-described compound.

Advantageous Effects

An organic light emitting device using the compound according to an exemplary embodiment of the present application can have a low driving voltage, high light emitting efficiency and/or a long service life.

BRIEF DESCRIPTION OF DRAWINGS

FIG. 1 illustrates an example of an organic light emitting device in which a substrate 1, a first electrode 2, a light emitting layer 3, and a second electrode 4 are sequentially stacked.

FIG. 2 illustrates an example of an organic light emitting device in which the substrate 1, the first electrode 2, a hole injection layer 5, a hole transport layer 6, the light emitting layer 3, an electron transport layer 7, and the second electrode 4 are sequentially stacked.

FIGS. 3 and 4 illustrate 1H-NMR and mass analysis results for confirming Formula a.

BEST MODE

Hereinafter, the present specification will be described in more detail.

The present specification provides the compound of Formula 1.

According to an exemplary embodiment of the present application, the compound of Formula 1 can adjust the triplet energy by having a core structure as described above, and can exhibit long service life and high efficiency characteristics.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of hydrogen, a halogen group, a nitrile group, a nitro group, a hydroxyl group, an alkyl group, a cycloalkyl group, an alkenyl group, an amine group, an aryl group, and a heterocyclic group, being substituted with a substituent to which two or more substituents among the exemplified substituents are linked, or having no substituent. For example, "the substituent to which two or more substituents are linked" can be a biphenyl group. That is, the biphenyl group can also be an aryl group, and can be interpreted as a substituent to which two phenyl groups are linked.

In the present specification, examples of a halogen group include fluorine, chlorine, bromine or iodine.

In the present specification, the number of carbon atoms of an ester group is not particularly limited, but is preferably 1 to 50. Specifically, the ester group can be a compound having the following structural formulae, but is not limited thereto:

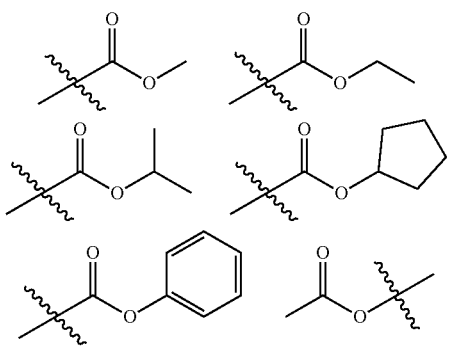

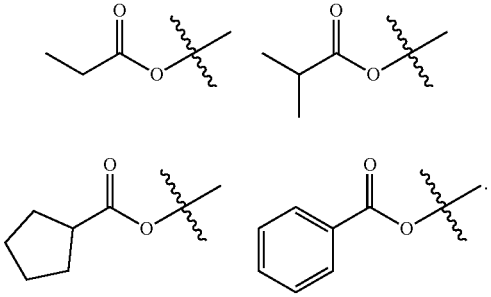

In the present specification, the alkyl group can be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methyl-pentyl, 2-methylpentyl, 4-methyl-2-pentyl, 3,3-dimethyl-butyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present specification, the cycloalkyl group is not particularly limited, but the number of carbon atoms thereof is preferably 3 to 60 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkenyl group can be straight-chained or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, when the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group can be substituted, and adjacent substituents can be bonded to each other to form a ring.

When the fluorenyl group is substituted, the substituent can be

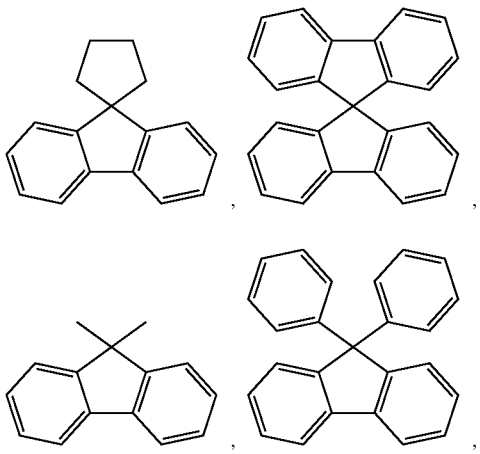

and the like, but is not limited thereto.

In the present specification, a heterocyclic group includes one or more atoms other than carbon, that is, one or more heteroatoms, and specifically, the heteroatom can include one or more atoms selected from the group consisting of O, N, Se, S, and the like. The number of carbon atoms of the heterocyclic group is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the above-described description on the aryl group can be applied to an aryl group in an aryloxy group, an arylthioxy group, an arylsulfoxy group, an arylphosphine group, an aralkyl group, an aralkylamine group, an aralkenyl group, and an arylamine group.

In the present specification, the above-described description on the alkyl group can be applied to an alkyl group in an alkylthioxy group, an alkylsulfoxy group, an aralkyl group, an aralkylamine group, and an alkylamine group.

In the present specification, the "adjacent" group can mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring can be interpreted as groups which are "adjacent" to each other.

In the present specification, the case where adjacent groups are bonded to each other to form a ring means that adjacent groups are bonded to each other to form a 5-membered to 8-membered hydrocarbon ring or a 5-membered to 8-membered hetero ring as described above, and the ring can be monocyclic or polycyclic, can be an aliphatic ring, an aromatic ring, or a fused form thereof, and is not limited thereto.

According to an exemplary embodiment of the present application, L is a direct bond, or a substituted or unsubstituted arylene group having 6 to 30 carbon atoms.

According to an exemplary embodiment of the present application, L is a direct bond, or a substituted or unsubstituted arylene group having 6 to 15 carbon atoms.

According to an exemplary embodiment of the present application, L is a phenylene group, or a naphthylene group.

According to an exemplary embodiment of the present application, one of Ar1 and Ar2 is a substituted or unsubstituted aryl group having 6 to 15 carbon atoms, and the other is a group of Formula 2.

According to an exemplary embodiment of the present application, R1 to R4 are each independently hydrogen, deuterium, a substituted or unsubstituted alkyl group, a substituted or unsubstituted aryl group, or a substituted or unsubstituted heterocyclic group.

According to an exemplary embodiment of the present application, R1 to R4 are each independently hydrogen, deuterium, a substituted or unsubstituted alkyl group having 1 to 30 carbon atoms, a substituted or unsubstituted aryl group having 6 to 30 carbon atoms, or a substituted or unsubstituted heterocyclic group having 2 to 30 carbon atoms.

According to an exemplary embodiment of the present application, R1 to R4 are each independently hydrogen, deuterium, a substituted or unsubstituted aryl group having 6 to 30 carbon atoms, or a substituted or unsubstituted heterocyclic group having 2 to 30 carbon atoms.

According to an exemplary embodiment of the present application, R1 and R2 are hydrogen.

According to an exemplary embodiment of the present application, R3 is a substituted or unsubstituted aryl group.

According to an exemplary embodiment of the present application, R3 is a substituted or unsubstituted aryl group having 6 to 30 carbon atoms.

According to an exemplary embodiment of the present application, R3 is a substituted or unsubstituted aryl group having 6 to 10 carbon atoms.

According to an exemplary embodiment of the present application, R3 is a substituted or unsubstituted phenyl group.

According to an exemplary embodiment of the present application, R4 is hydrogen.

According to an exemplary embodiment of the present application, c is 2 or more, and adjacent R4's are bonded to each other to form a ring.

According to an exemplary embodiment of the present application, a compound of Formula 1 is selected from among the following compounds:
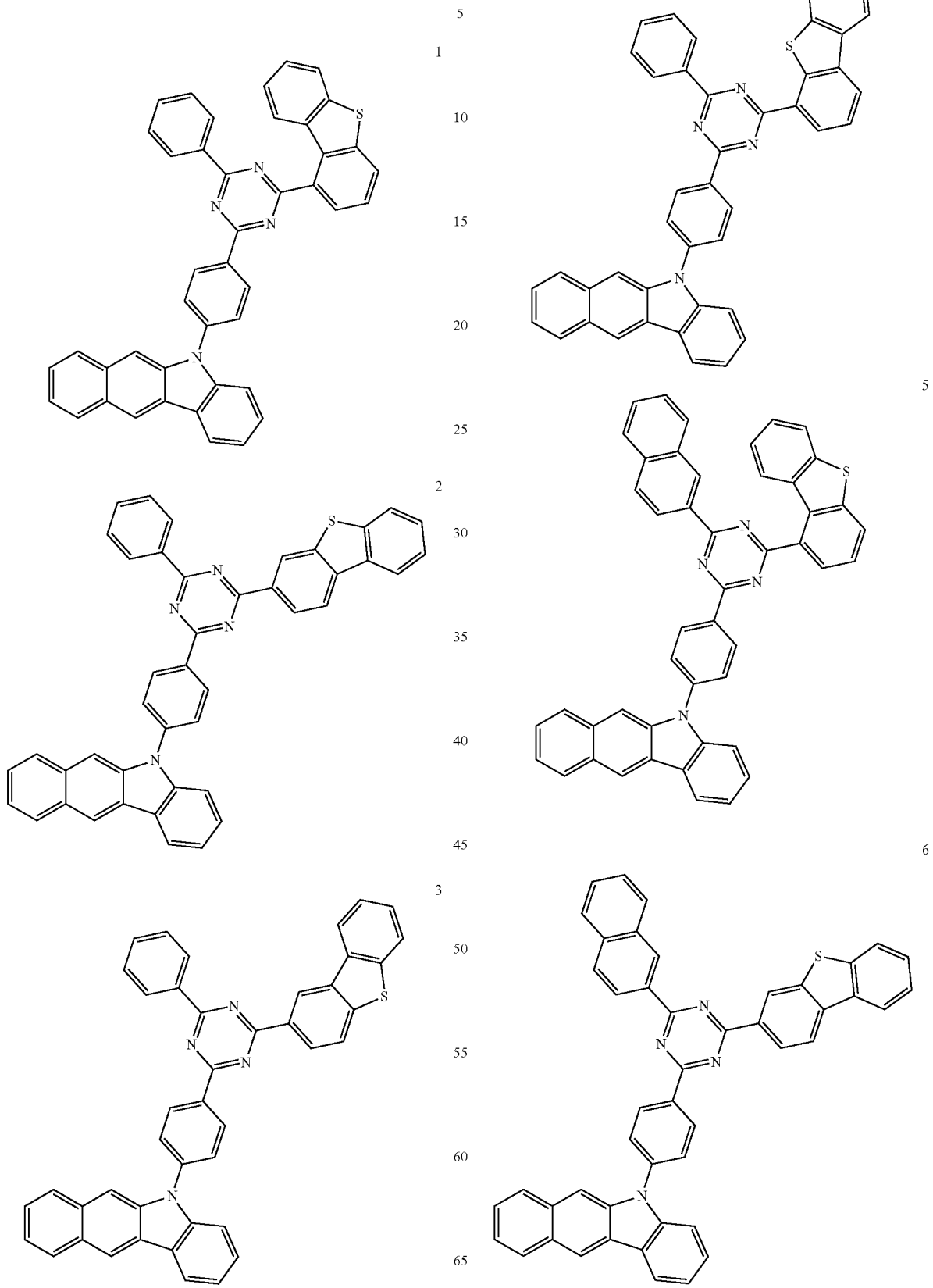

7
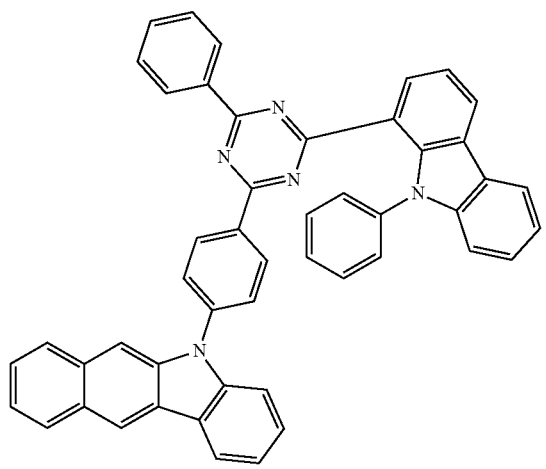
8
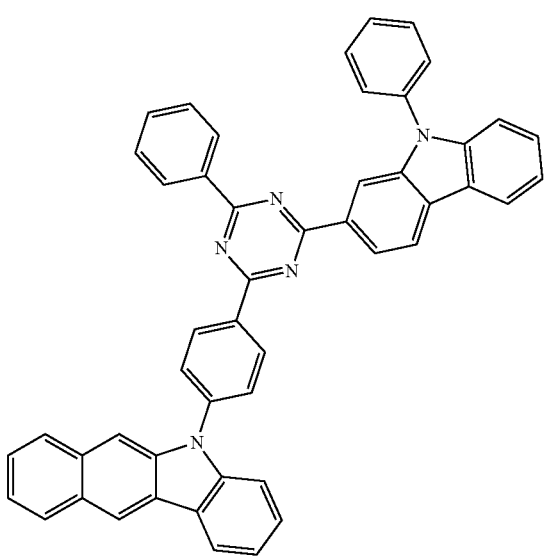
9
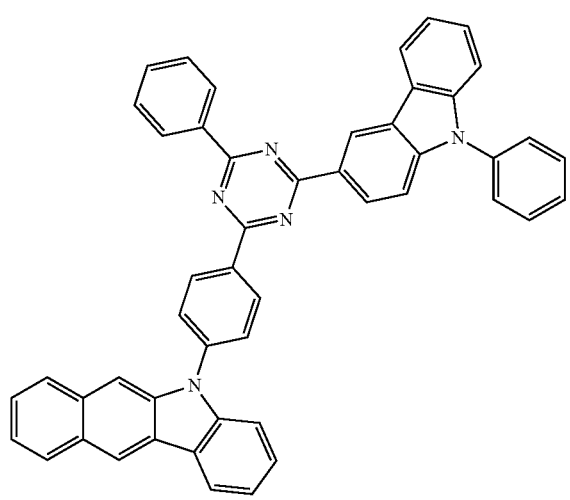
10
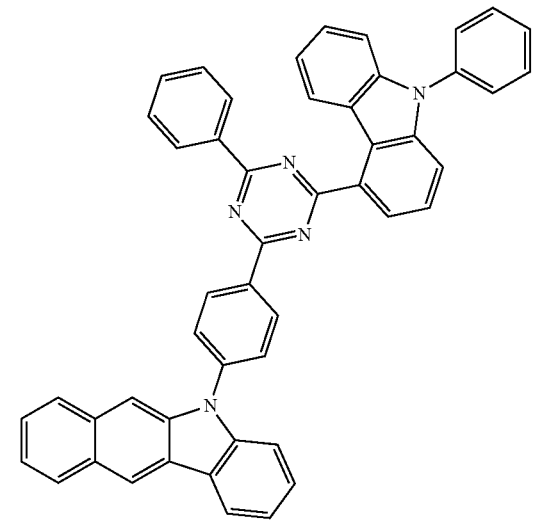
11
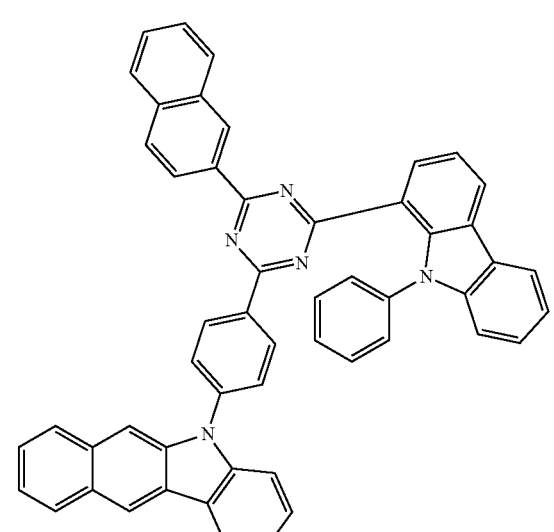
12
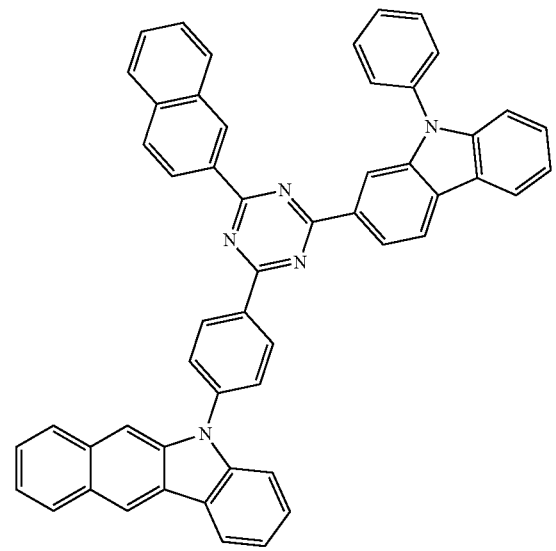

13
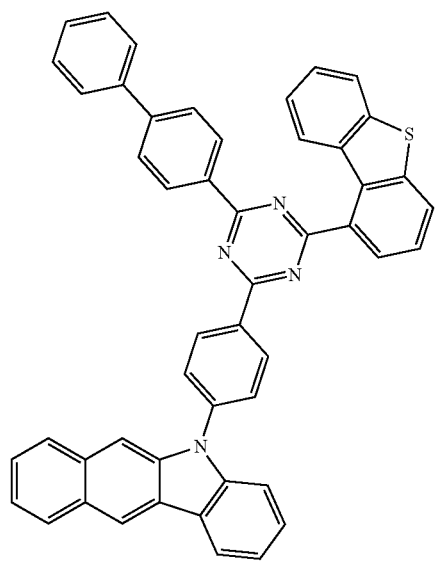
14
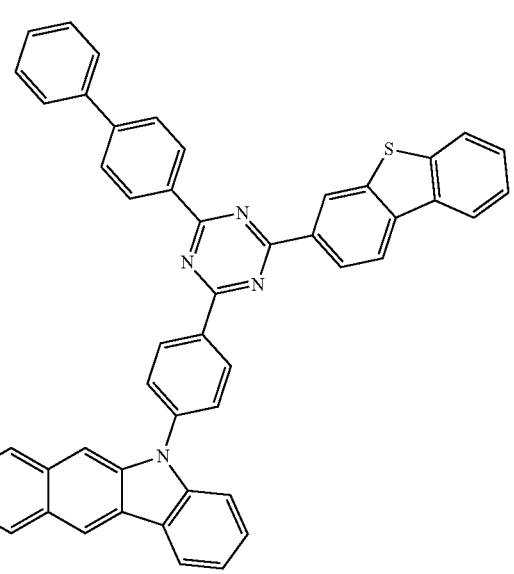
15
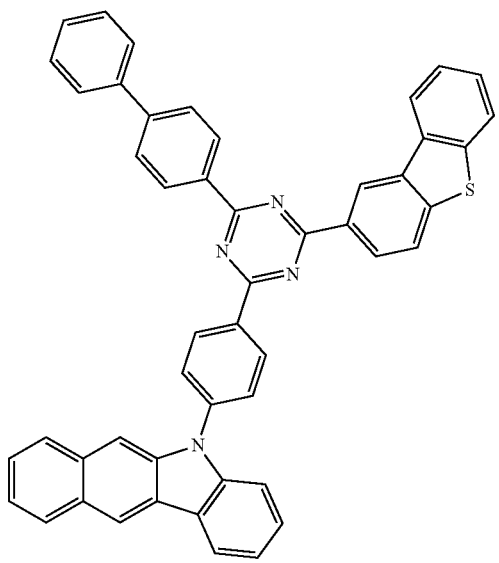
16
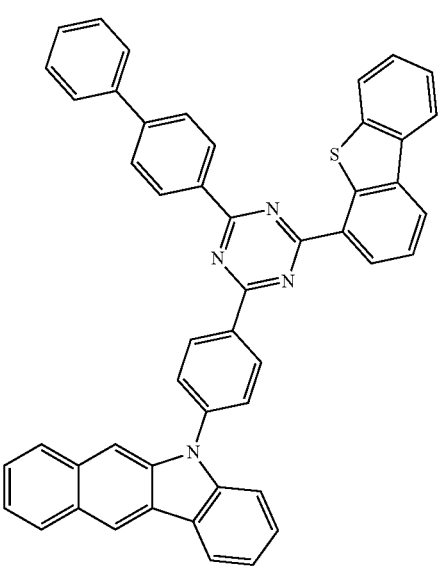
17
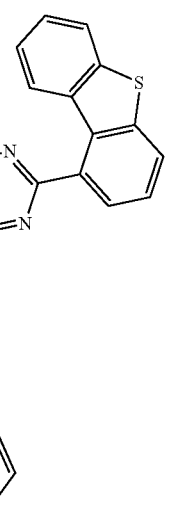

18
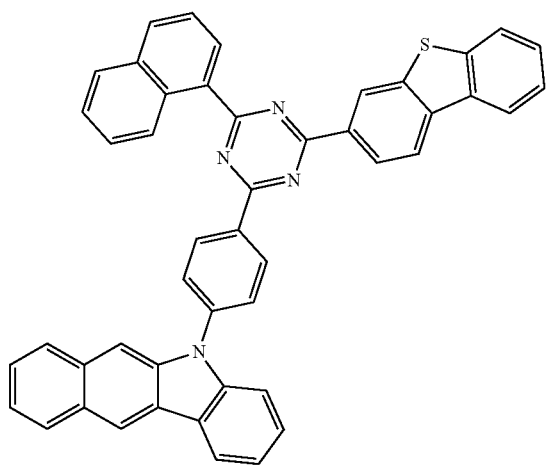
19
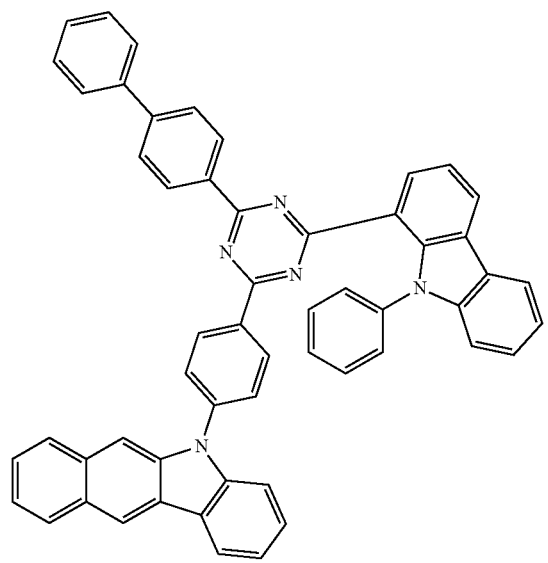
20
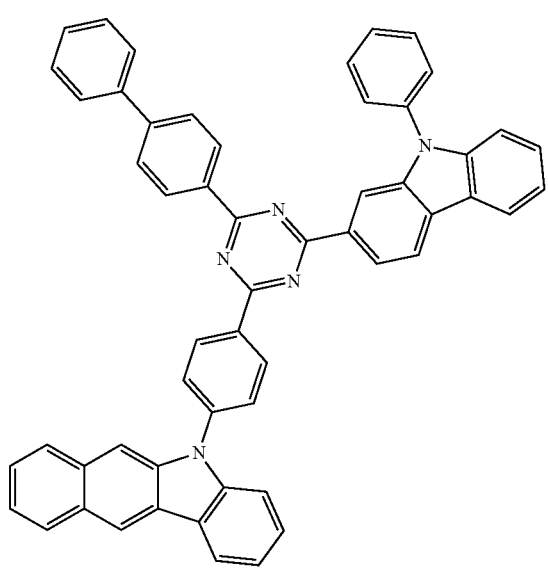
21
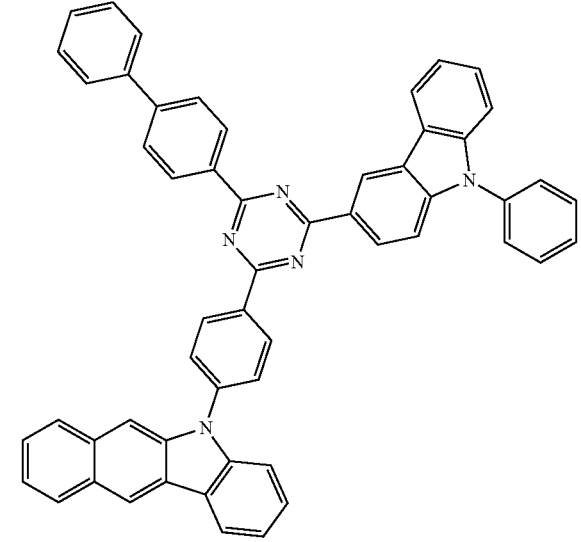
22
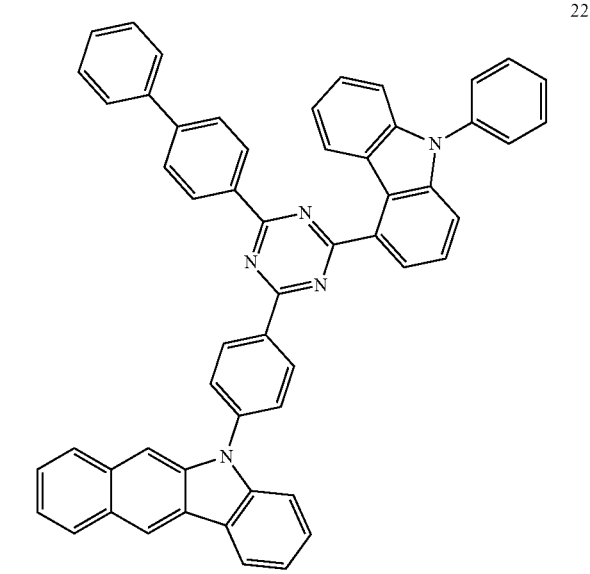
23
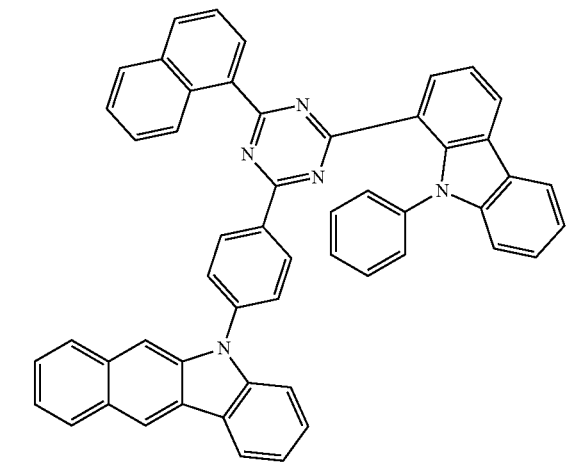

-continued
24
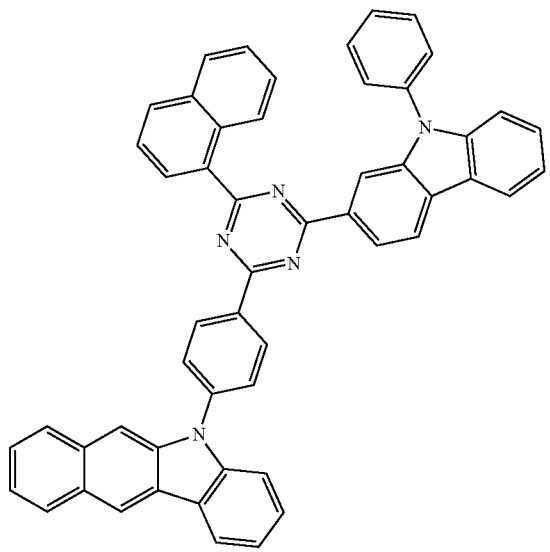
25
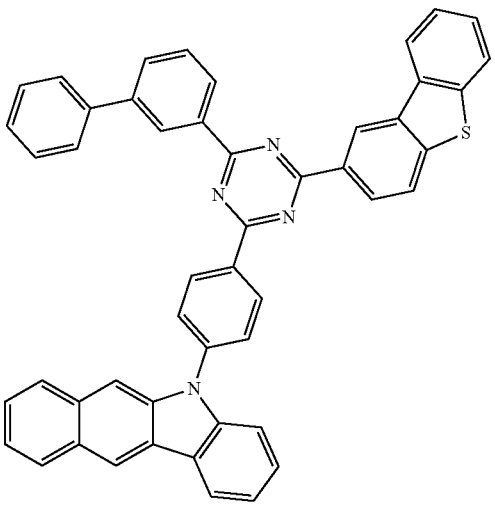
26
27
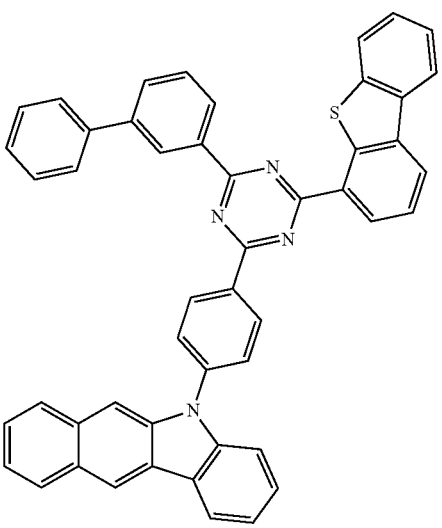
28
29
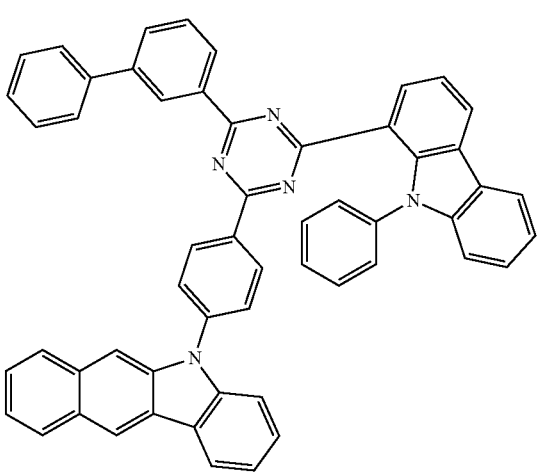

30
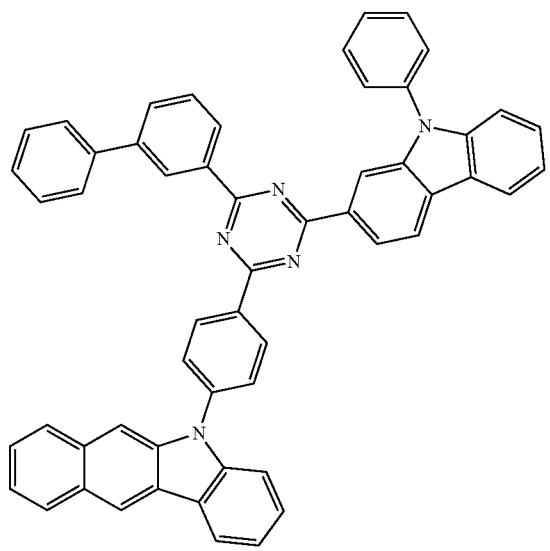
31
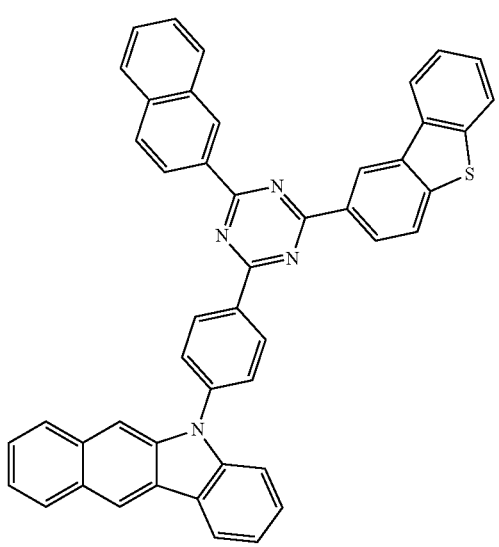
32
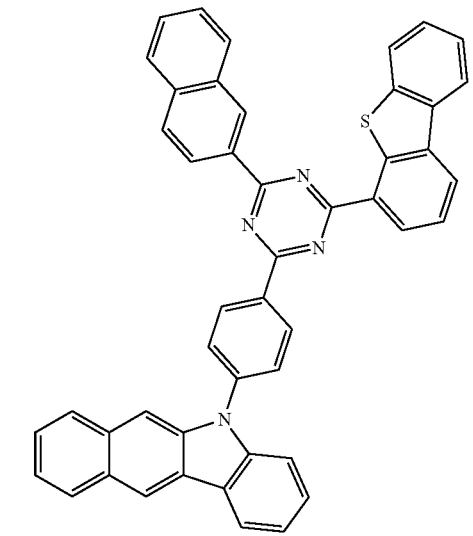
33
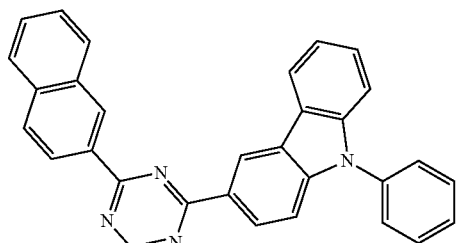
34
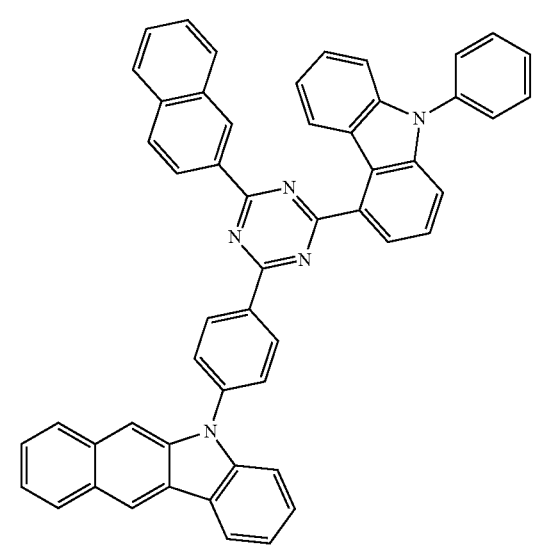
35
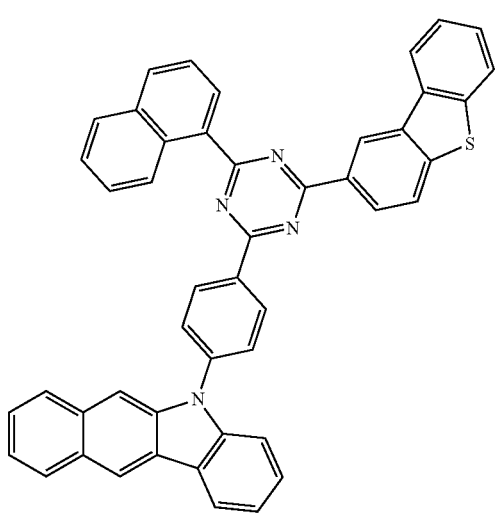

36
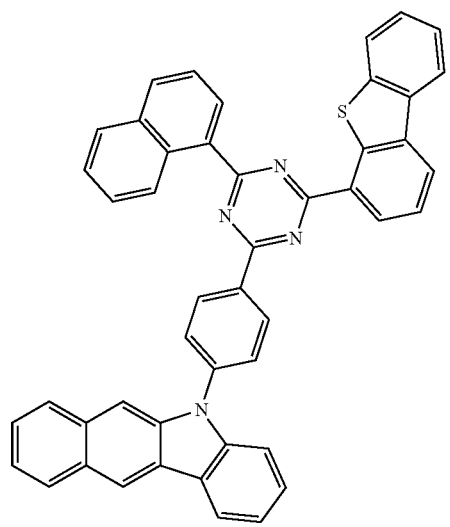
37
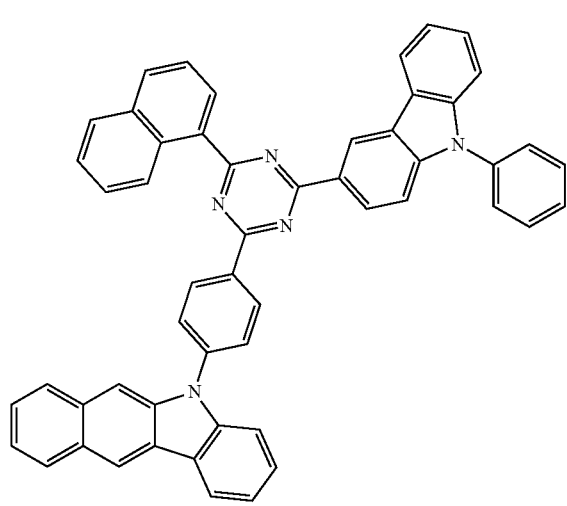
38
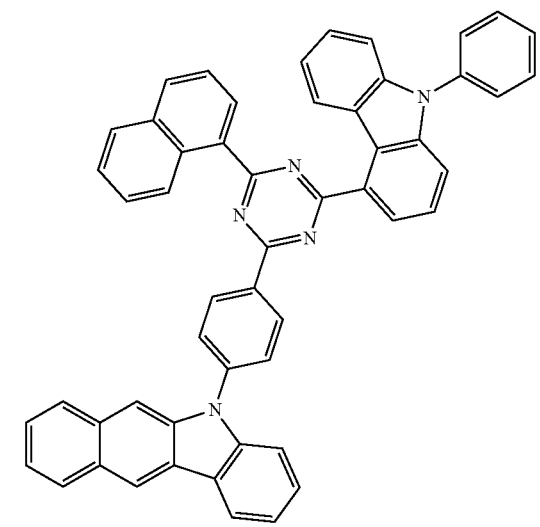
39
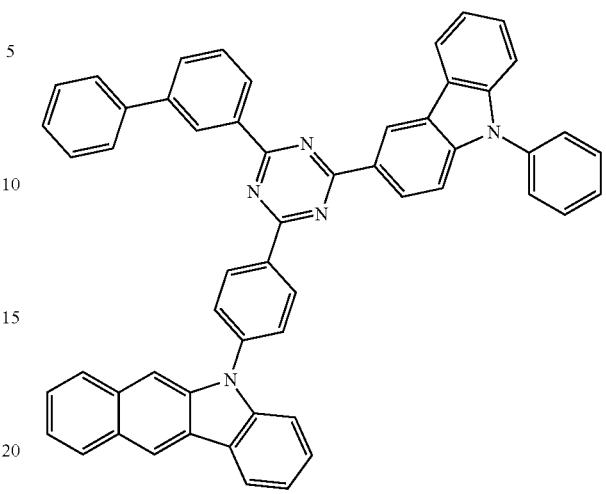
40
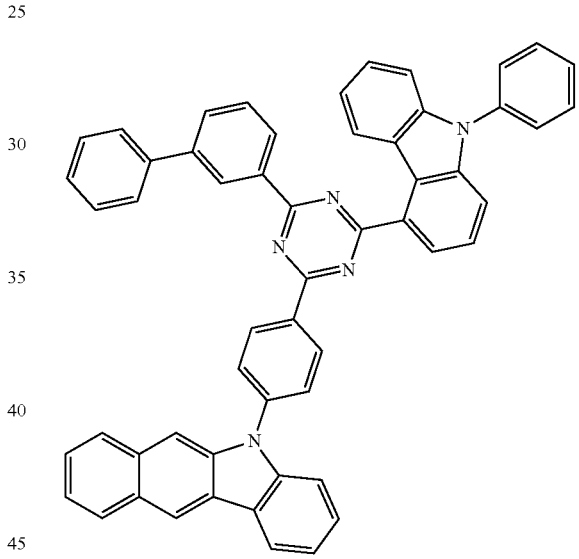
41
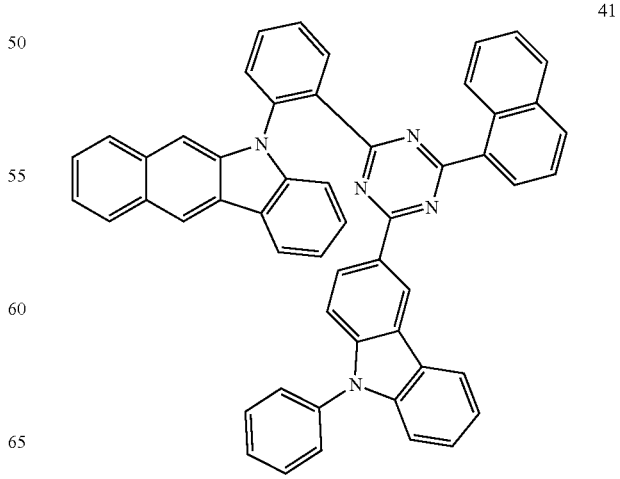

-continued

42

43

44

45

46

47

48
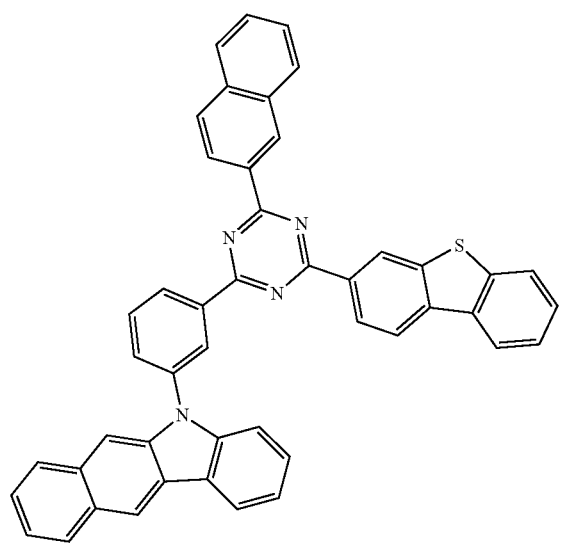
49
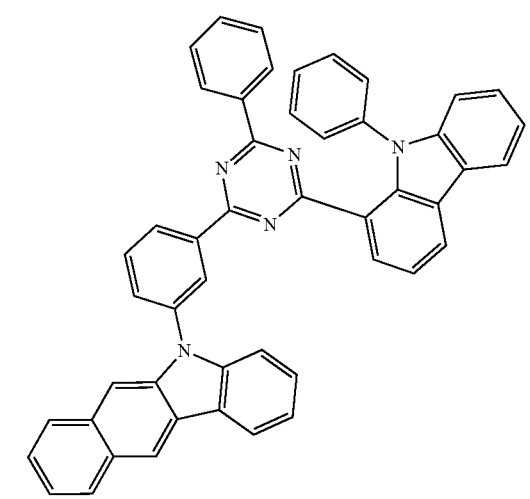
50
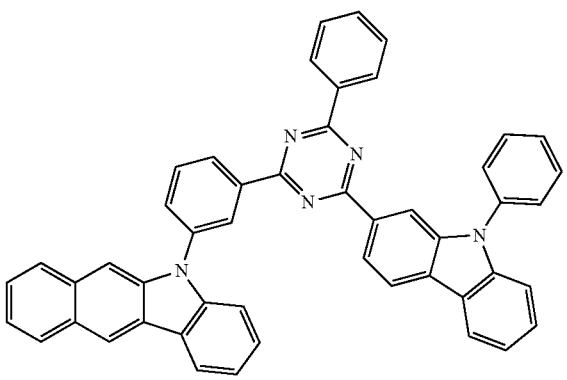
51
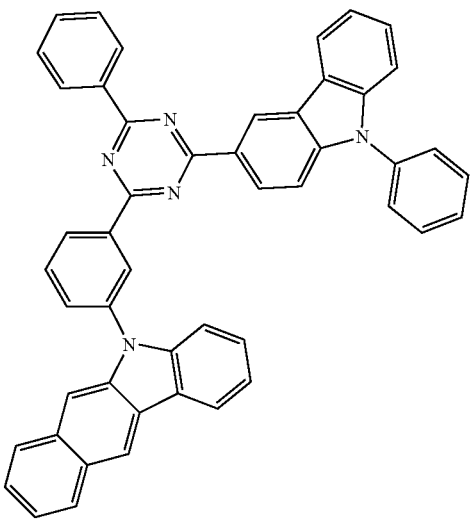
52
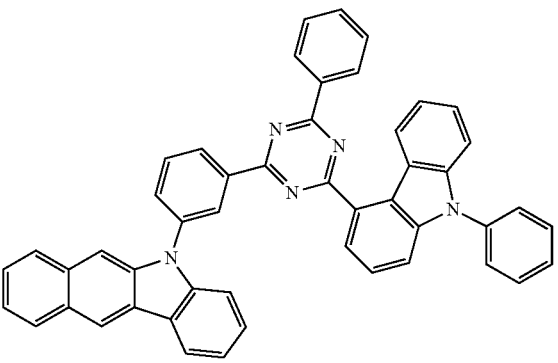
53
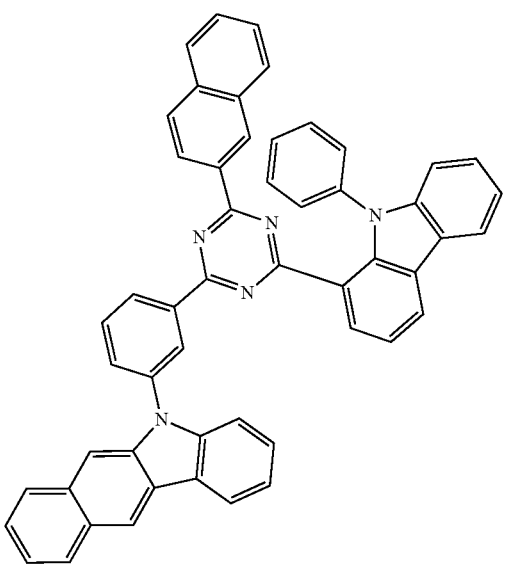

54
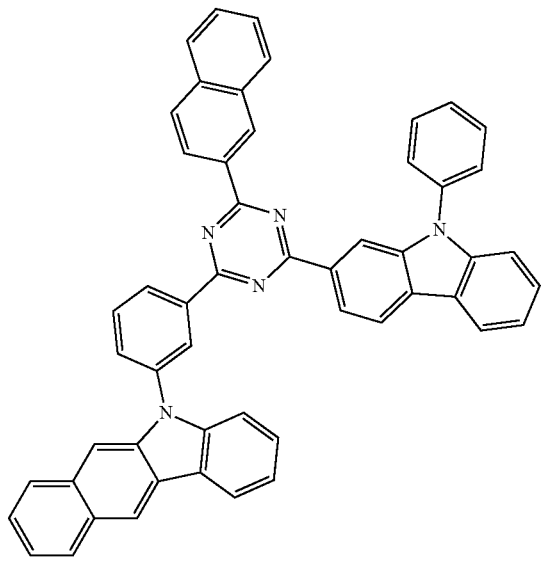
55
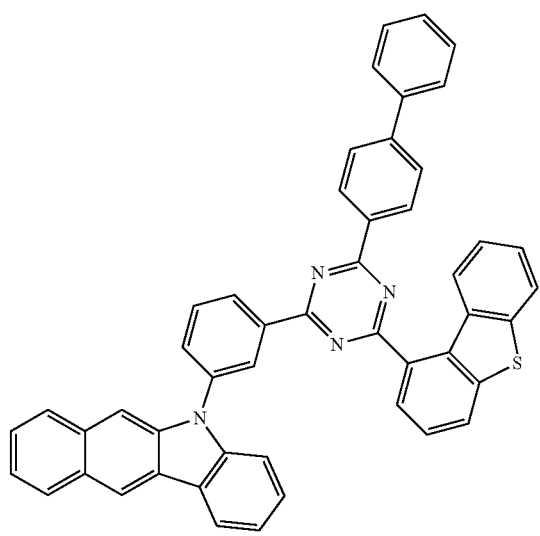
56
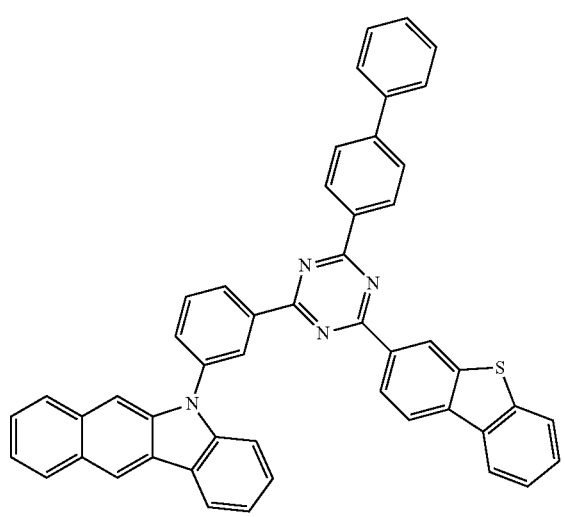
57
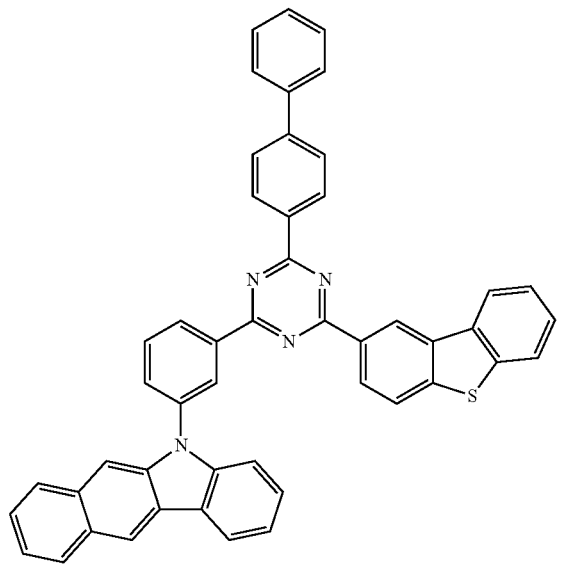
58
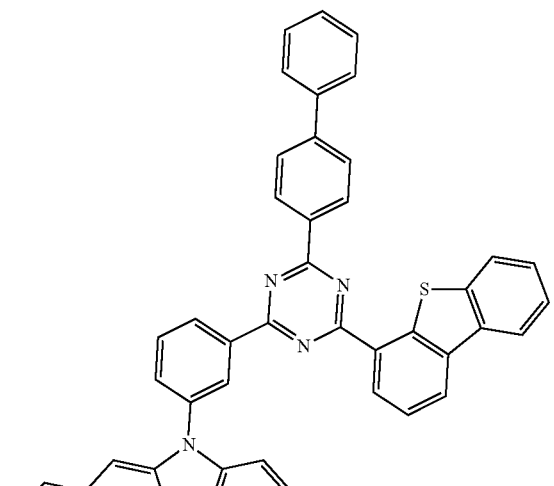
59
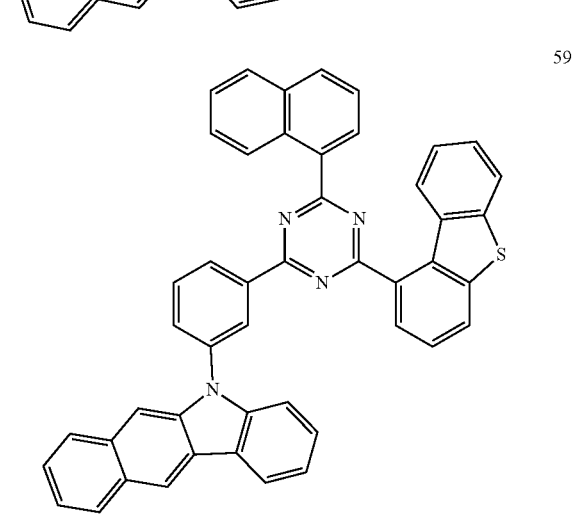

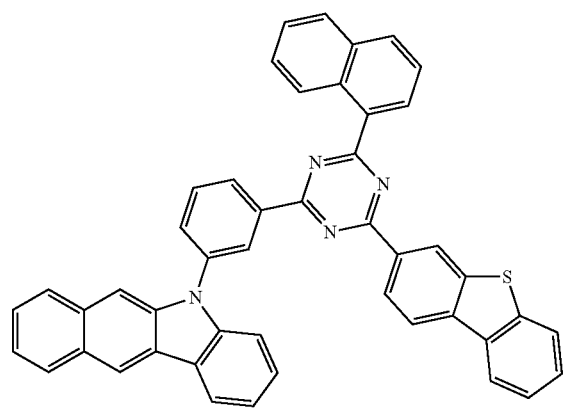
60
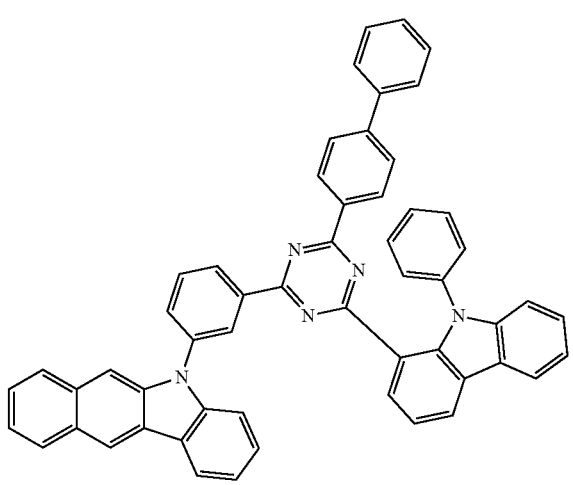
61
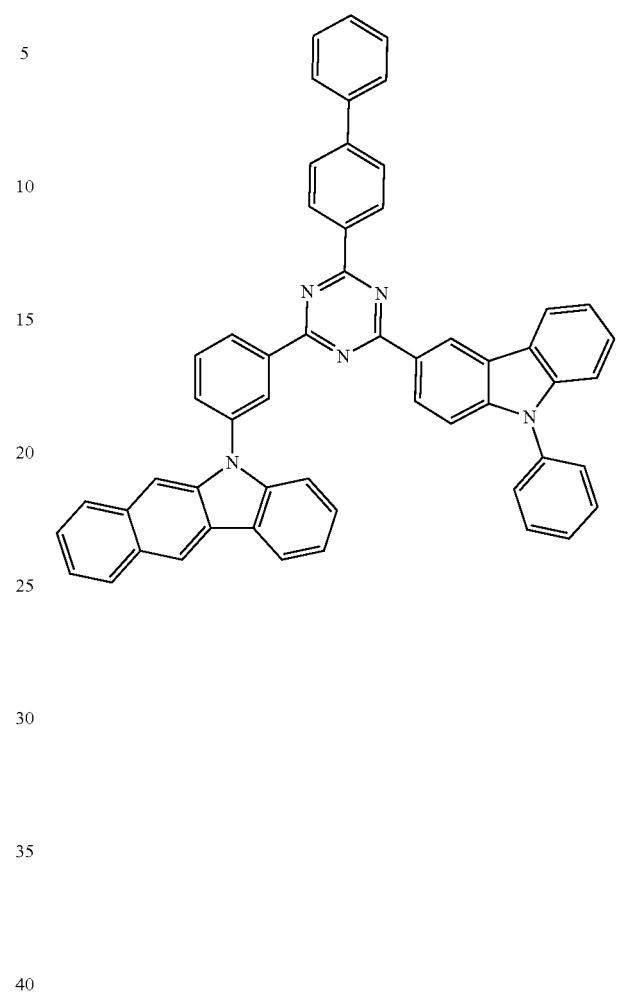
62
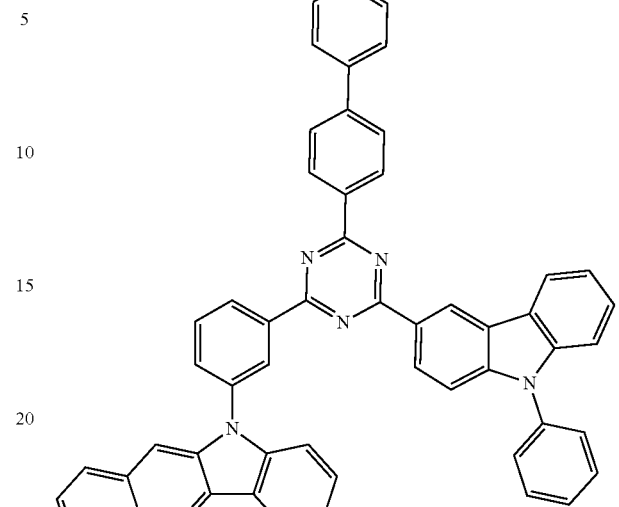
63
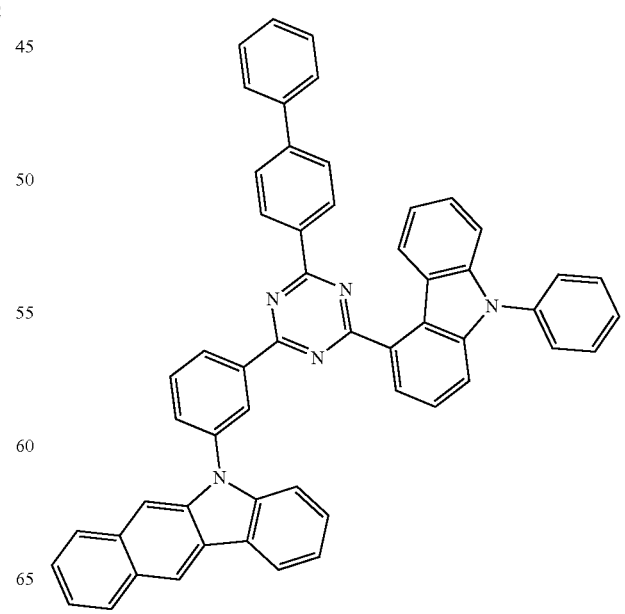
64

65
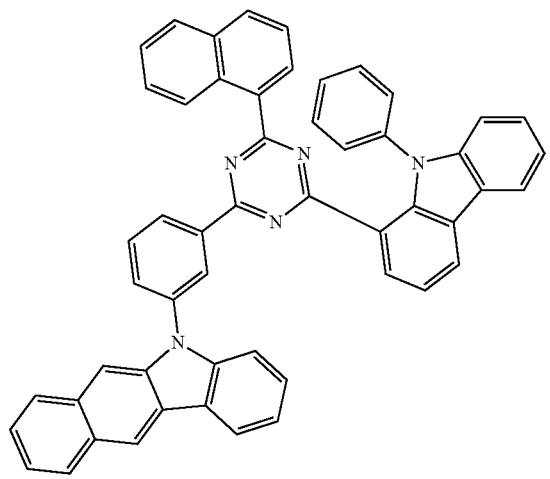
66
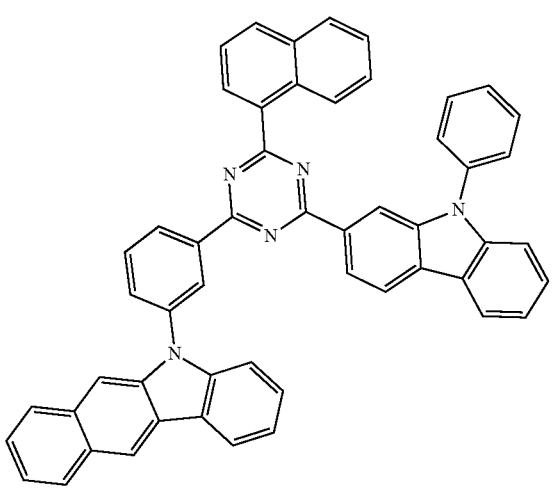
67
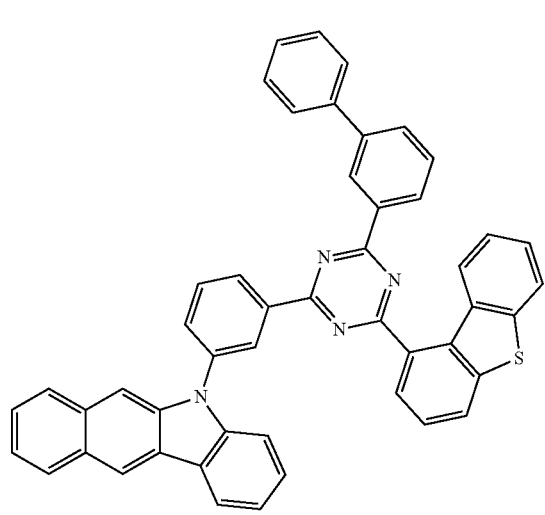
68
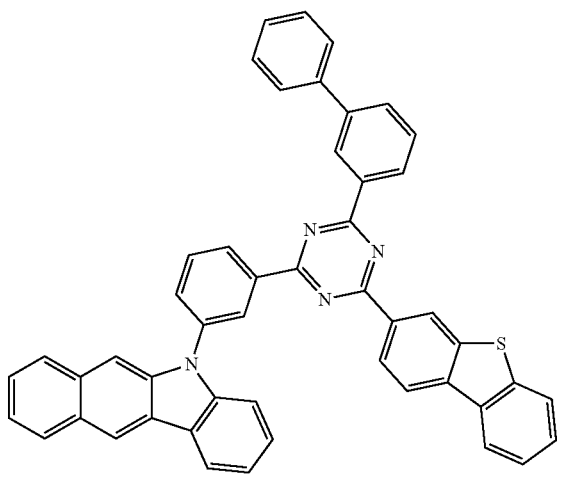
69
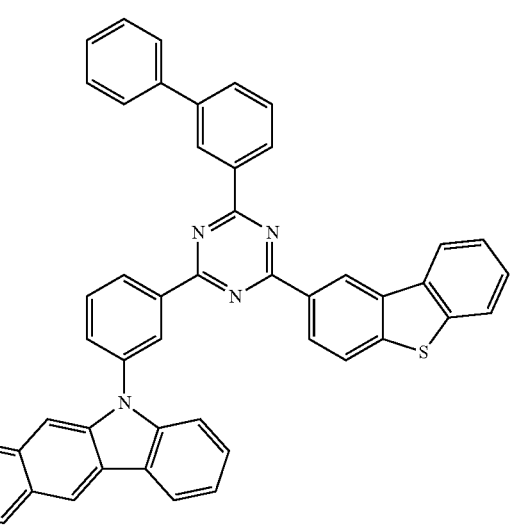
70
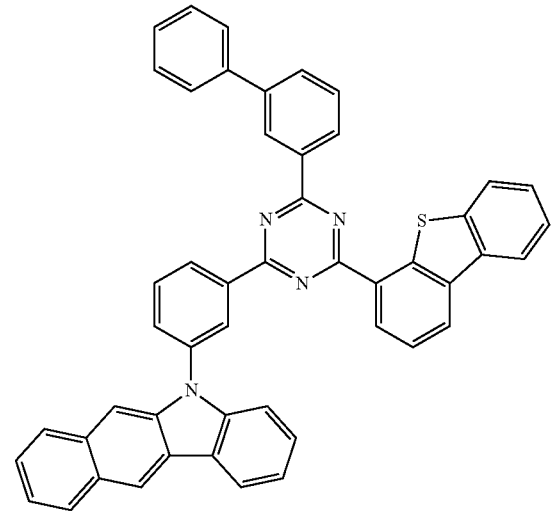

71
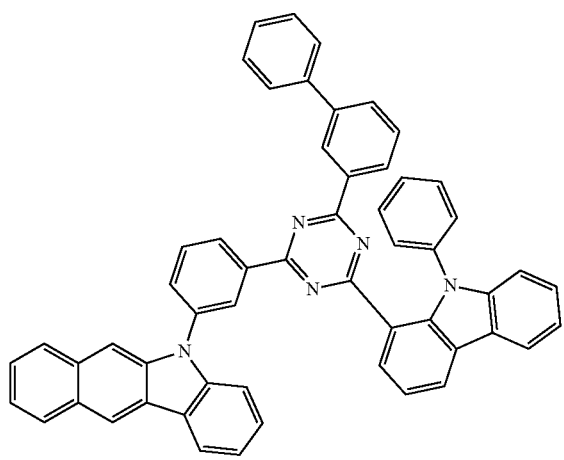
72
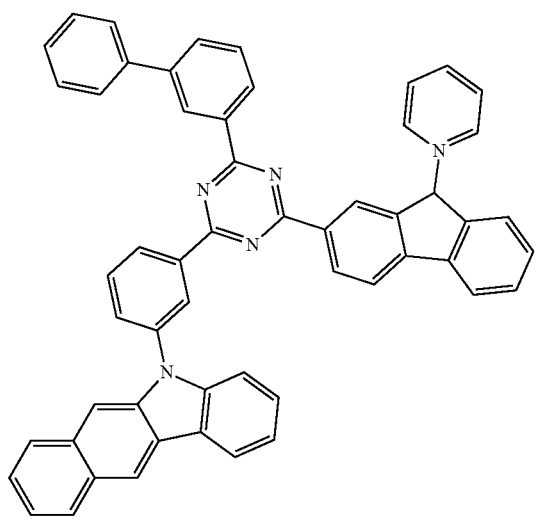
73
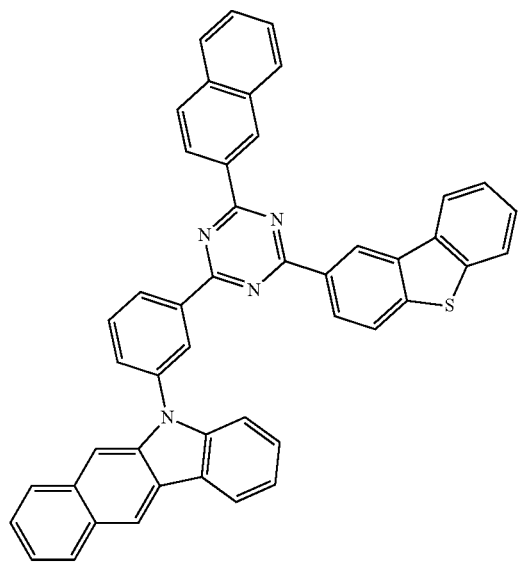
74
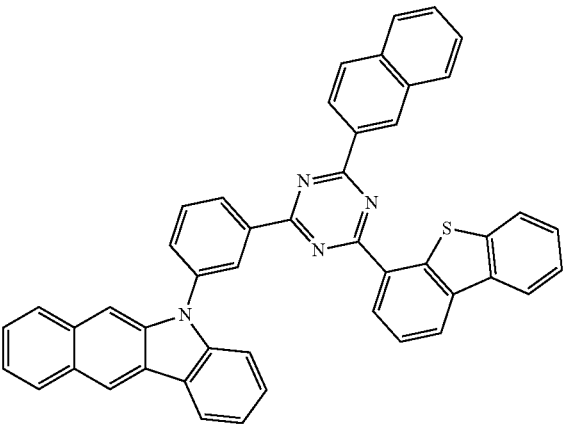
75
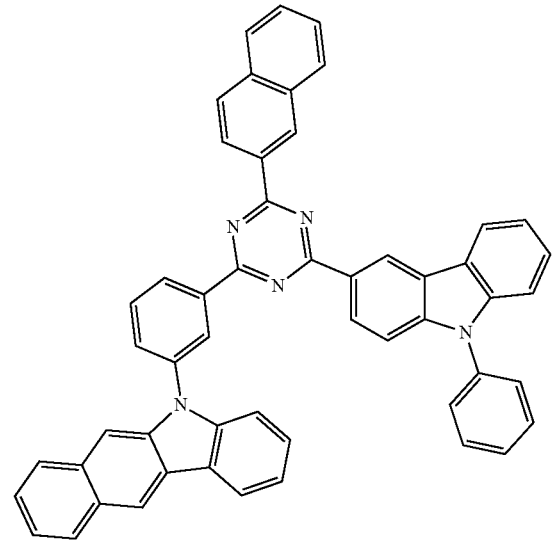
76
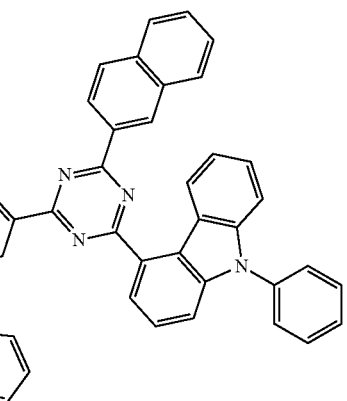

77
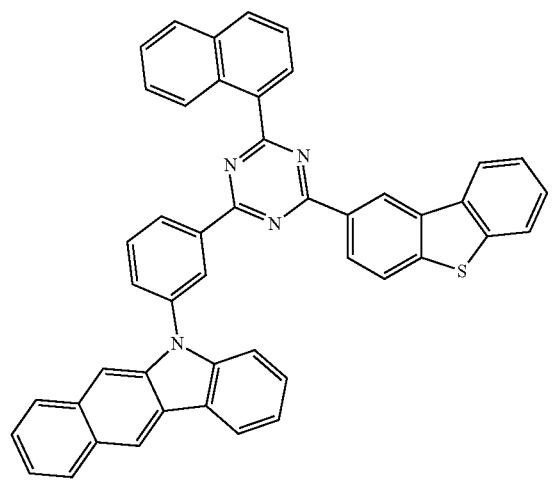
80
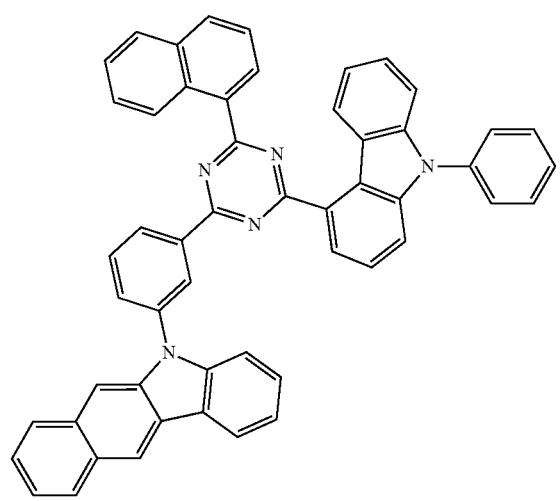
78
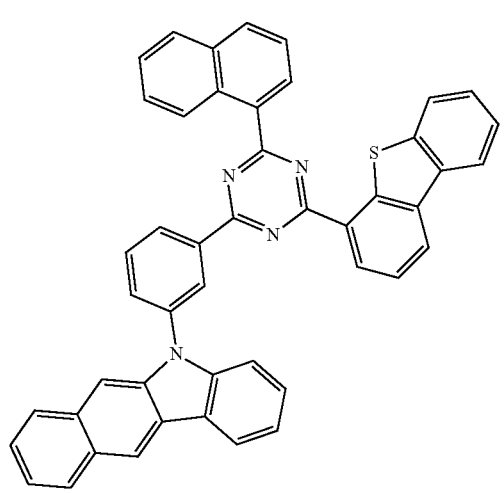
81
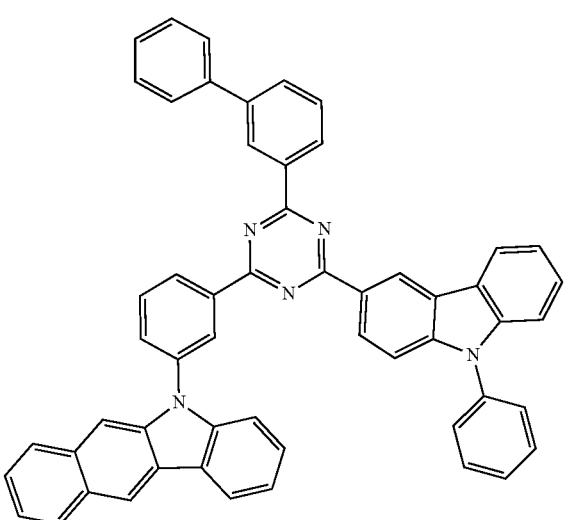
79
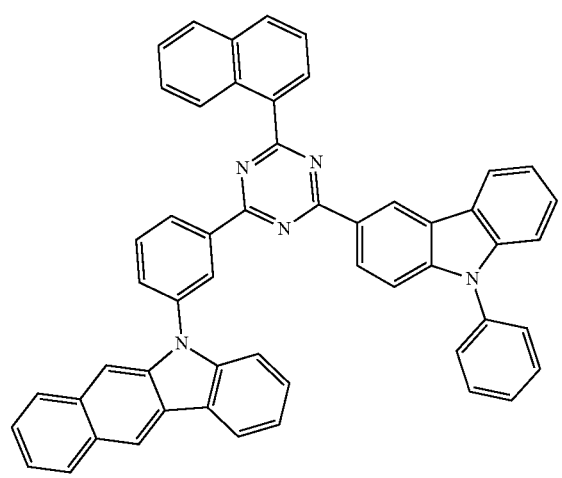
82
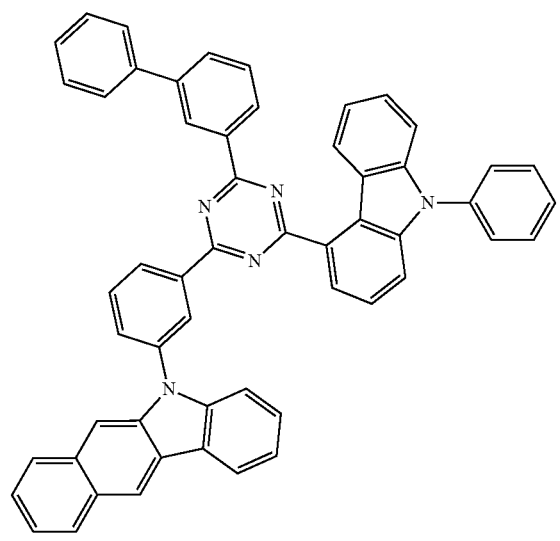

83
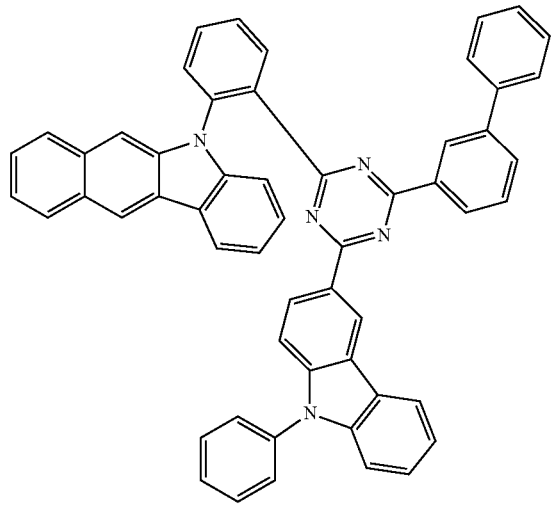
84
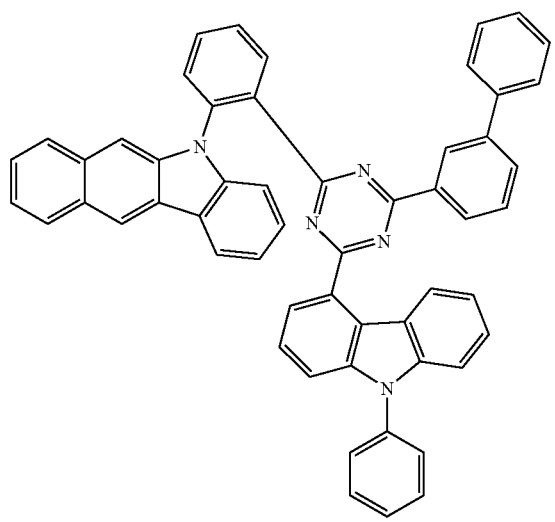
85
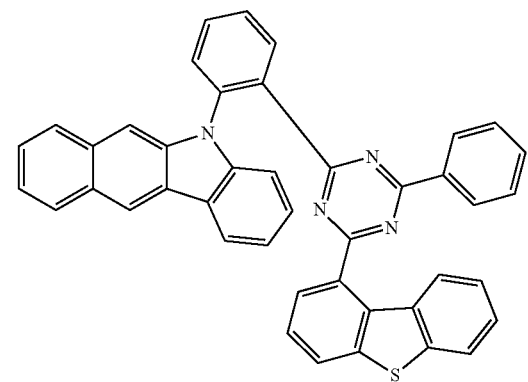
86
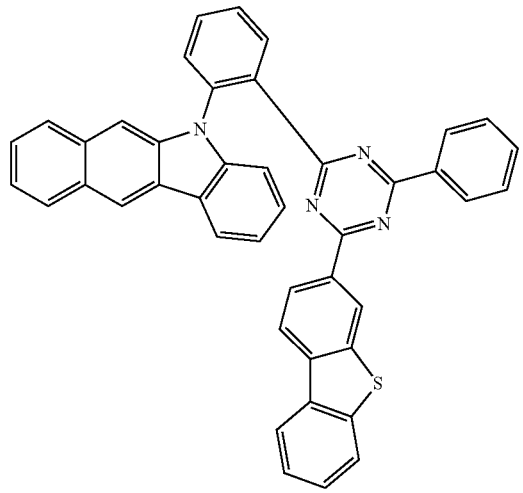
87
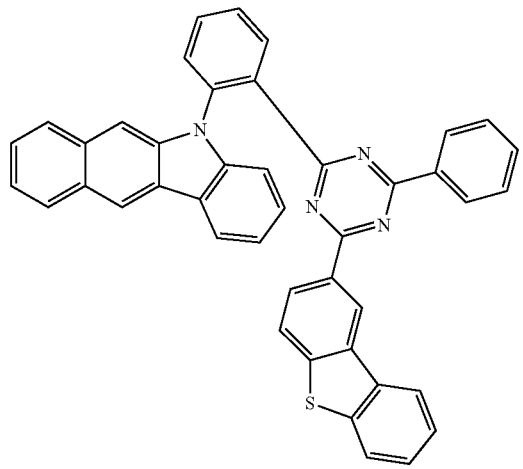
88
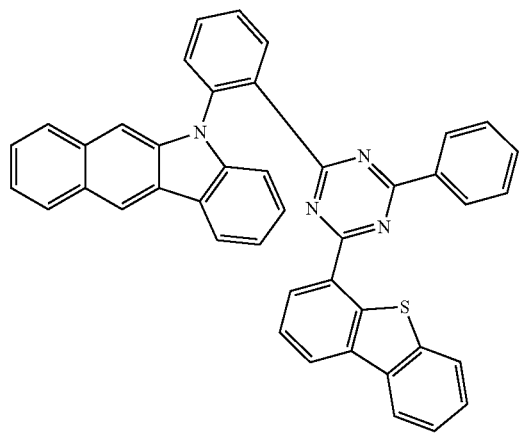

-continued
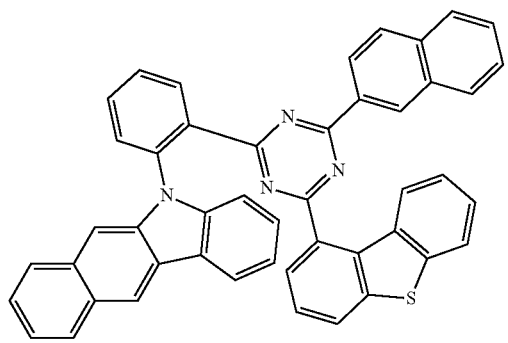
89
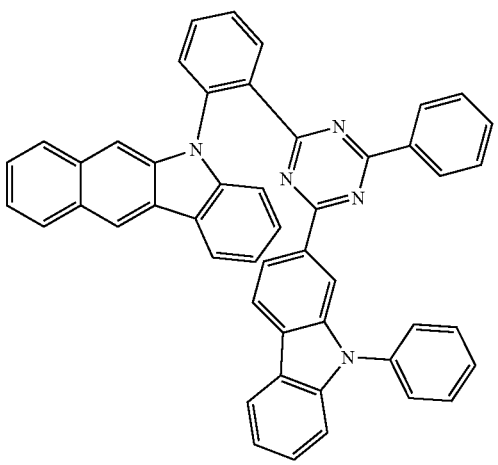
92
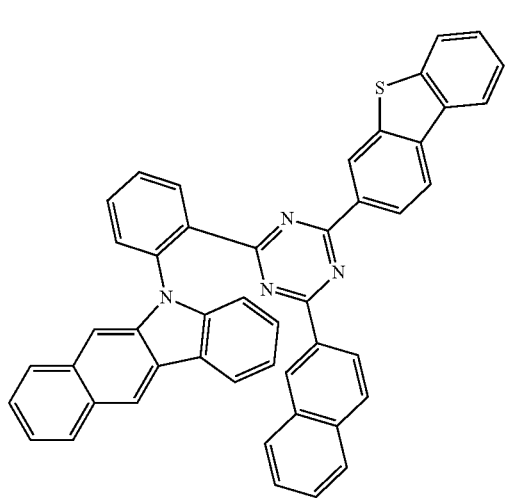
90
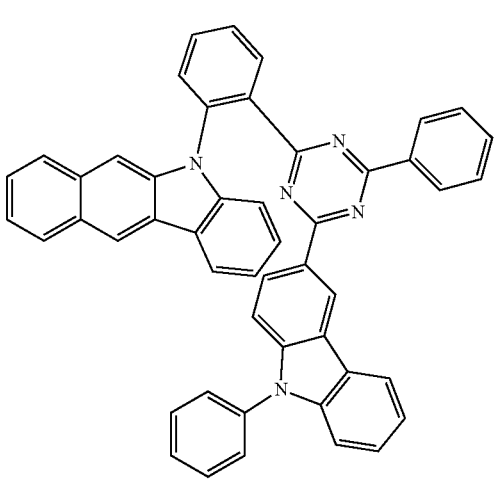
93
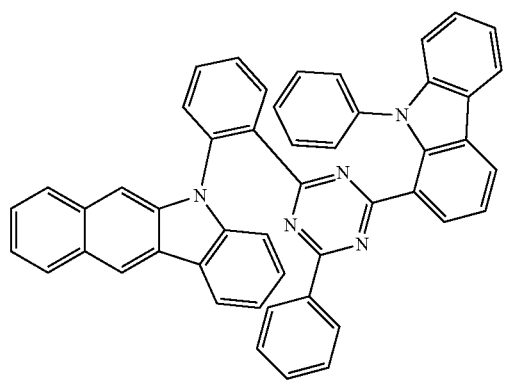
91
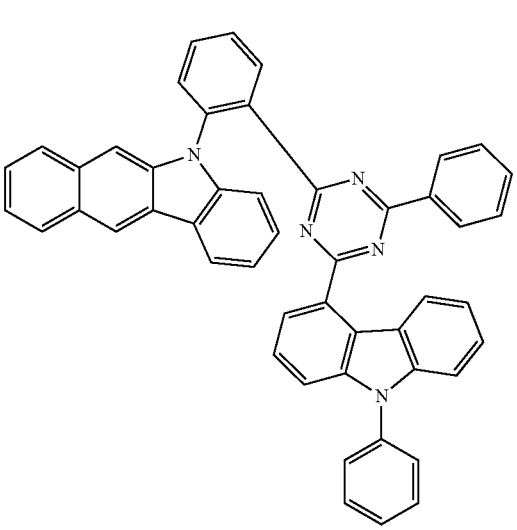
94

95
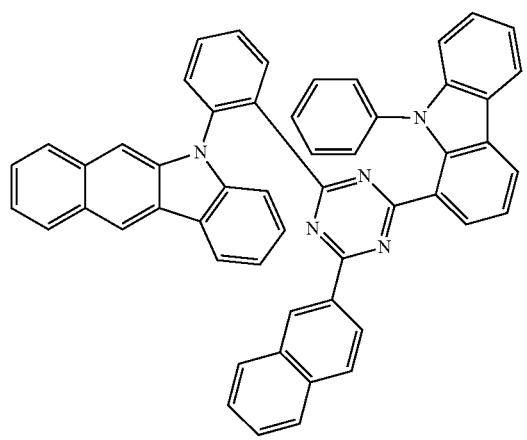
98
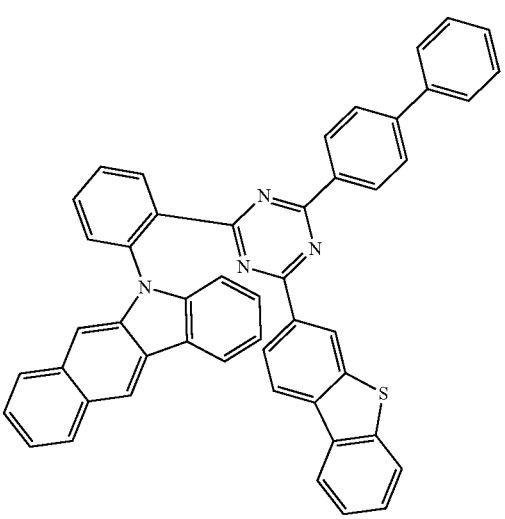
96
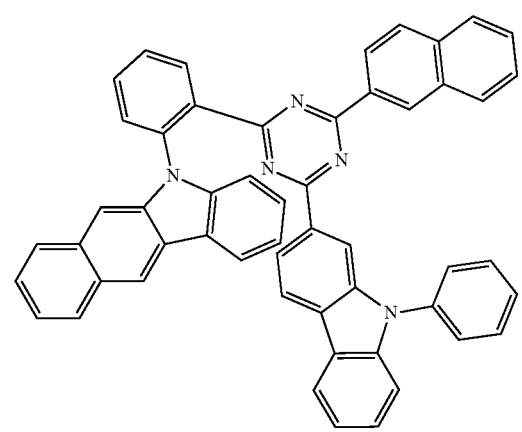
99
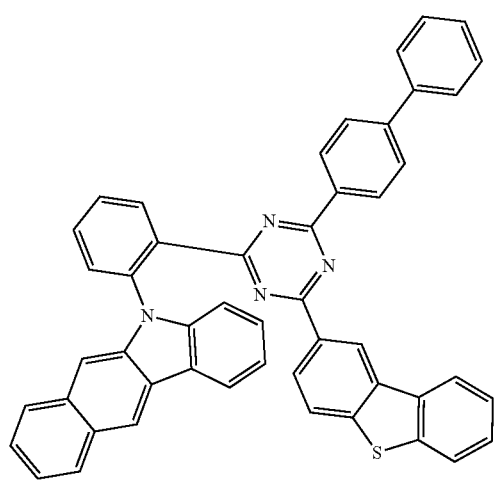
97
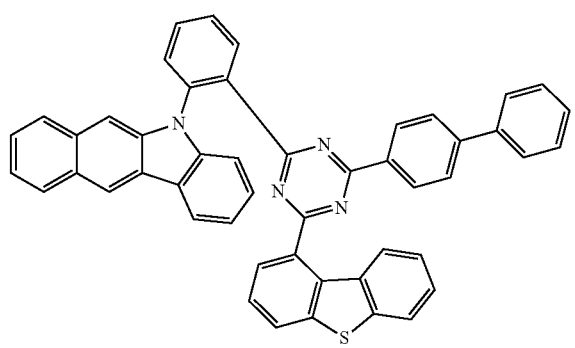
100
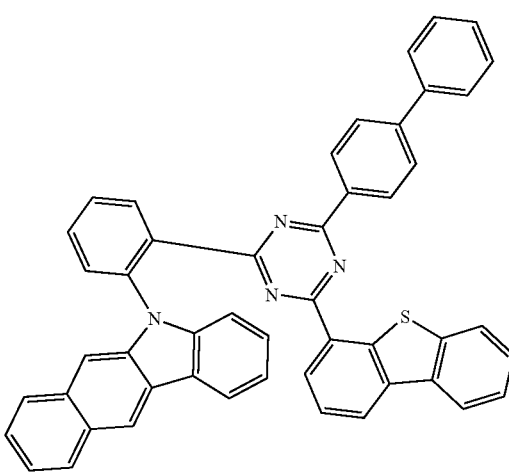

101
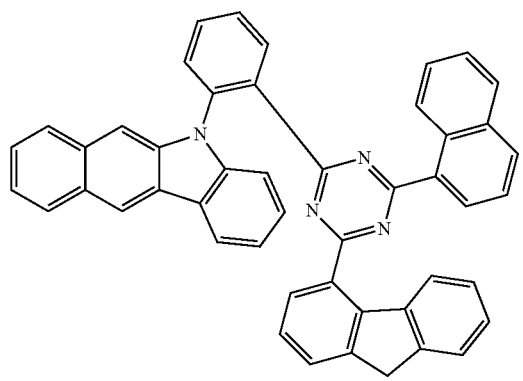
102
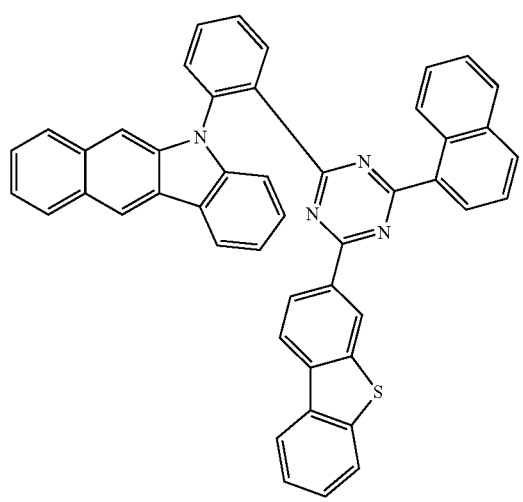
103
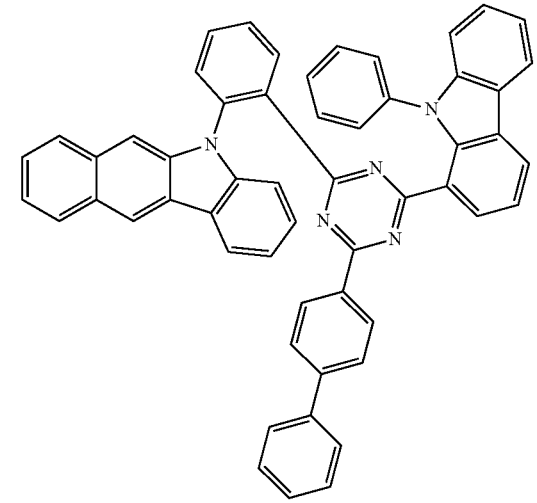
104
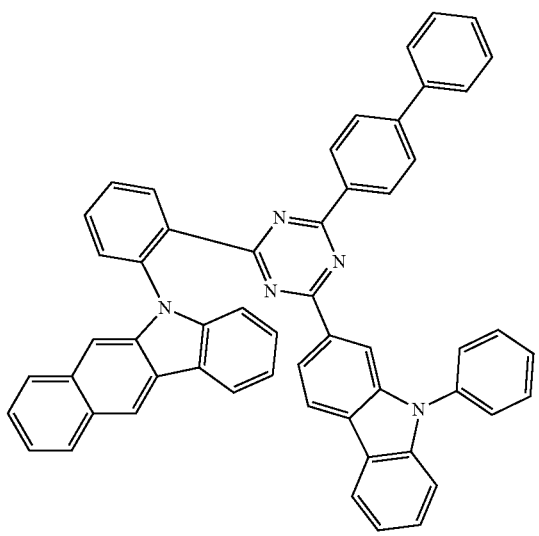
105
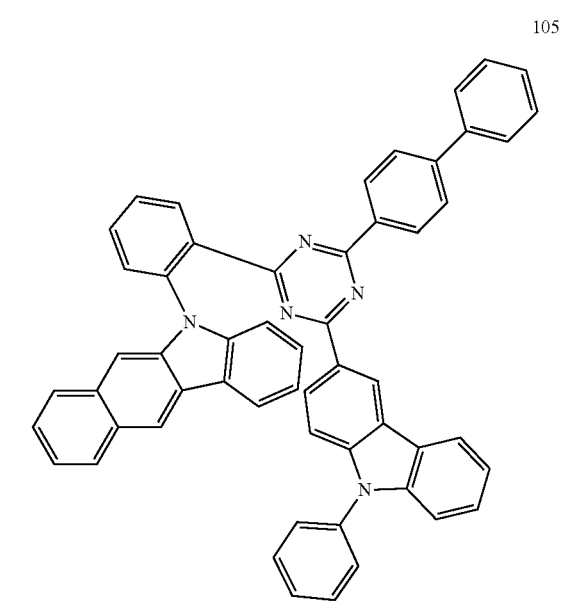
106
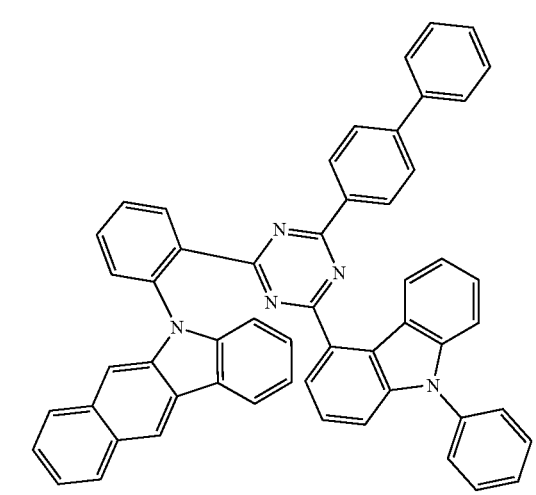

-continued
107
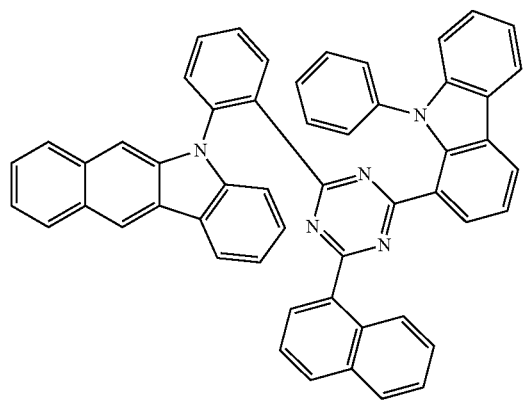
108
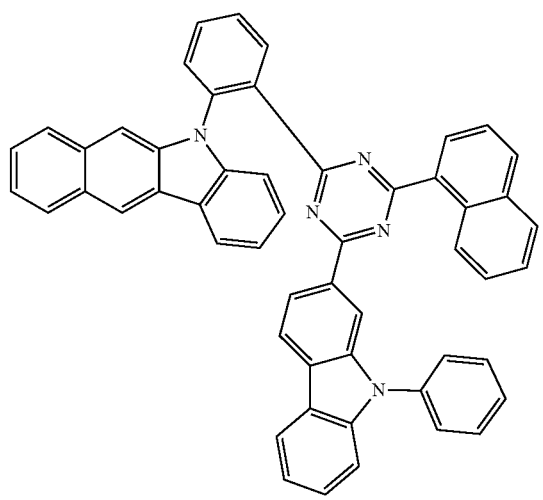
109
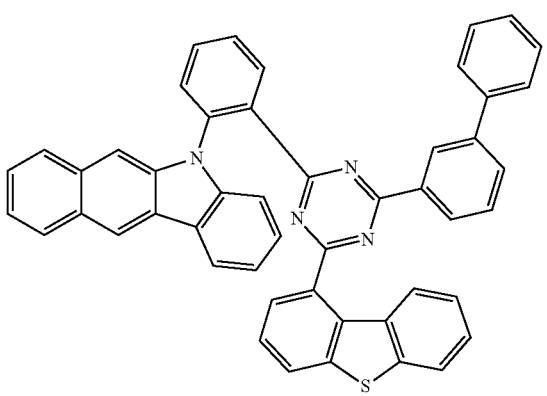
-continued
110
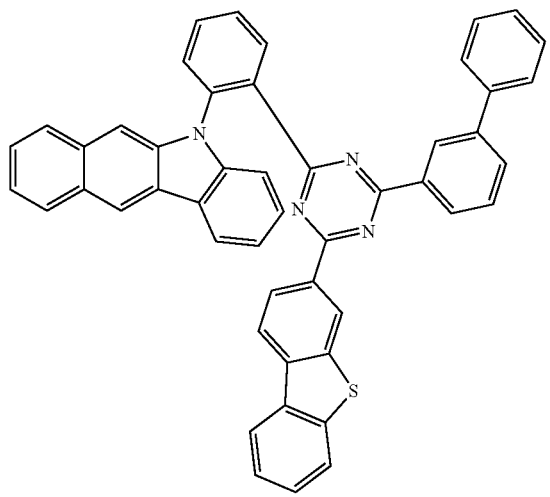
111
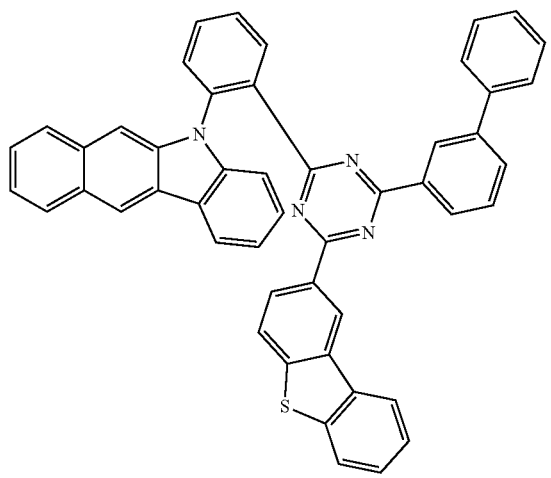
112
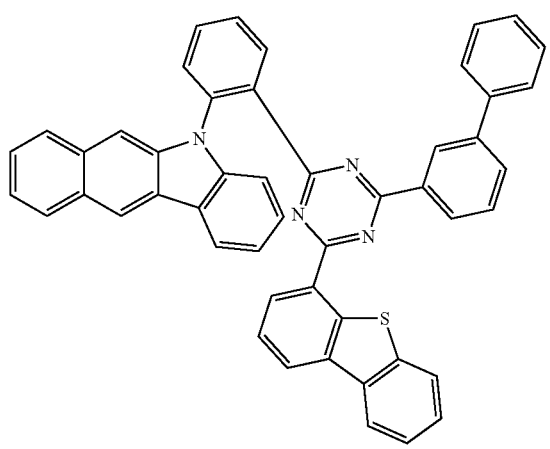

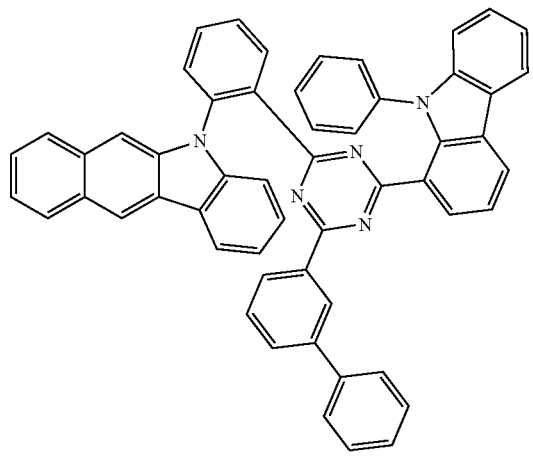
113
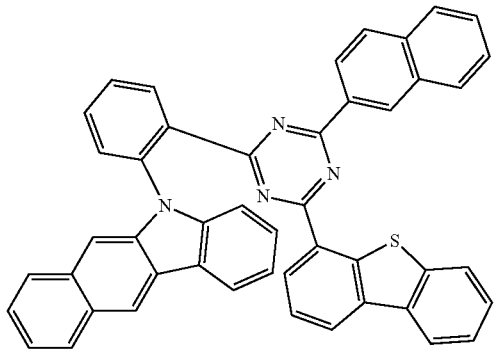
116
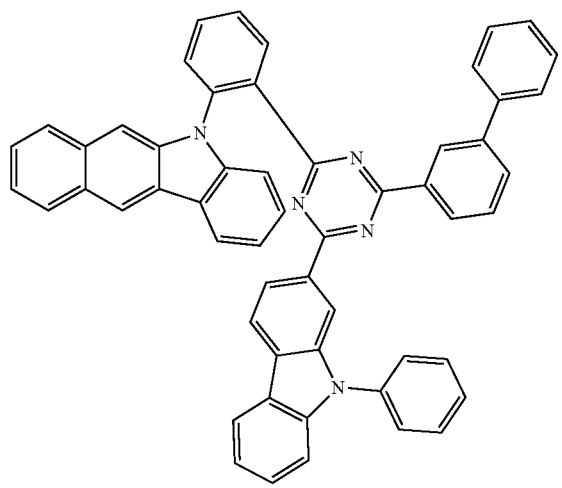
114
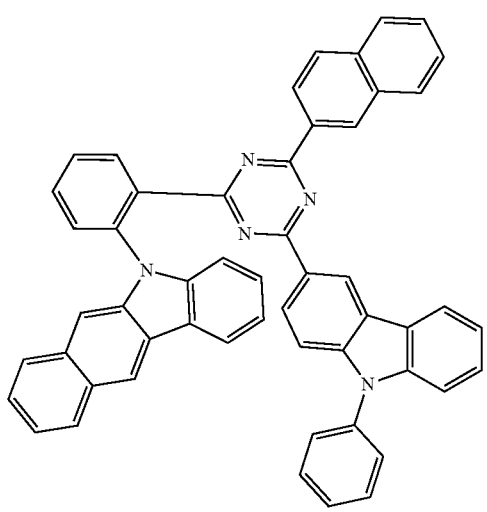
117
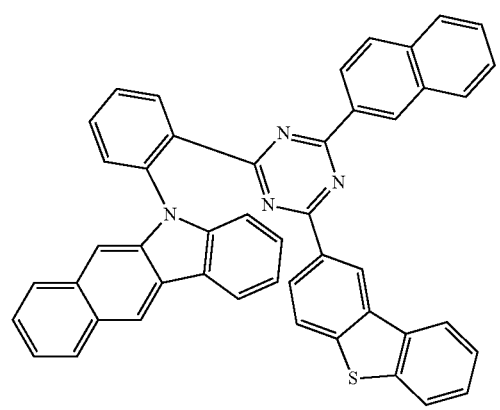
115
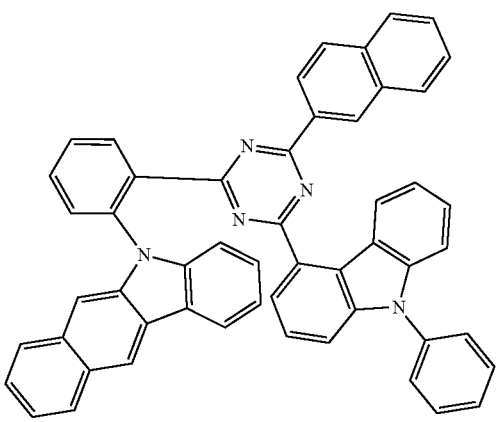
118

119 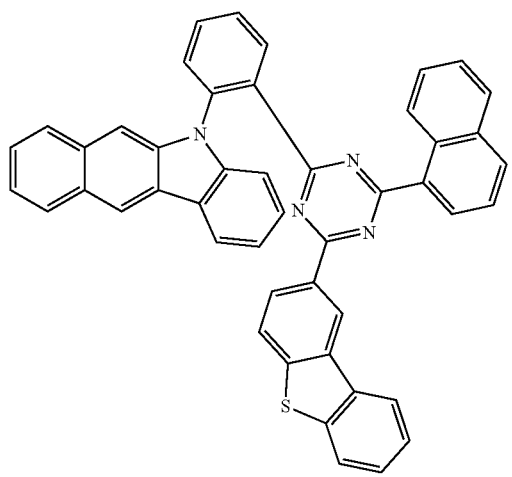
120 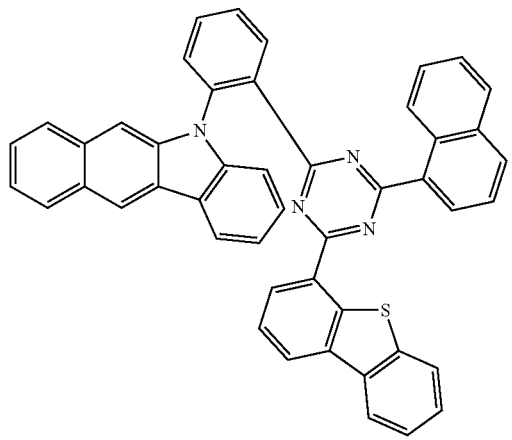
121 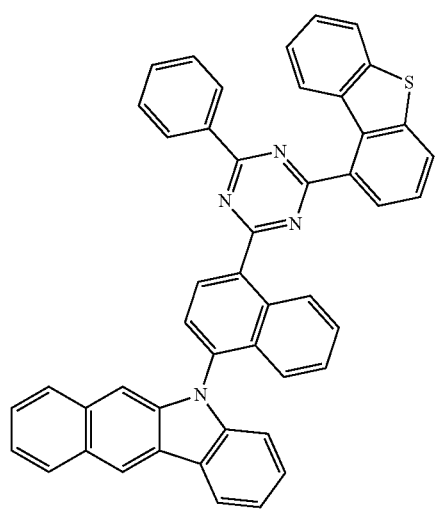
122 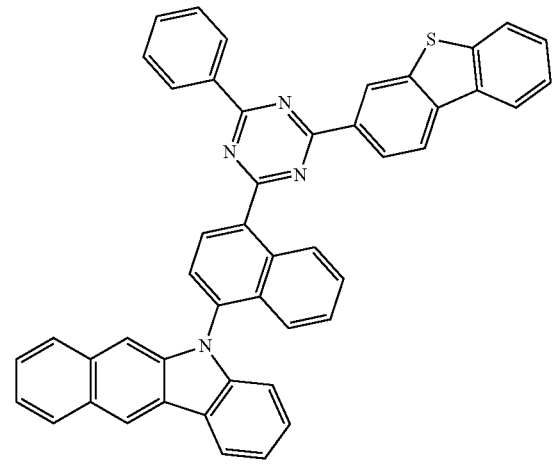
123 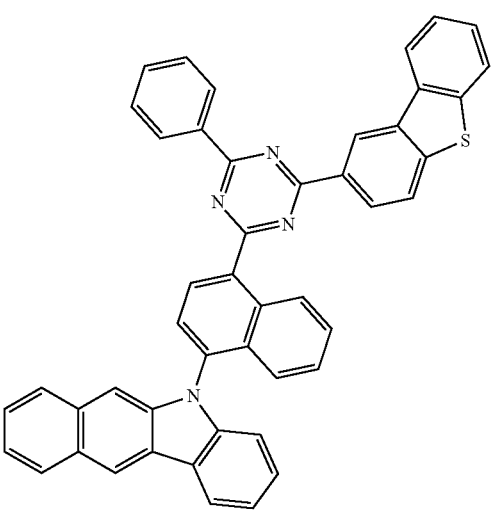
124 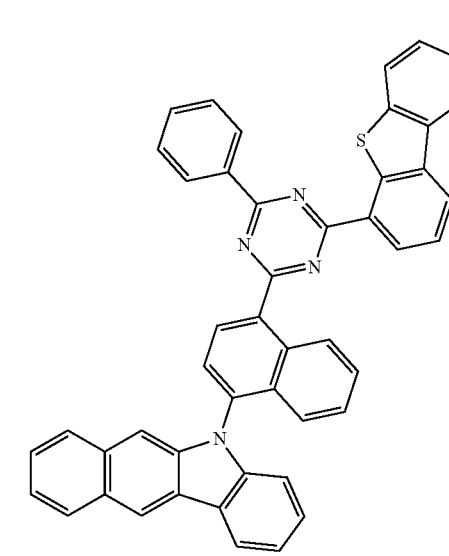

125
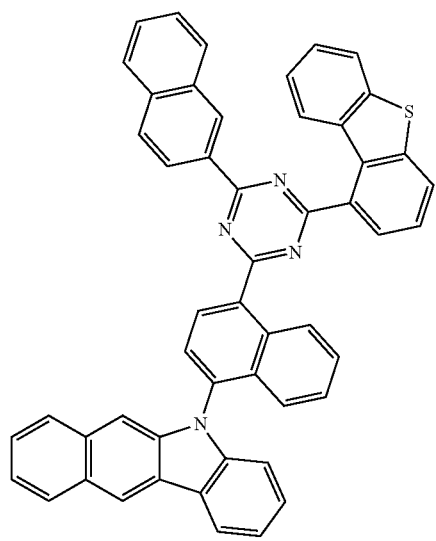
126
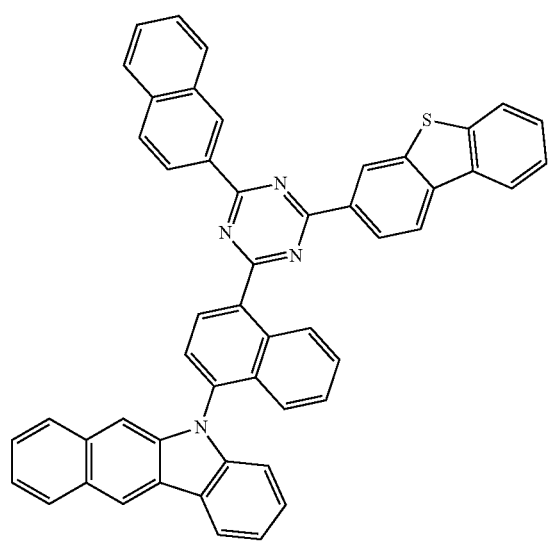
127
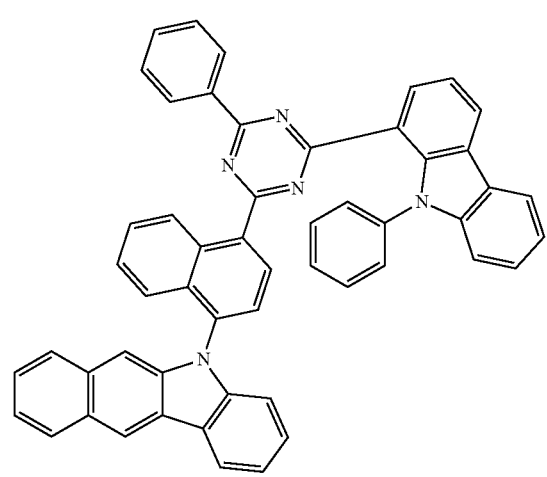
128
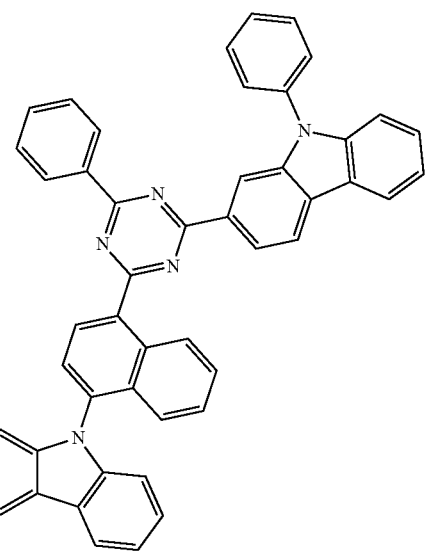
129
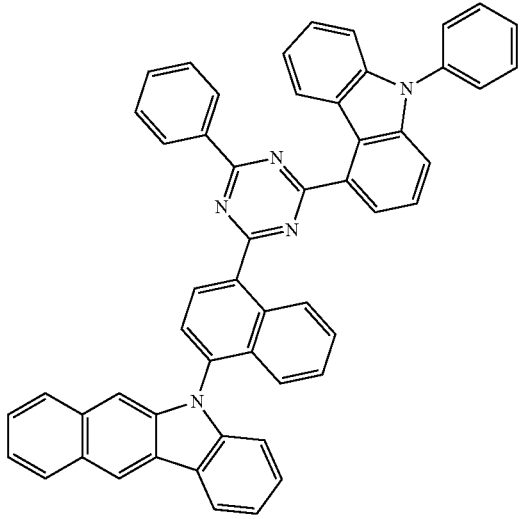
130

131
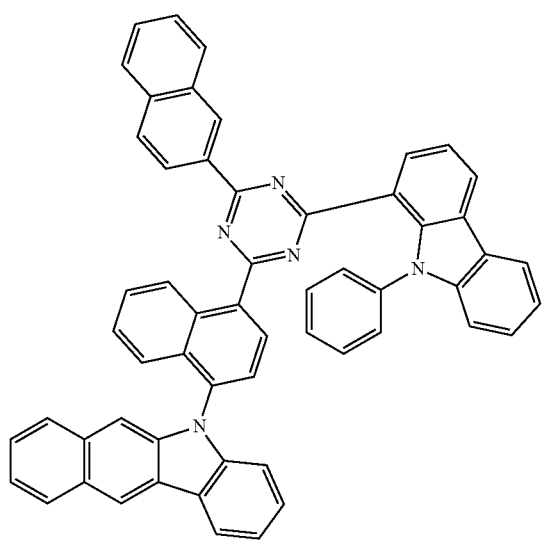
132
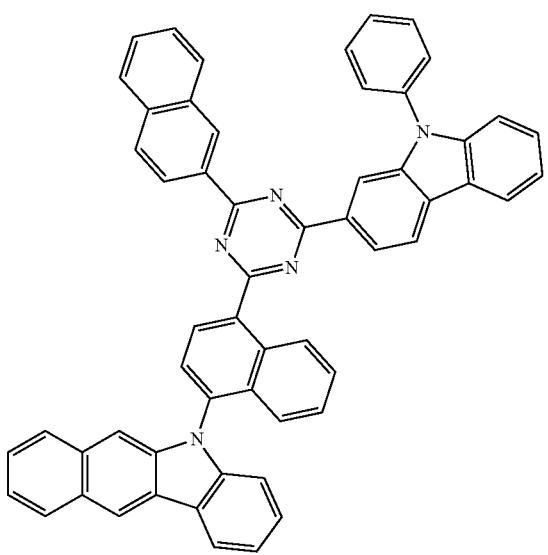
133
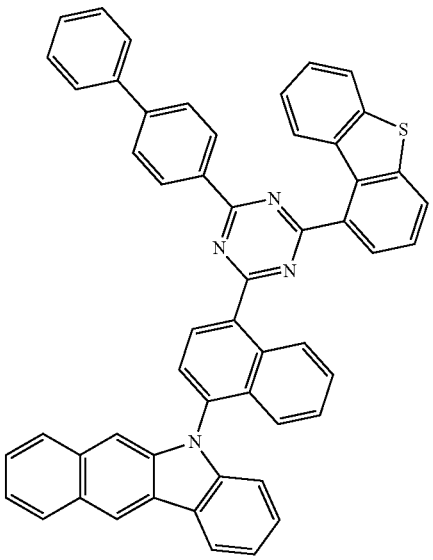
134
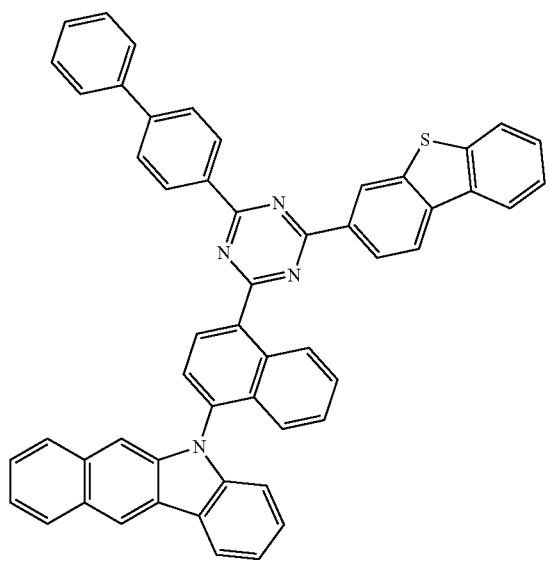

135
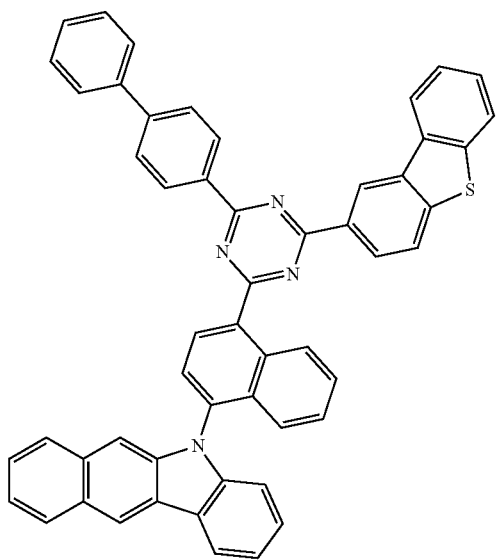
136
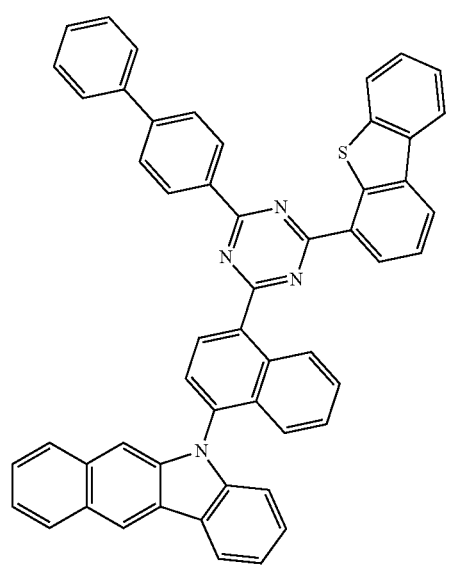
137
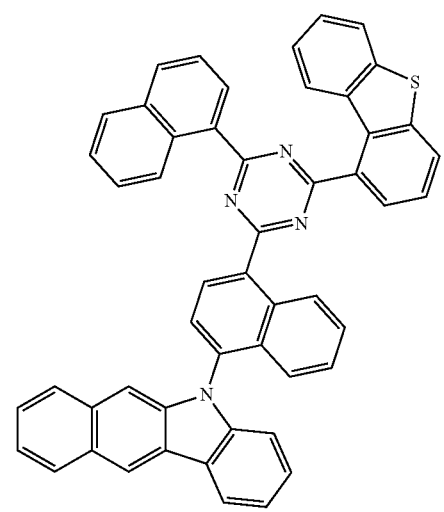
138
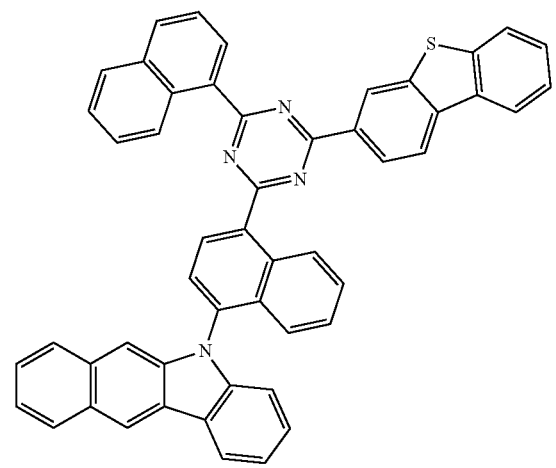
139
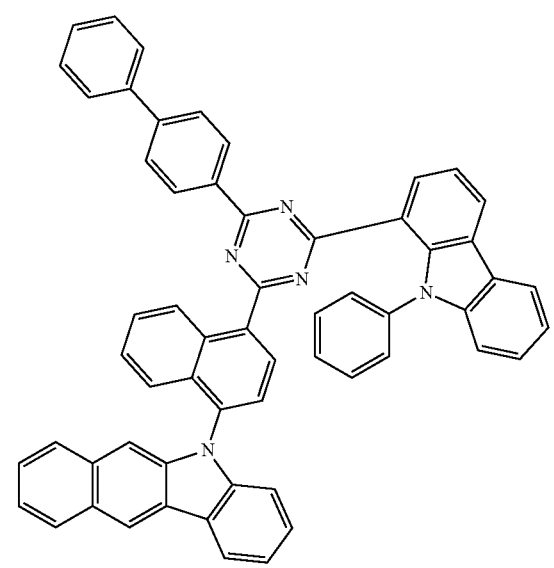
140
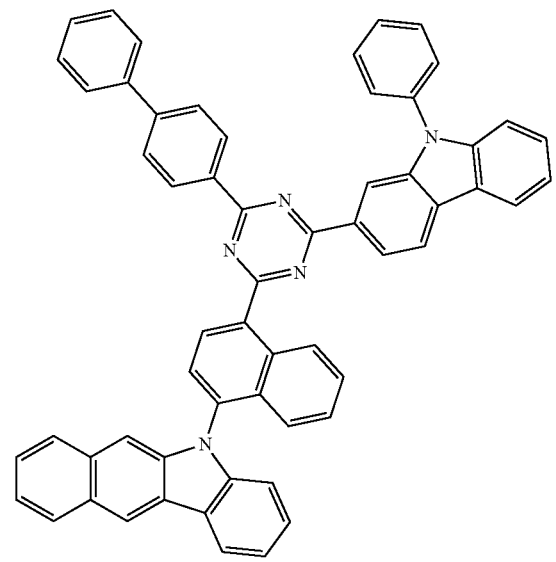

141
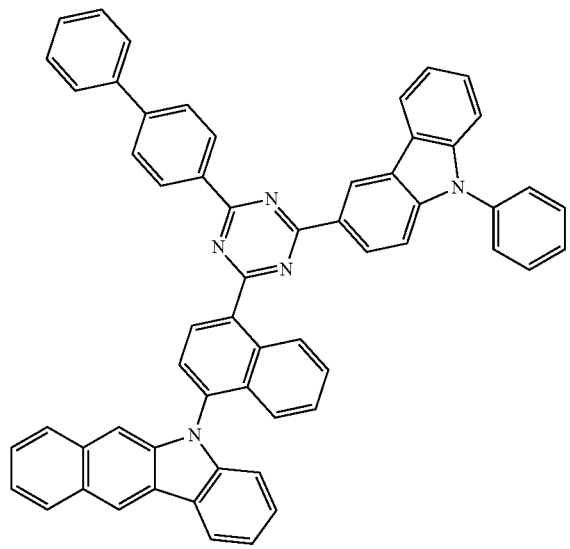
142
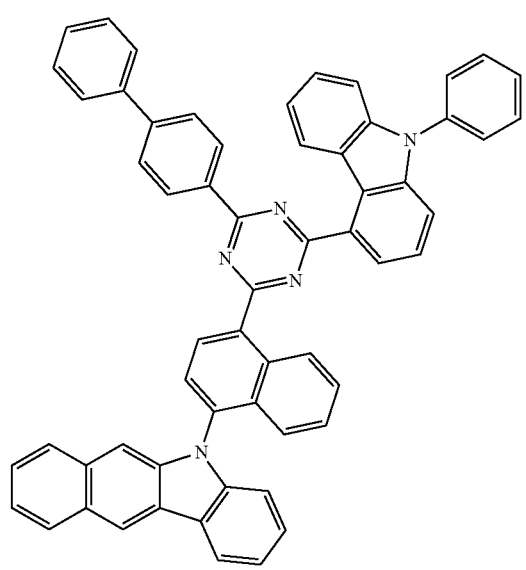
143
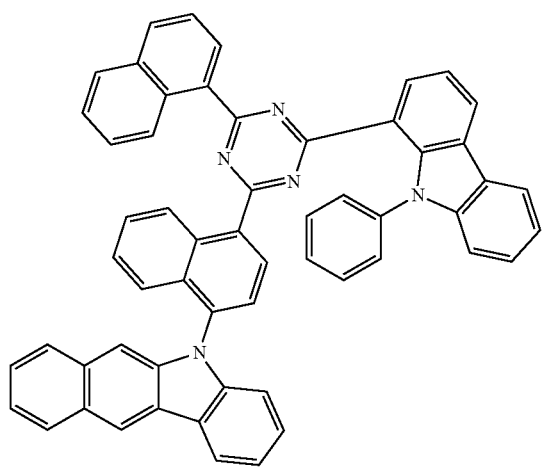
144
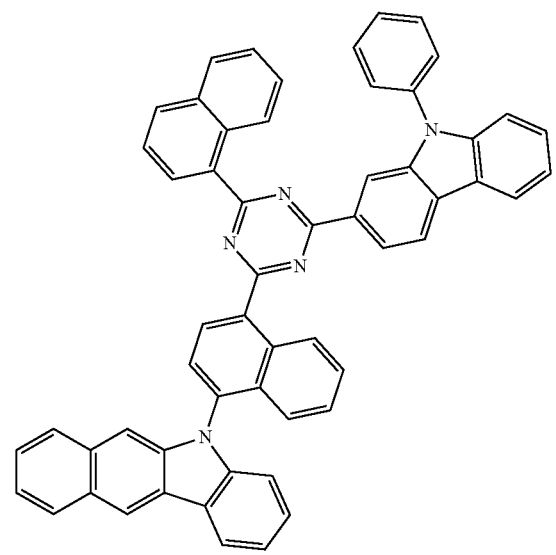
145
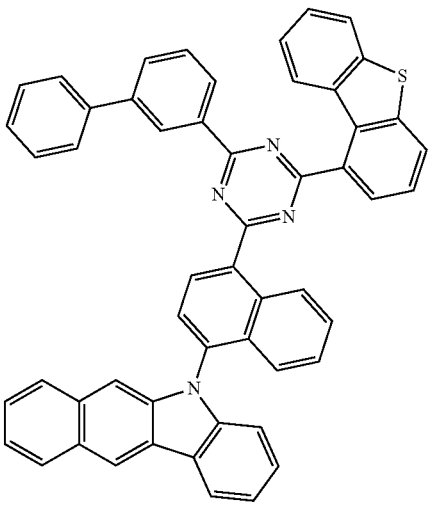
146
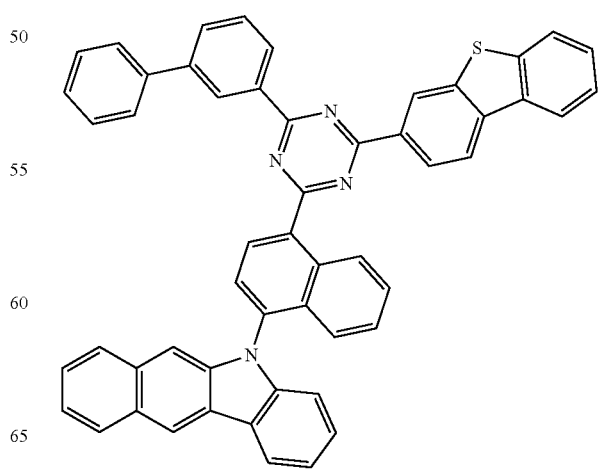

-continued
147
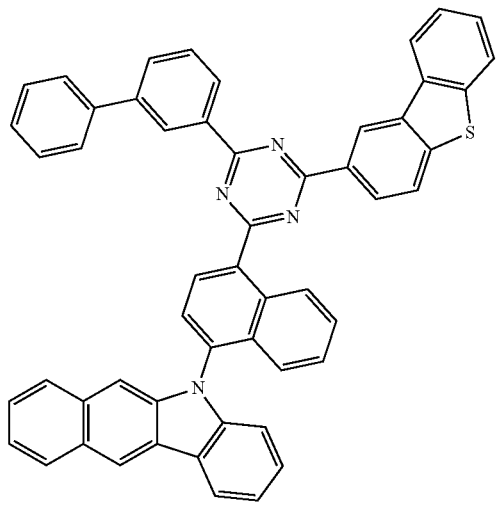
148
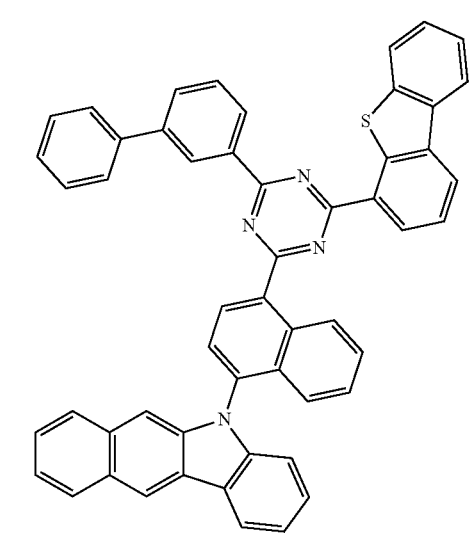
149
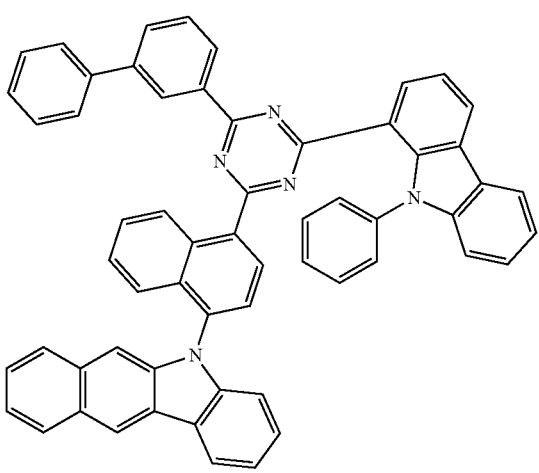
-continued
150
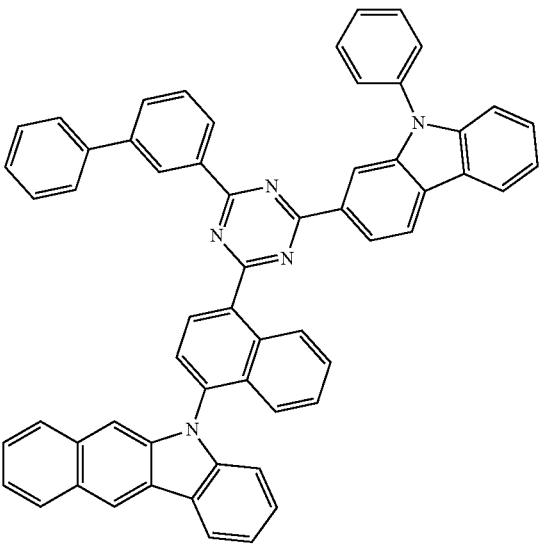
151
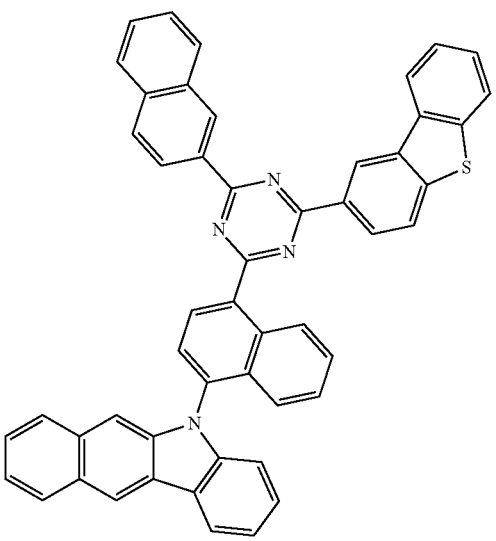
152
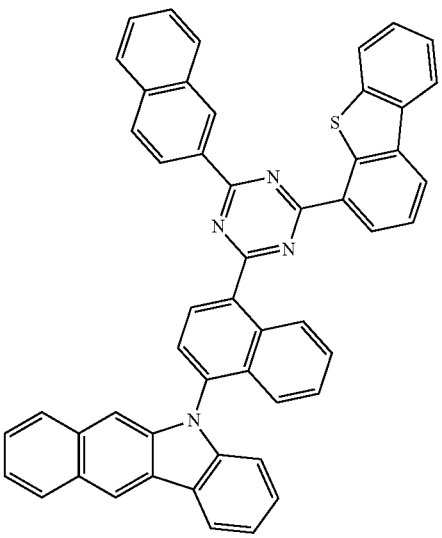

153
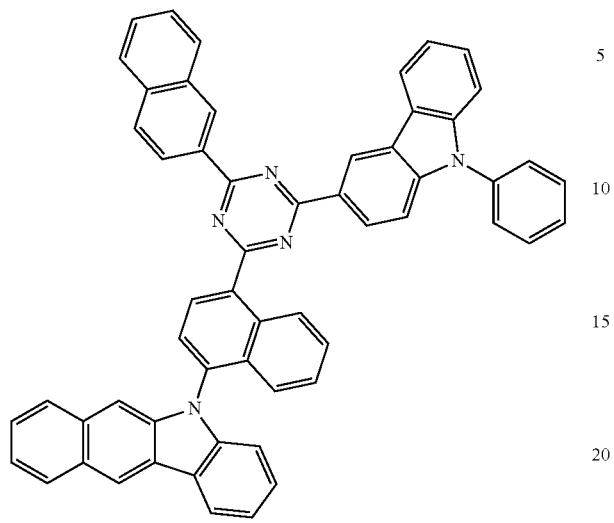
154
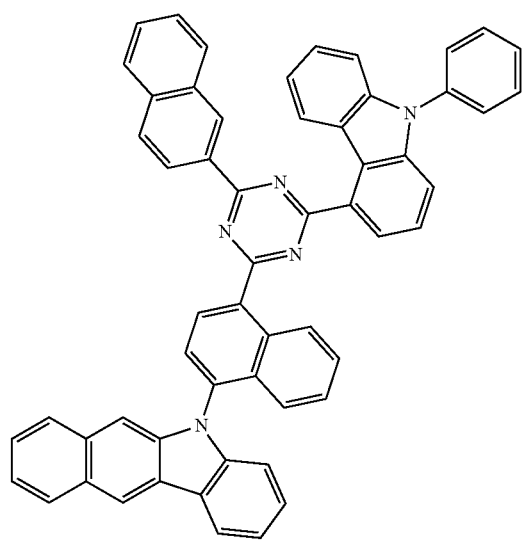
155
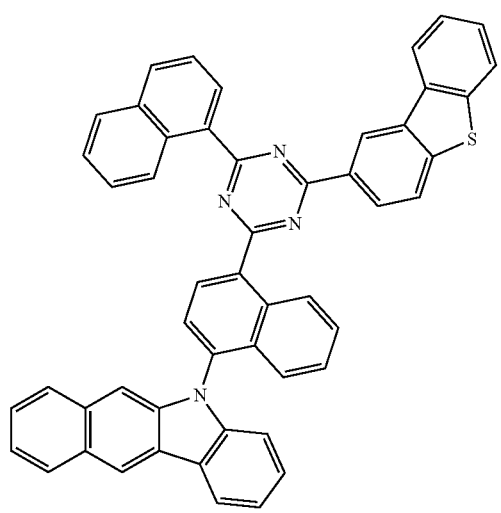
156
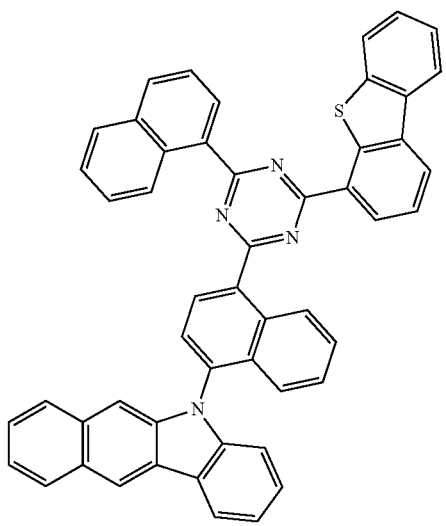
157
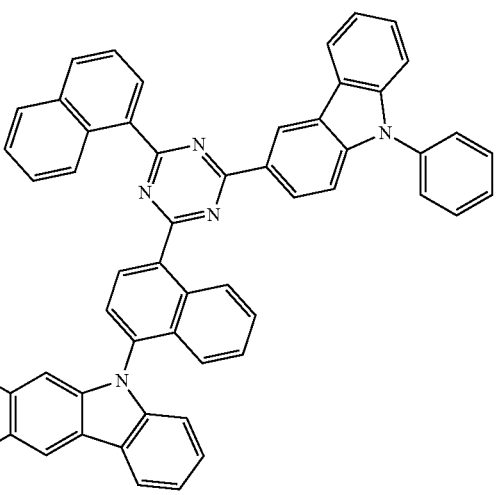
158
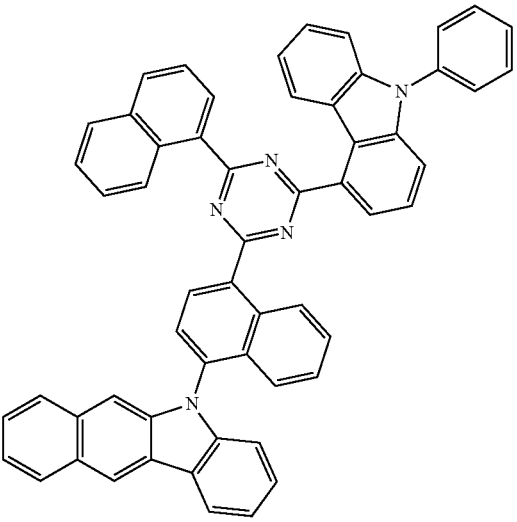

159
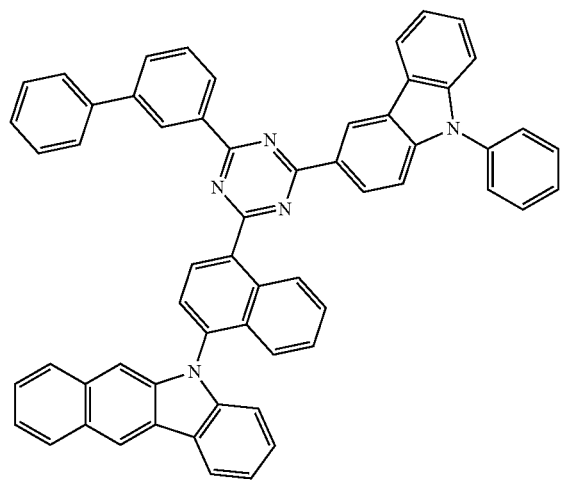
162
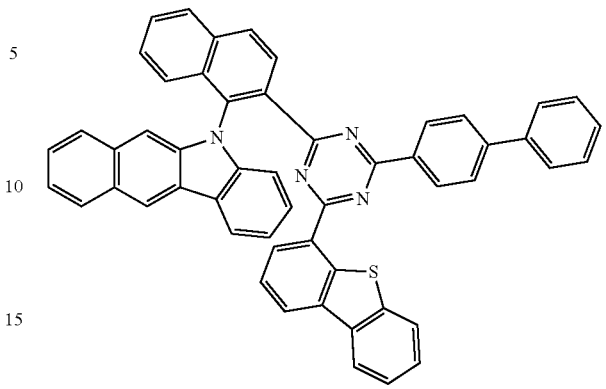
160
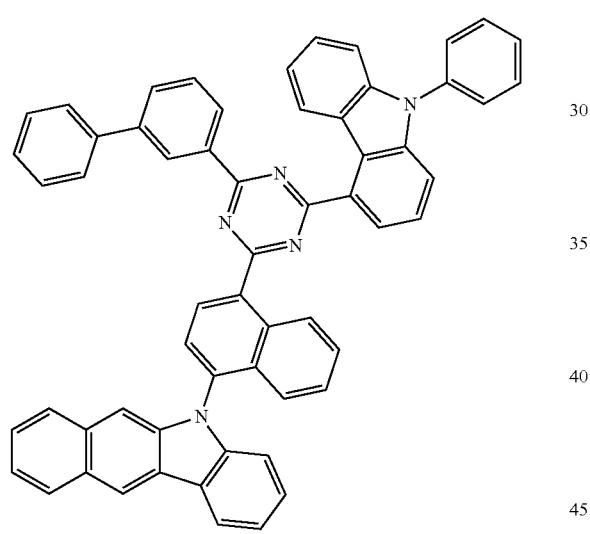
163
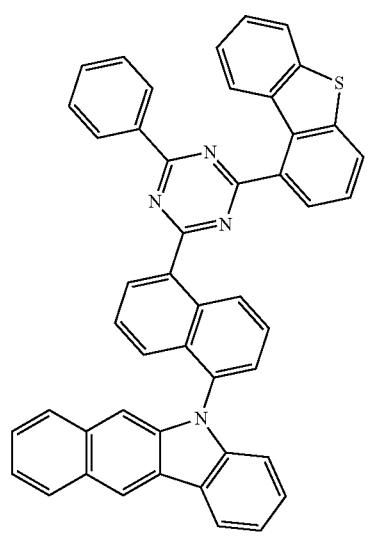
161
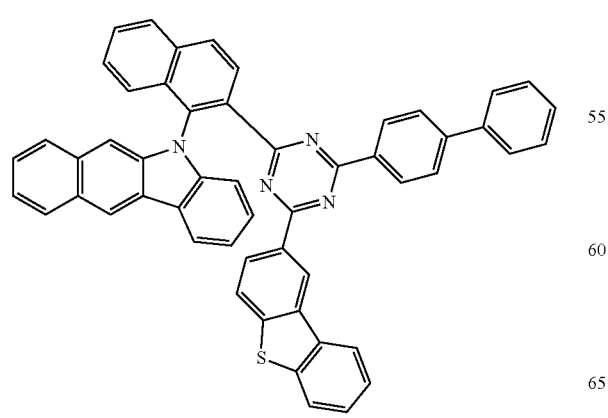
164
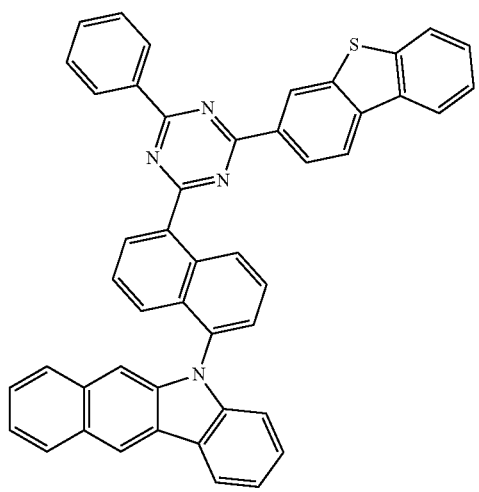

165
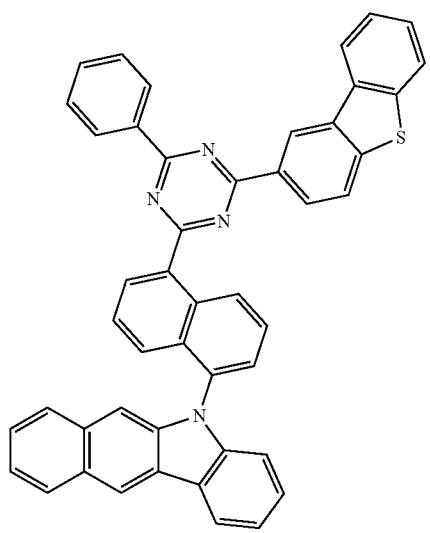
166
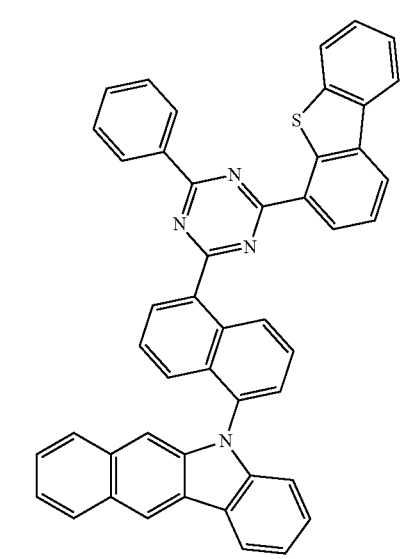
167
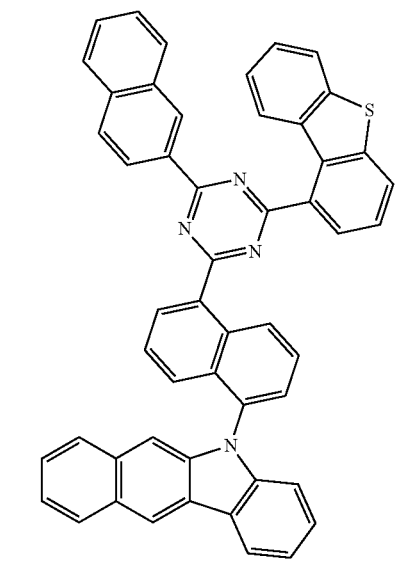
168
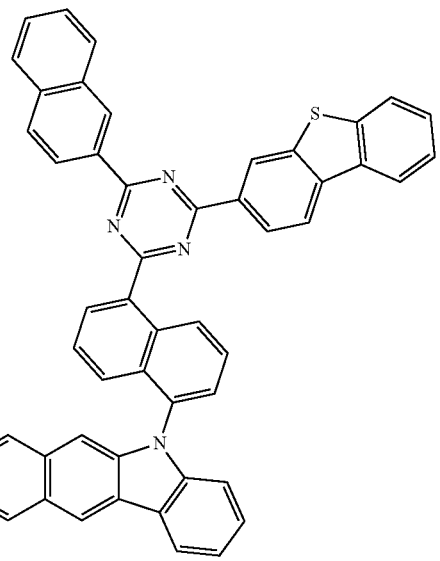
169
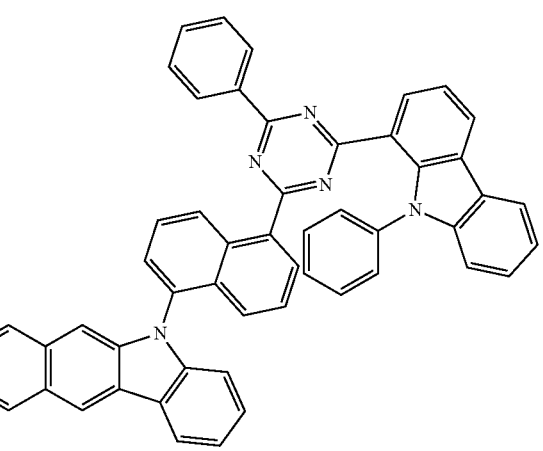
170
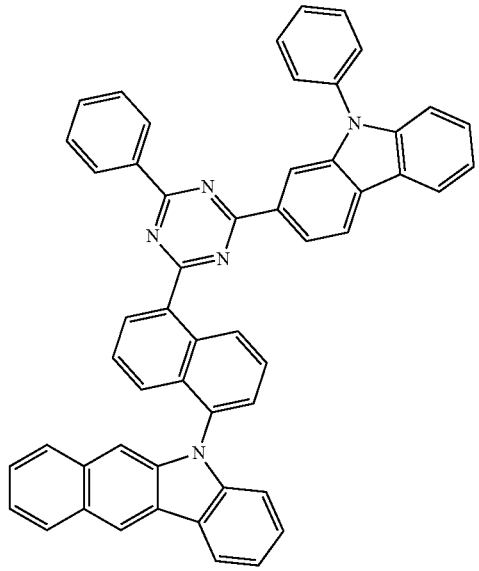

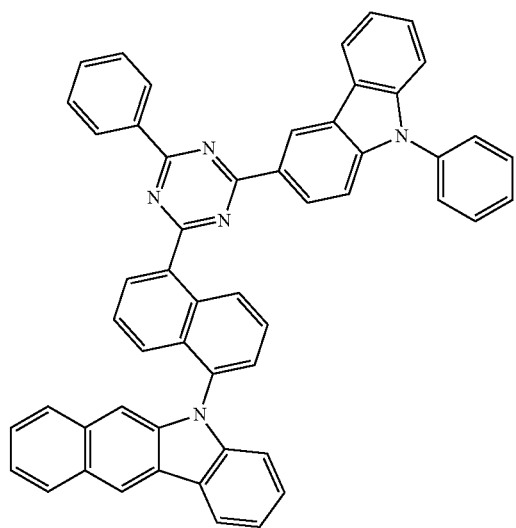
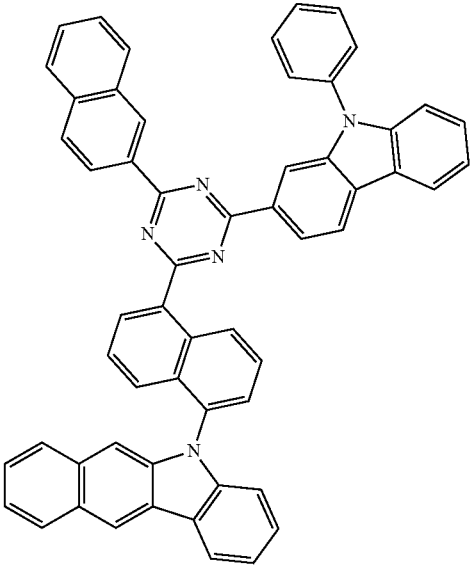
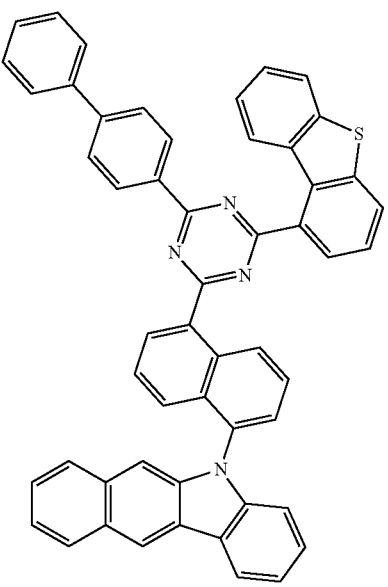

176
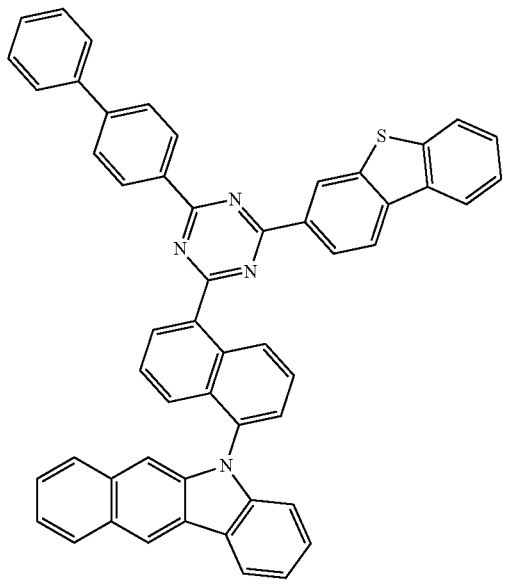
177
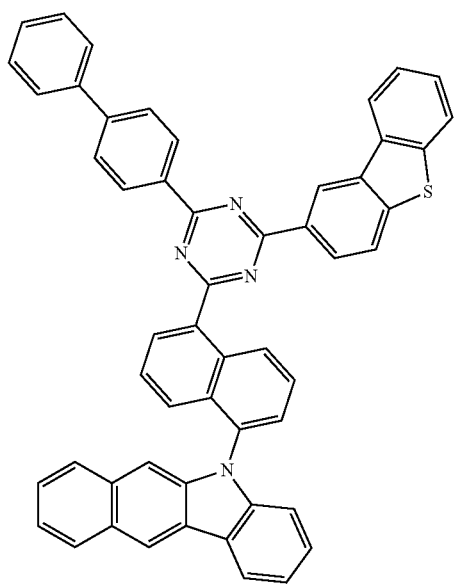
178
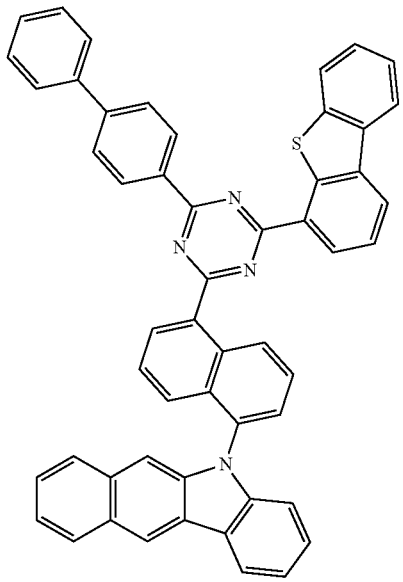
179
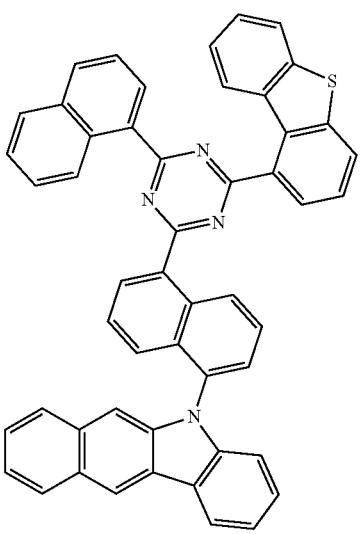
180
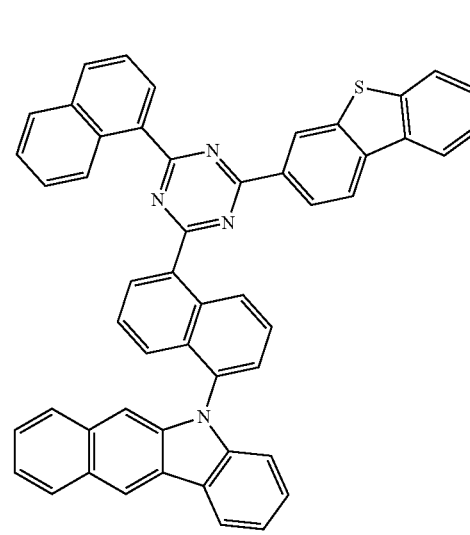

181
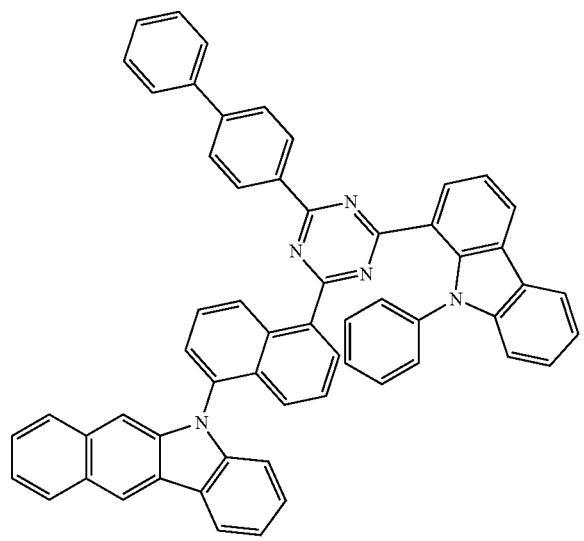
182
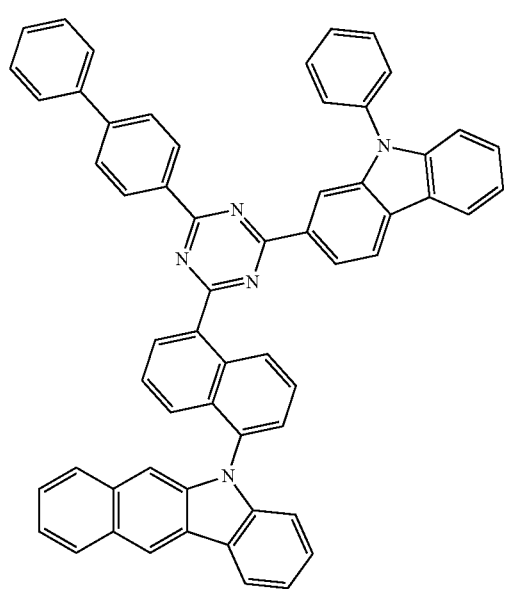
183
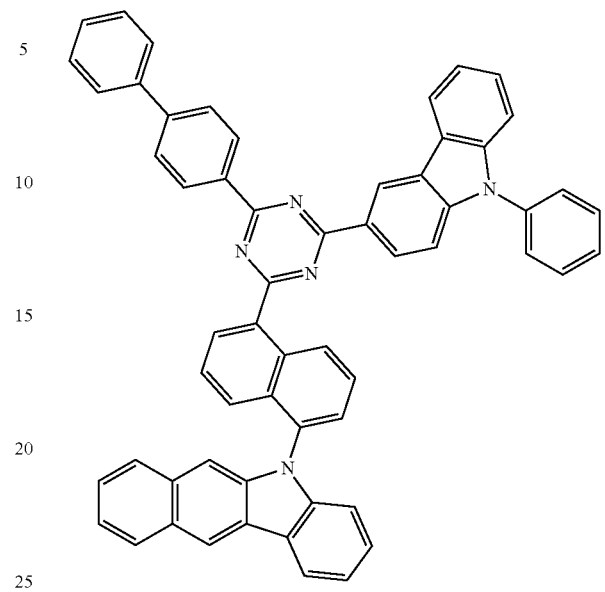
184
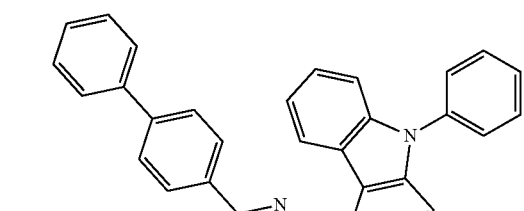
185
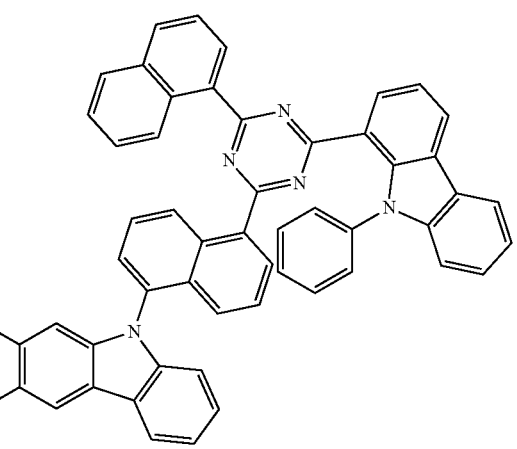

186
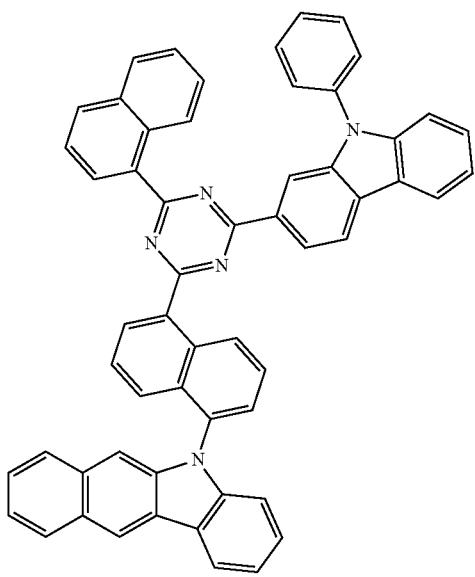
187
189
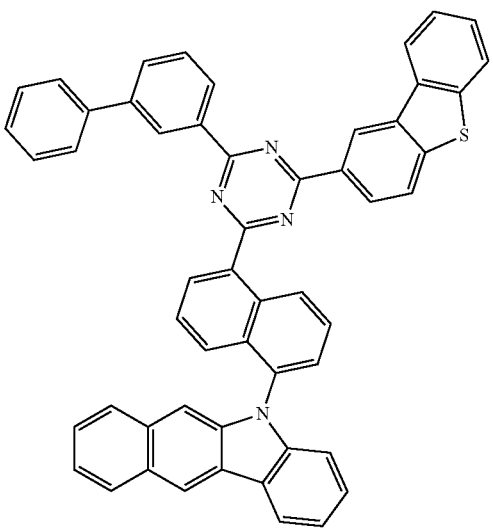
190
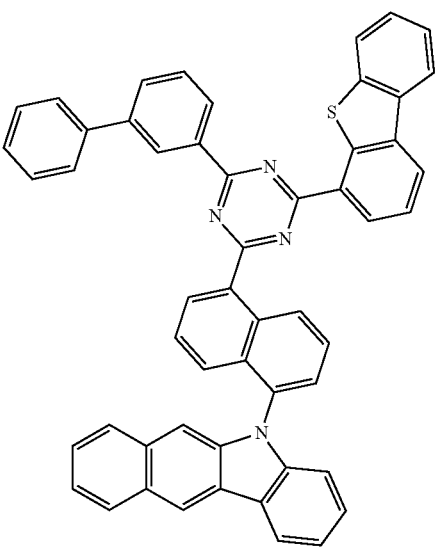
188
191
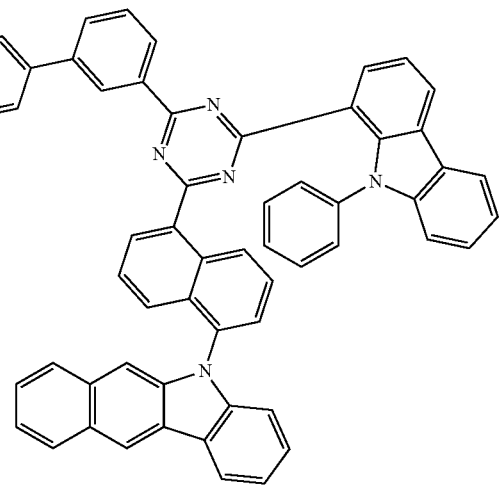

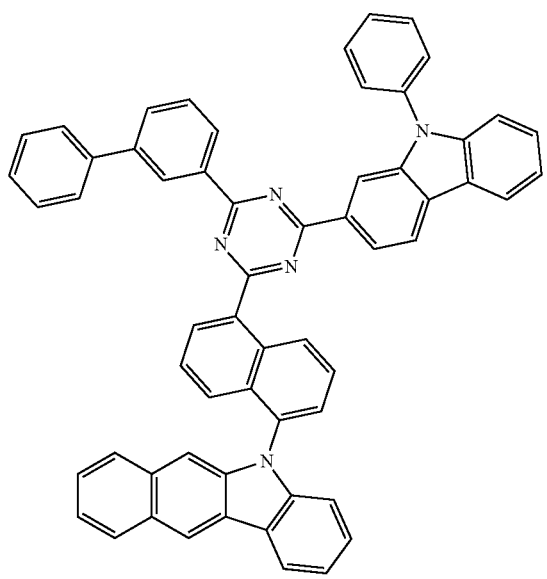
192
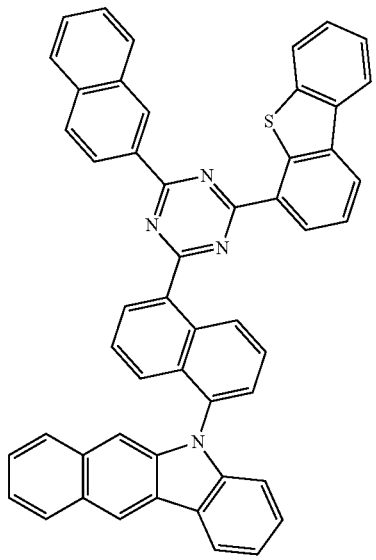
194
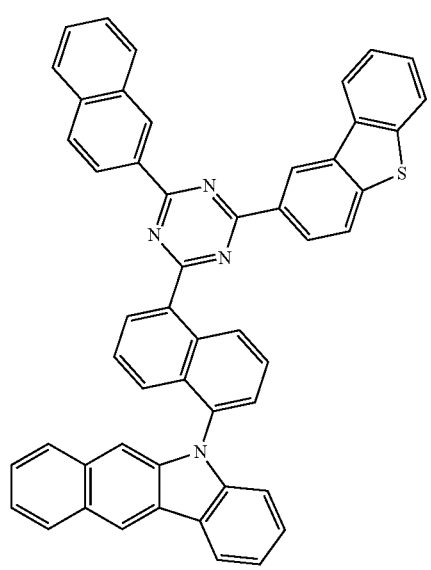
193
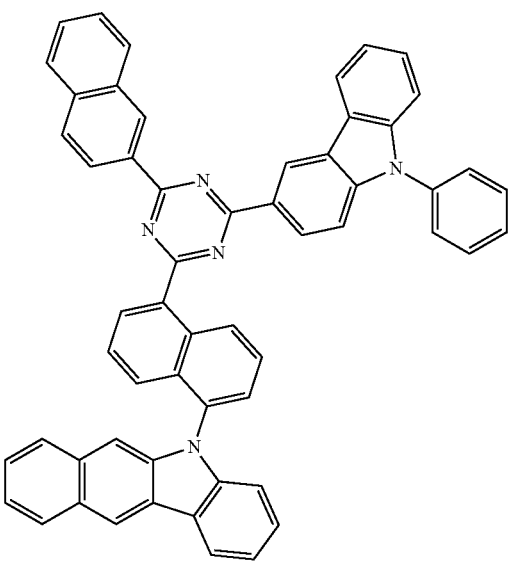
195

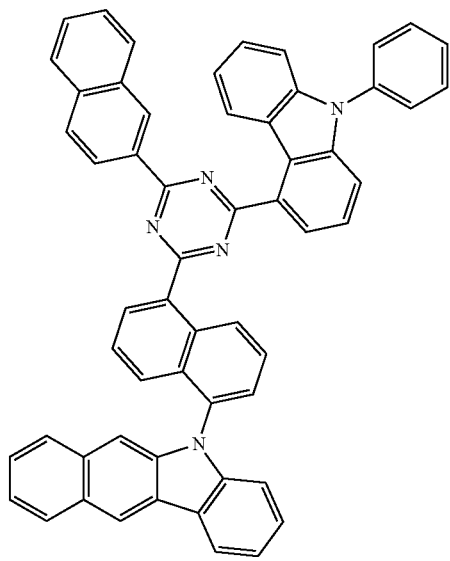
196
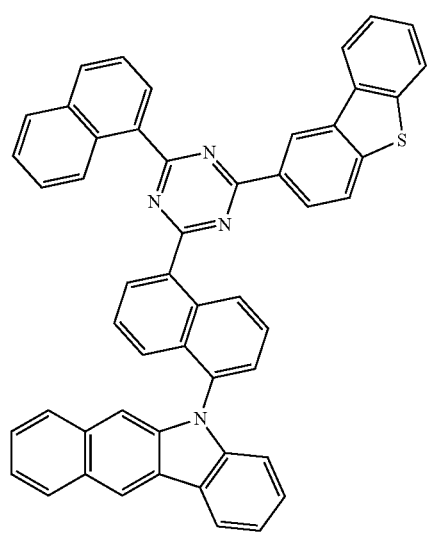
197
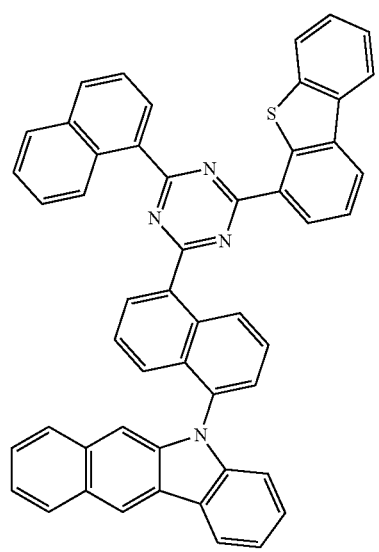
198
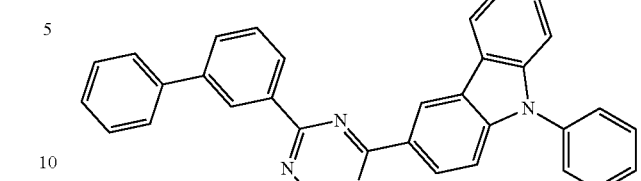
199
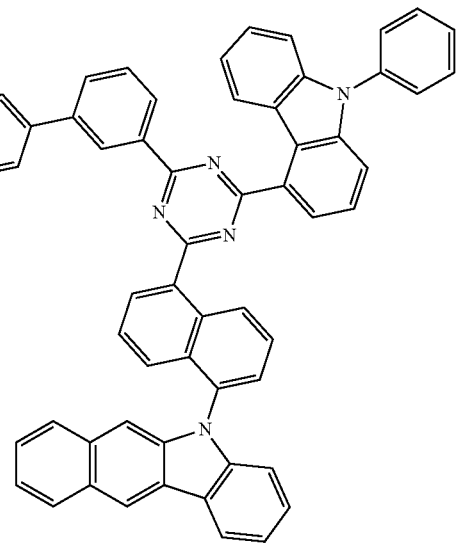
200
201

202
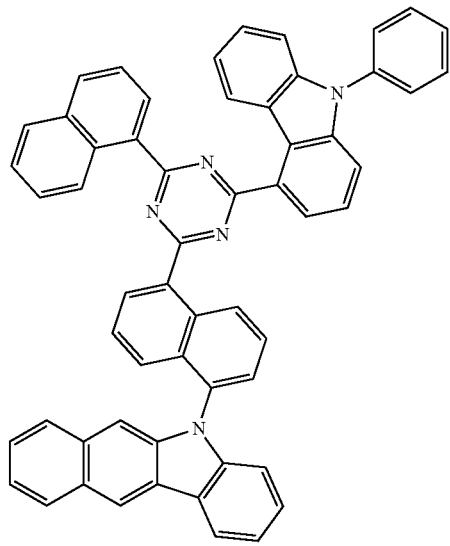
203
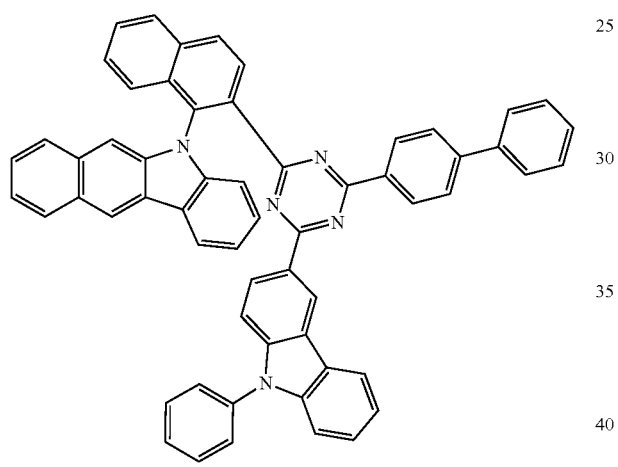
204
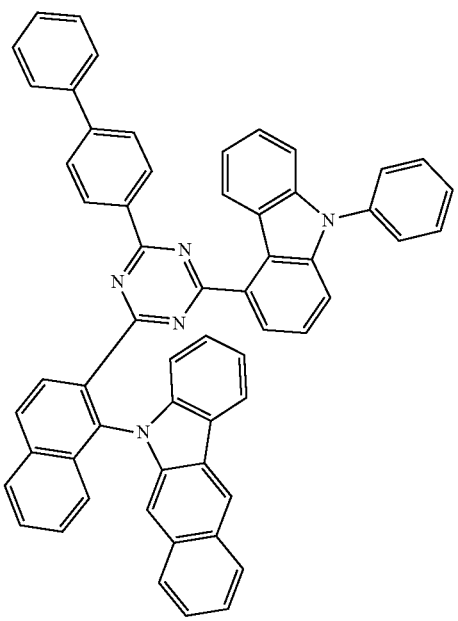
205
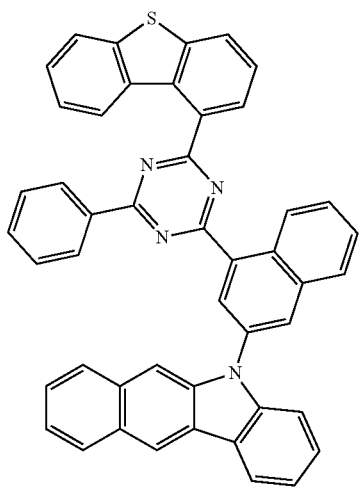
206
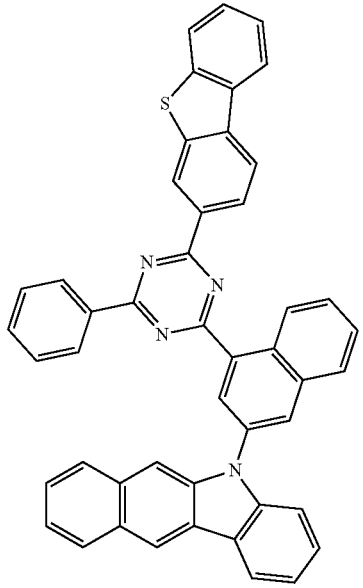
207
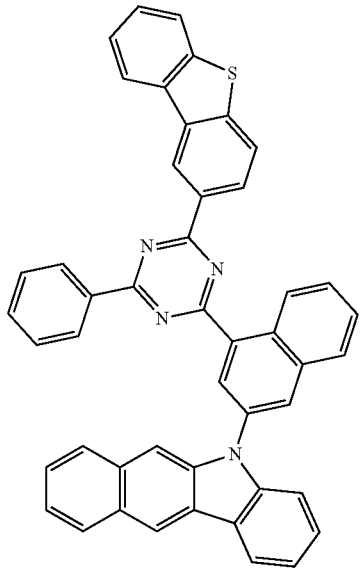

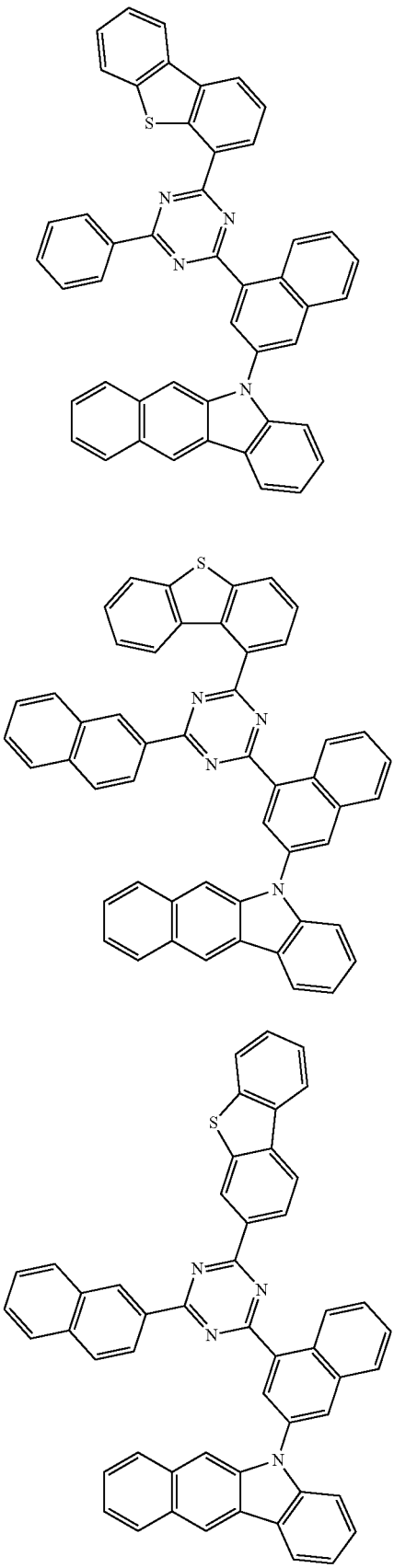
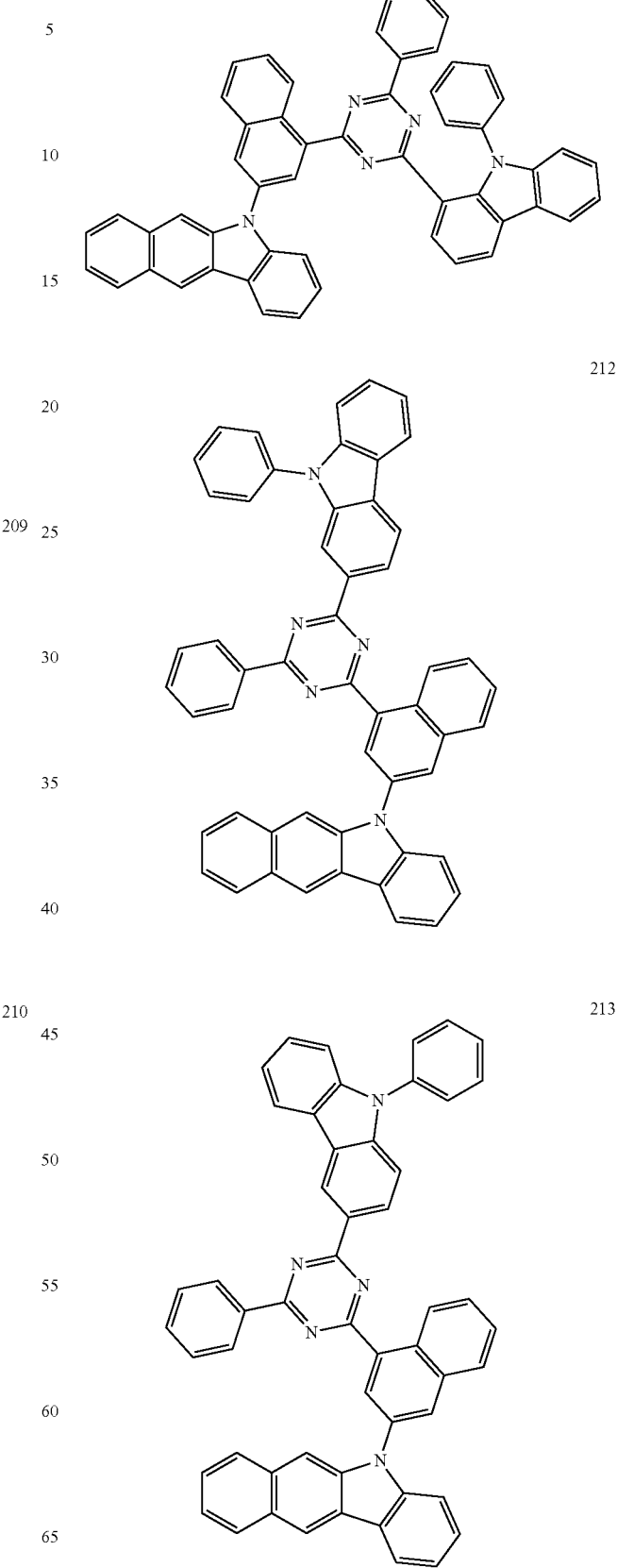

81
-continued
214
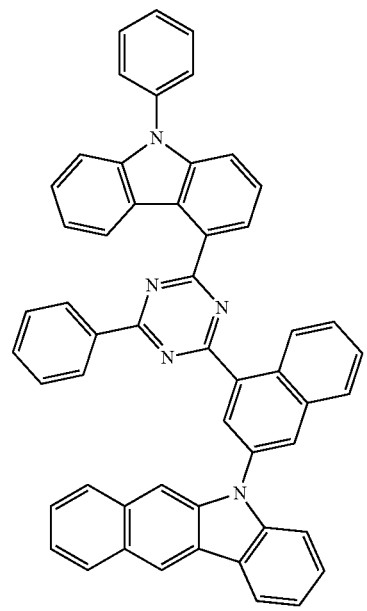
215
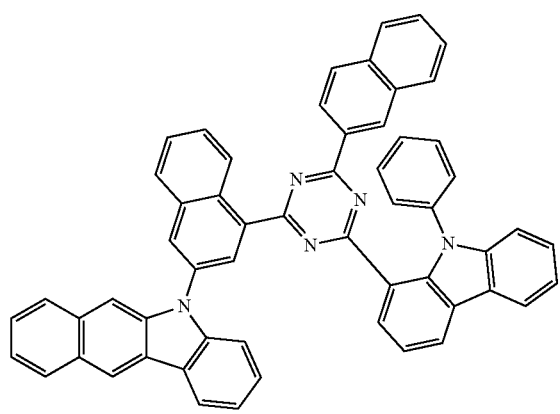
216
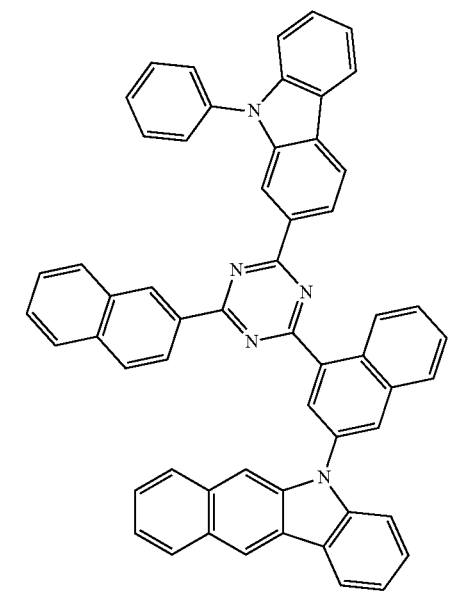
82
-continued
217
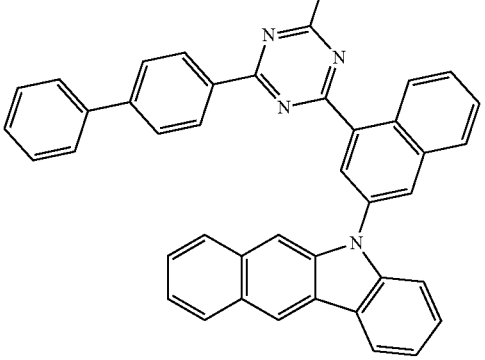
218
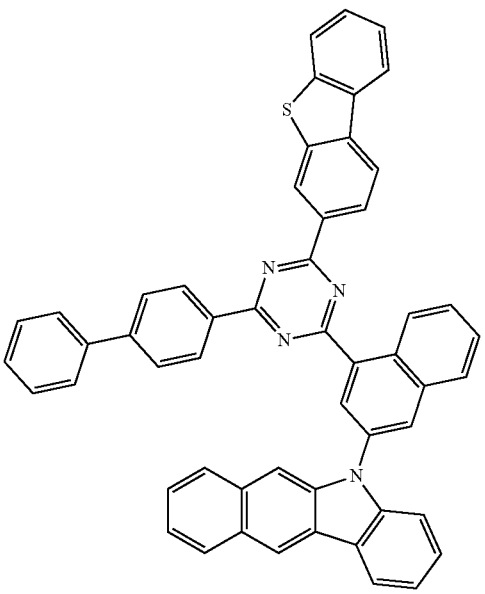
219
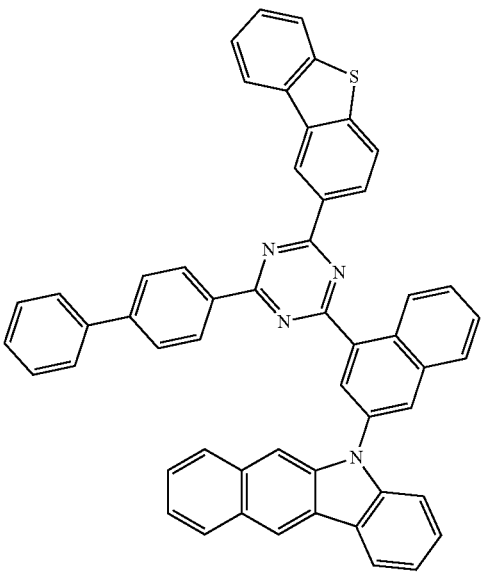

220
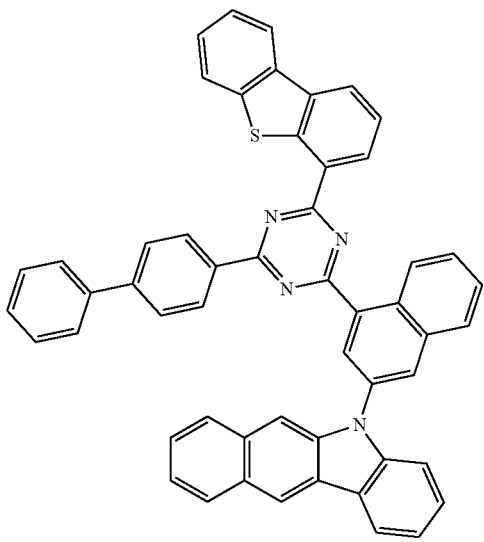
221
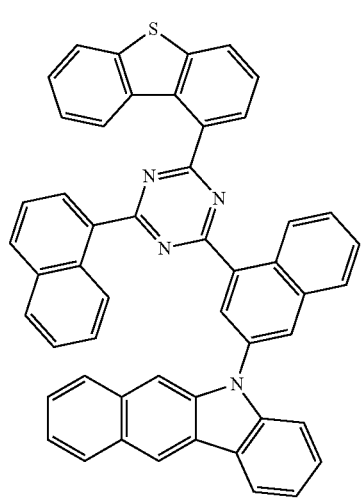
222
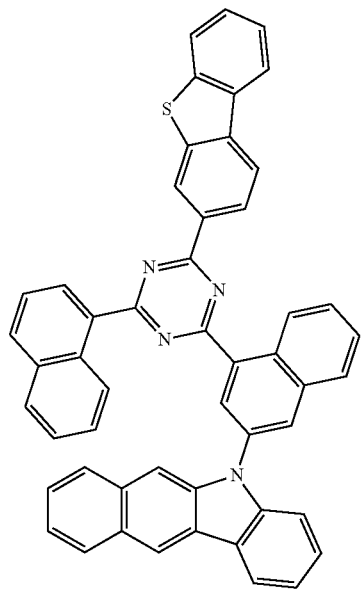
223
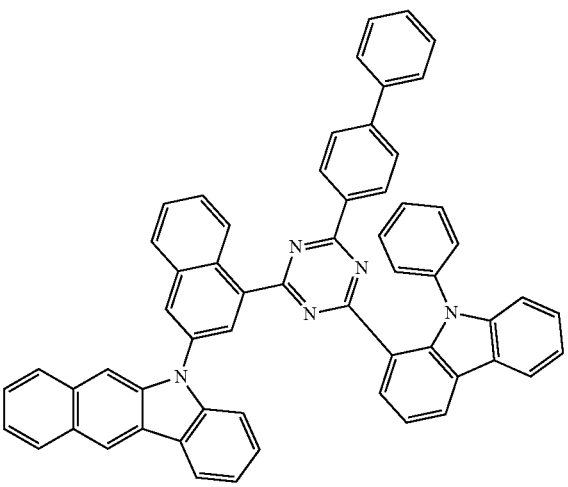
224
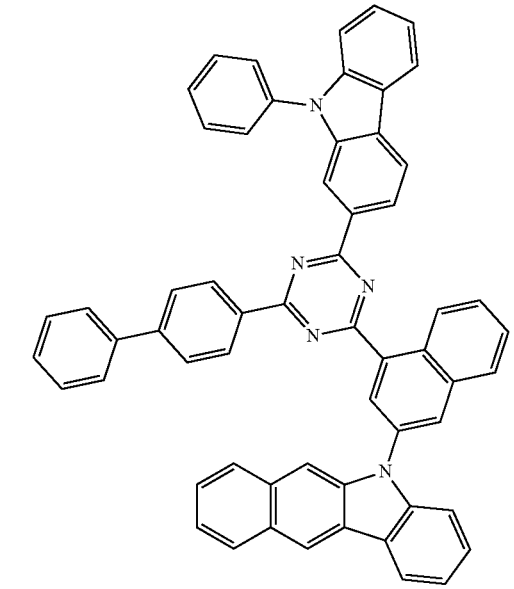

225
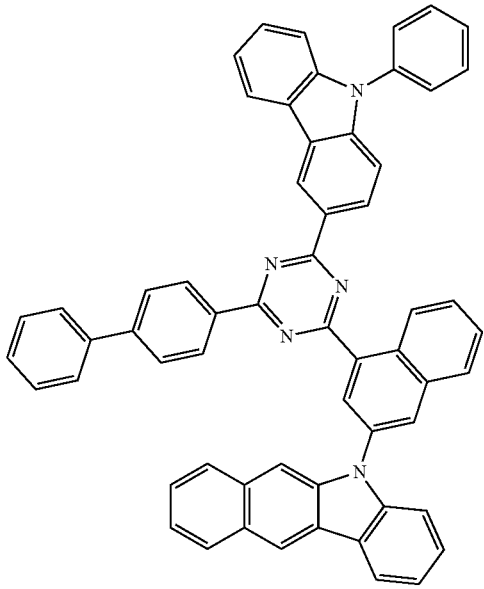
226
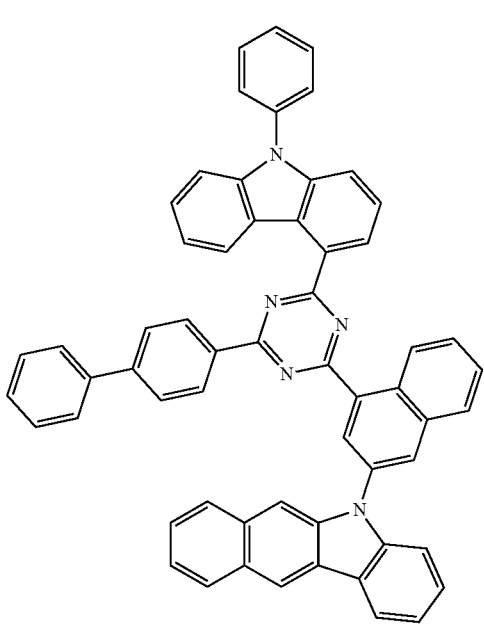
227
228
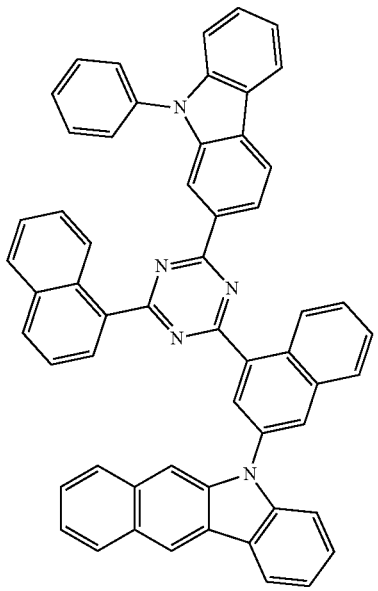
229
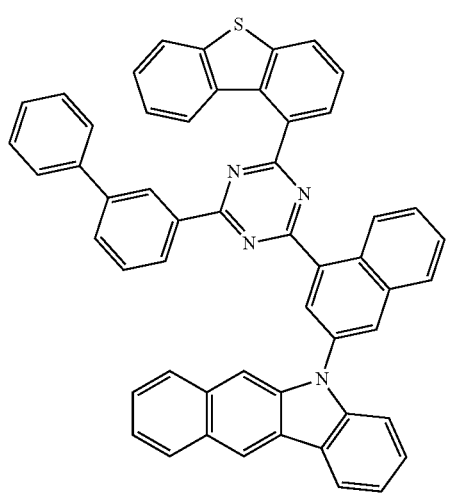
230
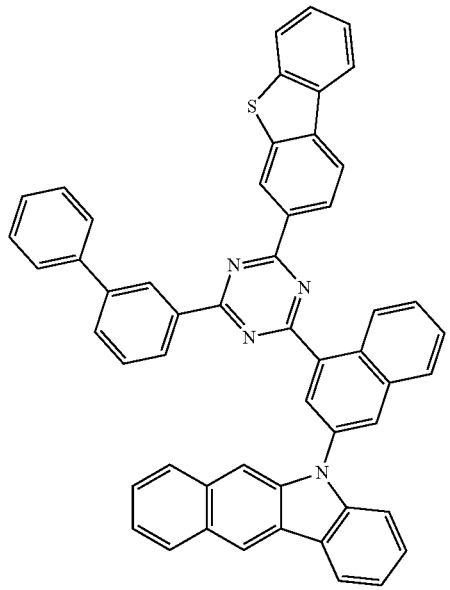

231
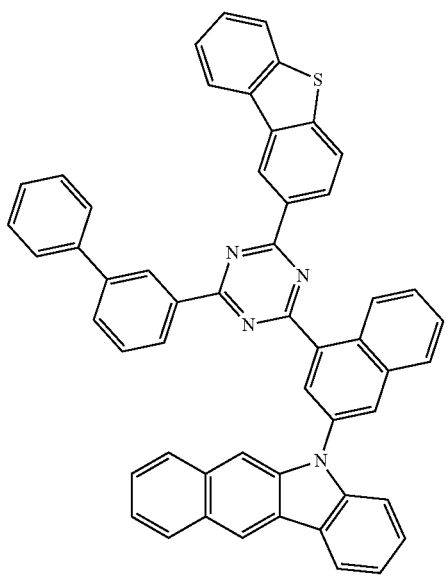
232
234
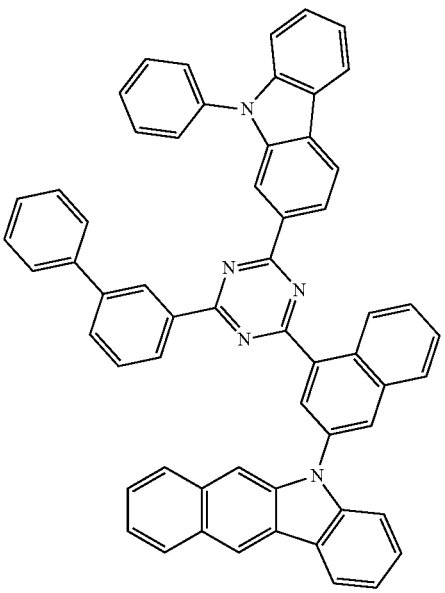
235
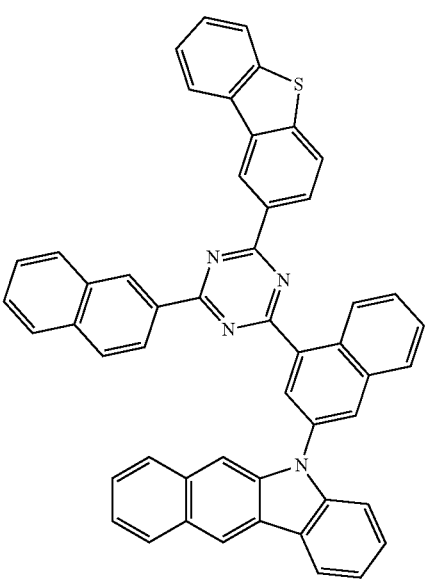
233

236
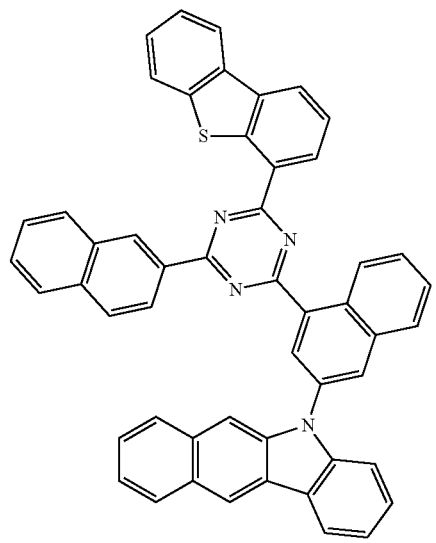
237
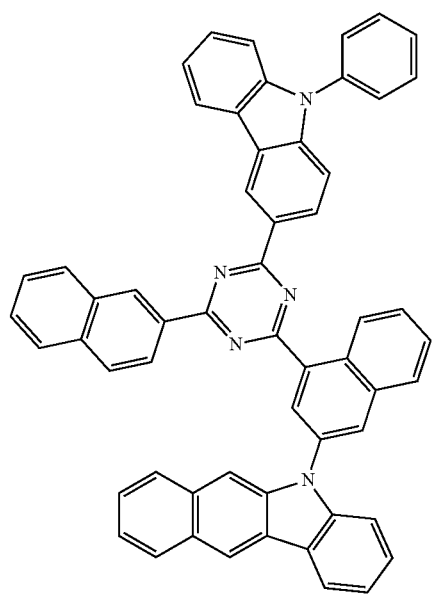
238
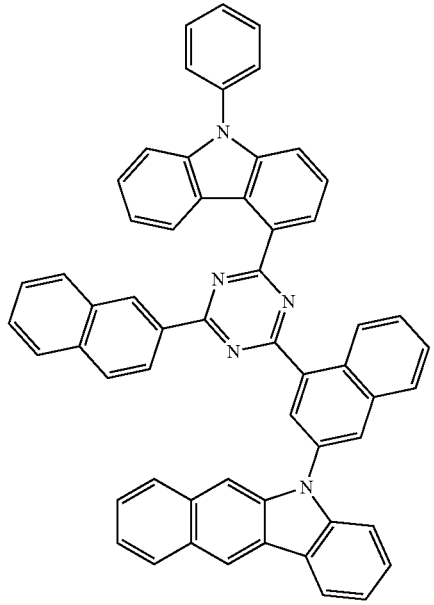
239
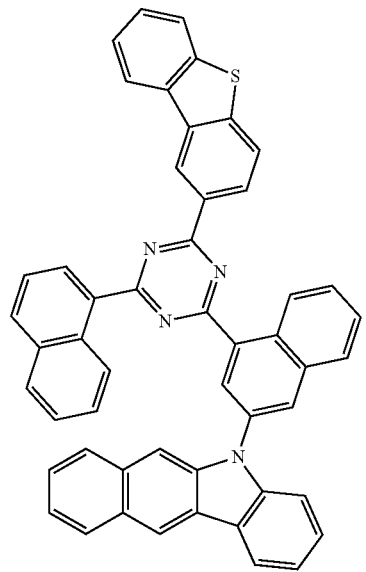

240
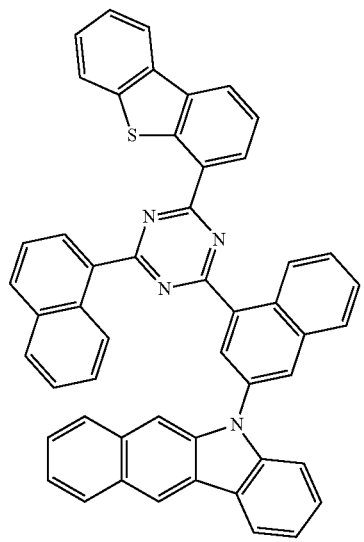
241
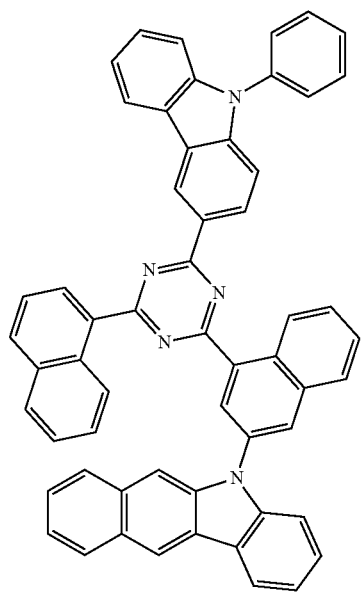
242
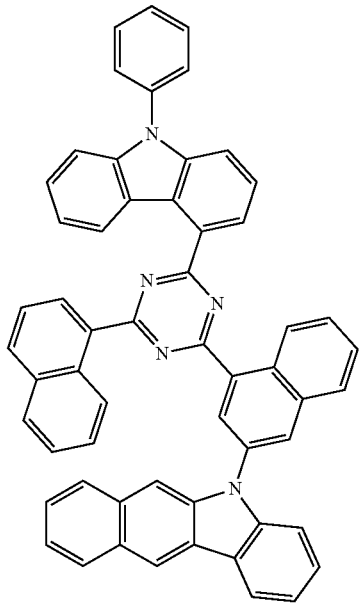
243
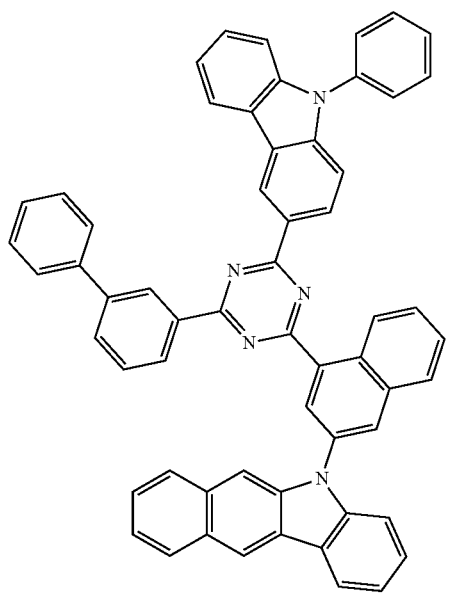

244
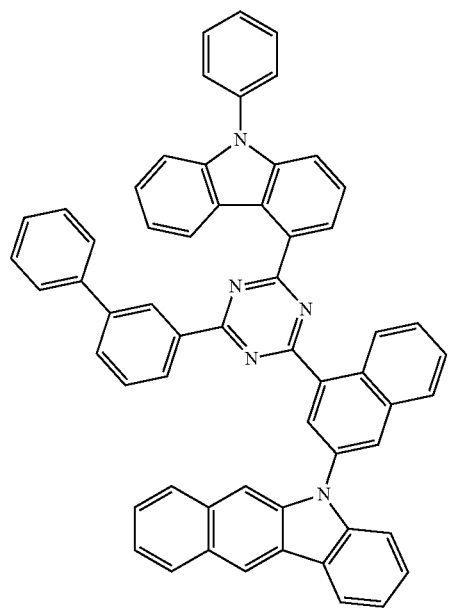
245
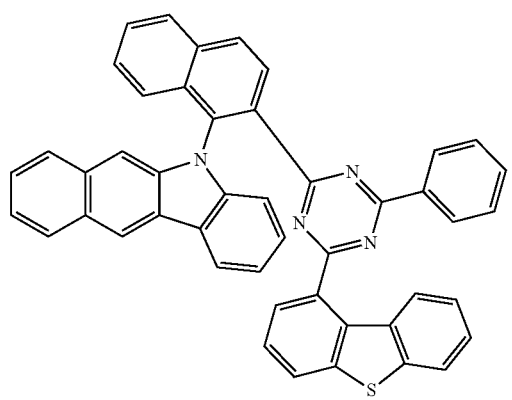
246
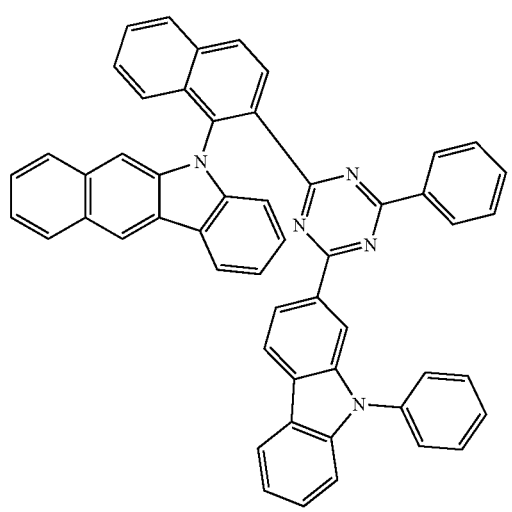
247
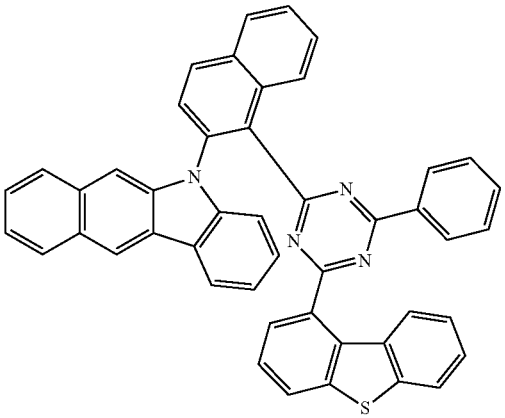
248
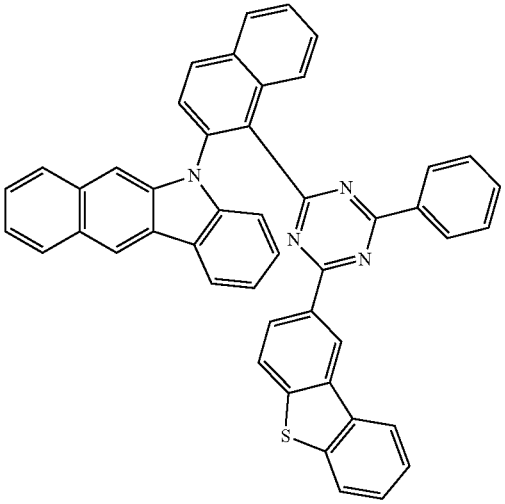
249

250
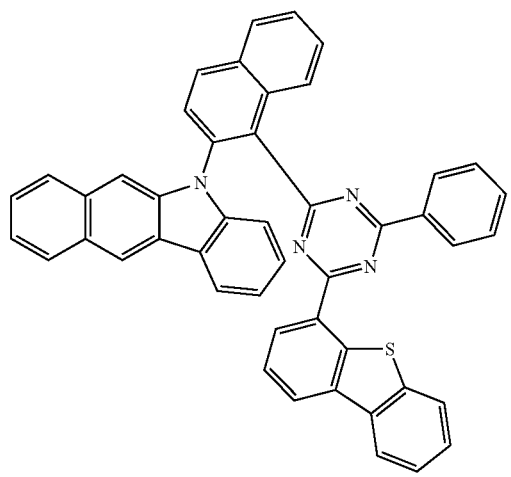
251
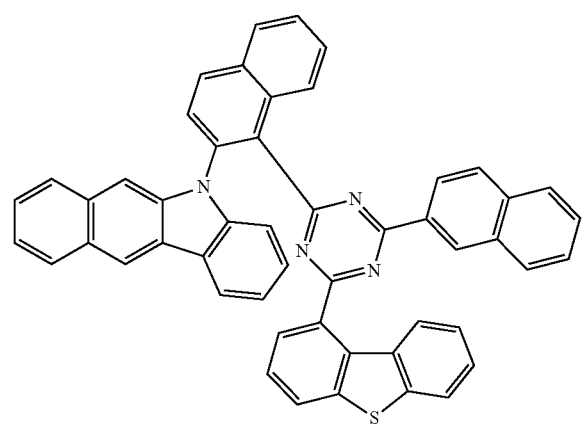
252
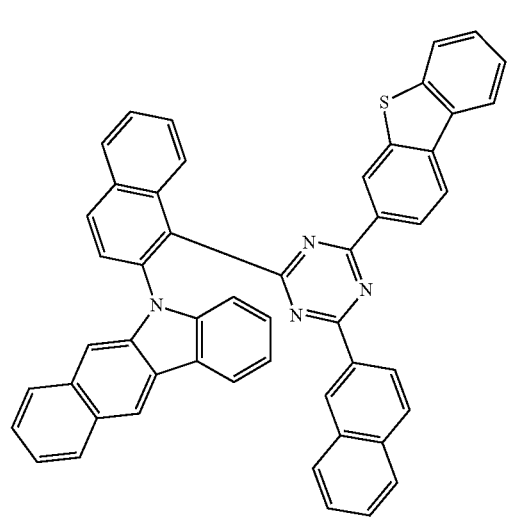
253
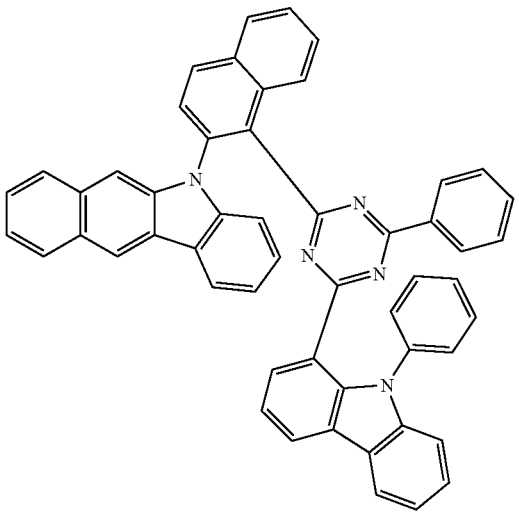
254
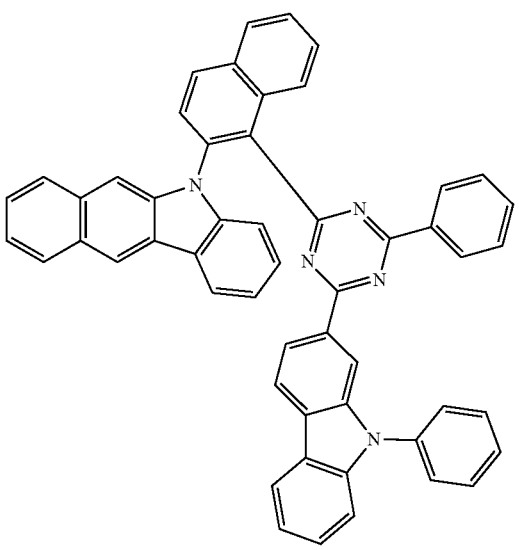
255
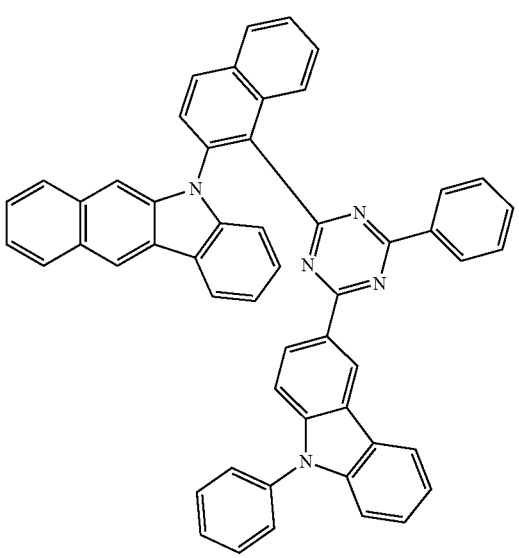

256
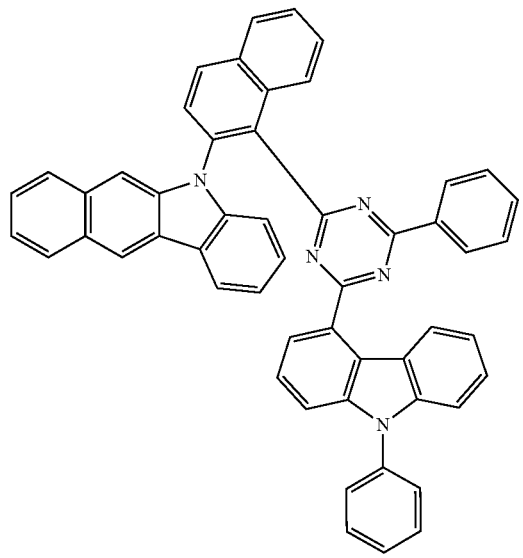
257
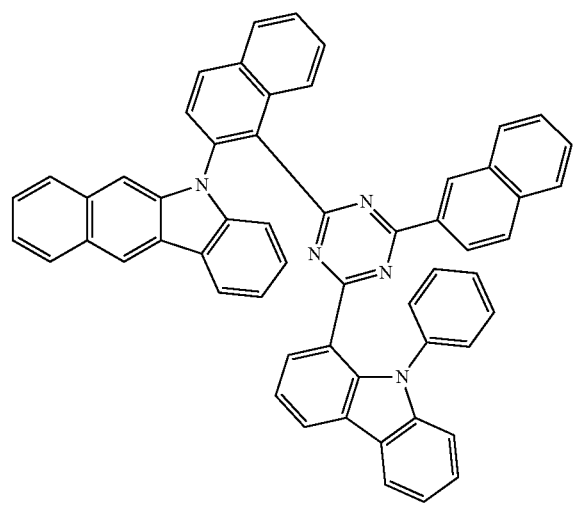
258
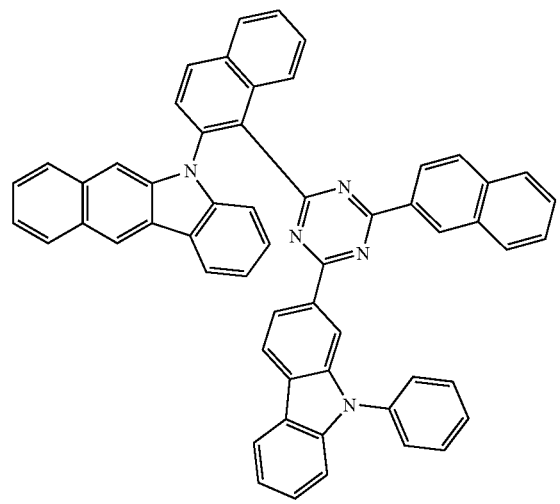
259
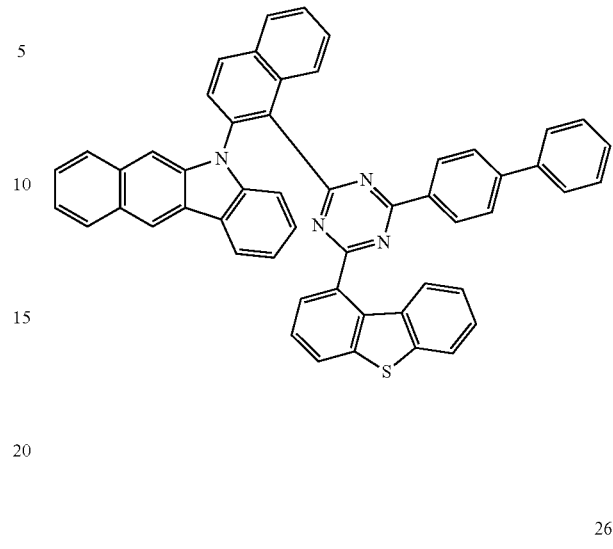
260
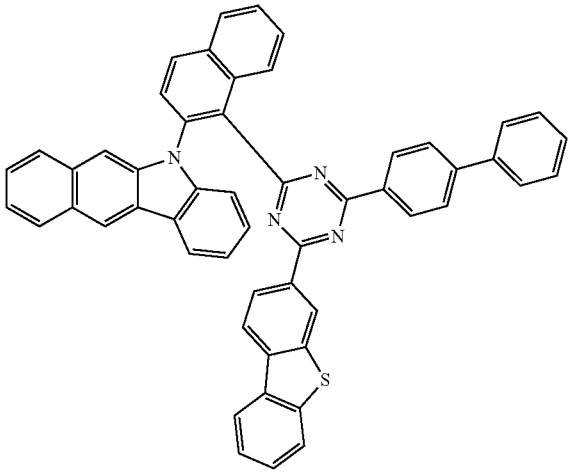
261

262
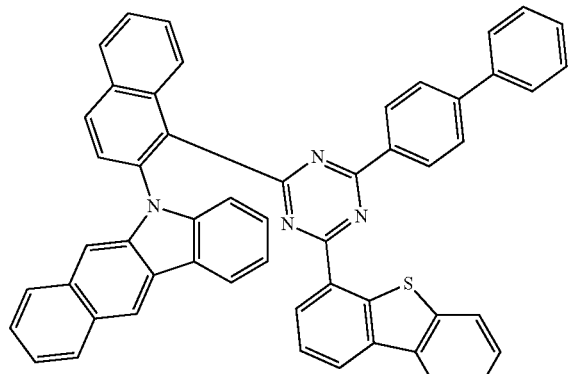
263
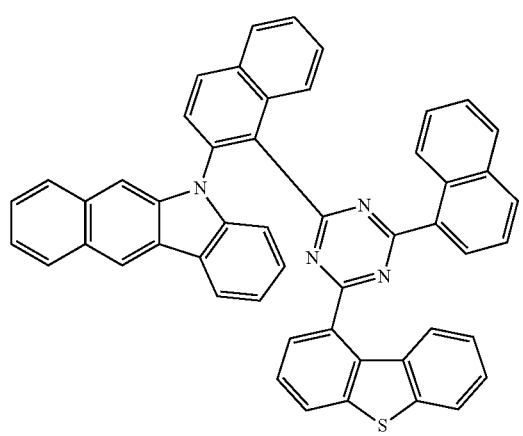
264
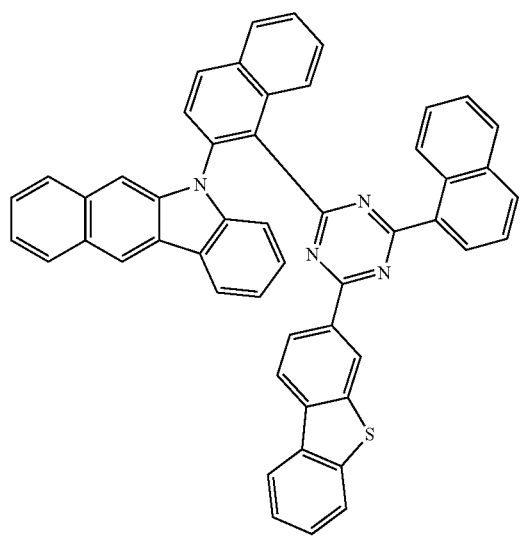
265
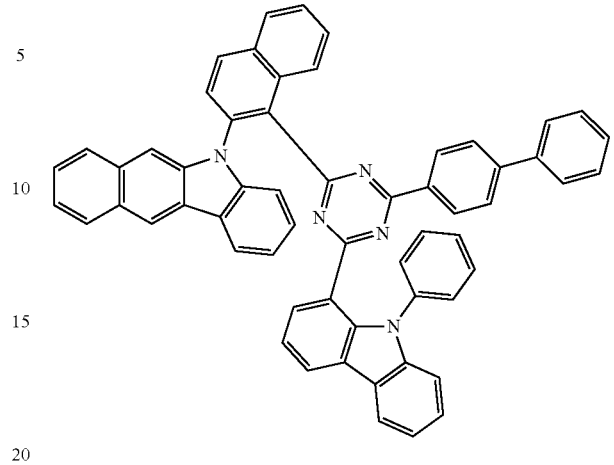
266
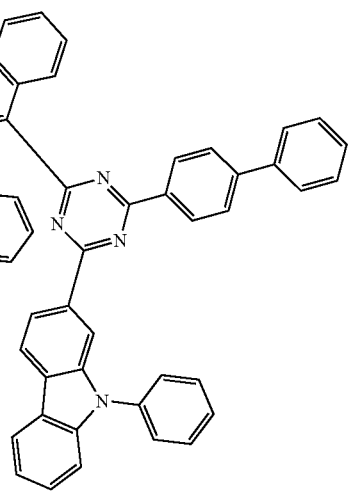
267

101
-continued
268
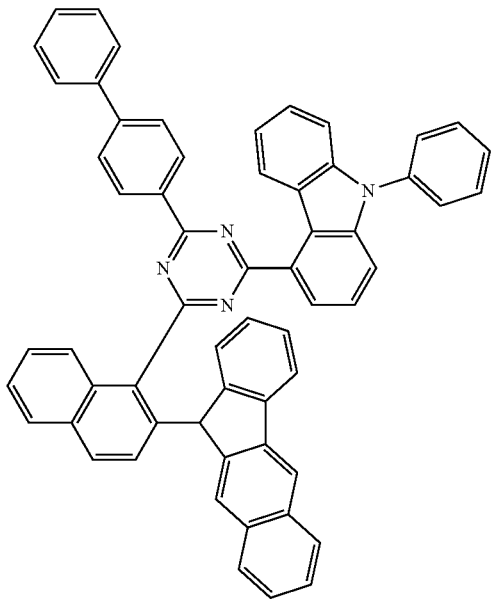
269
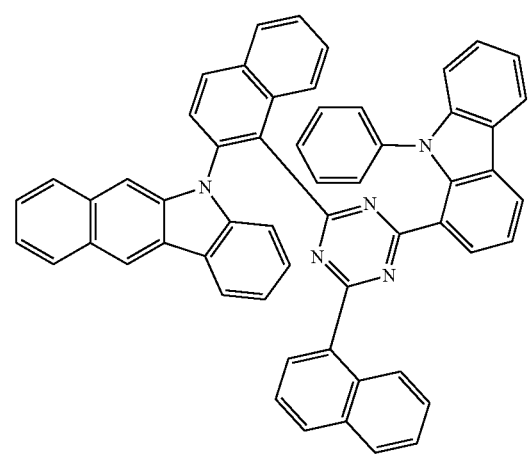
270
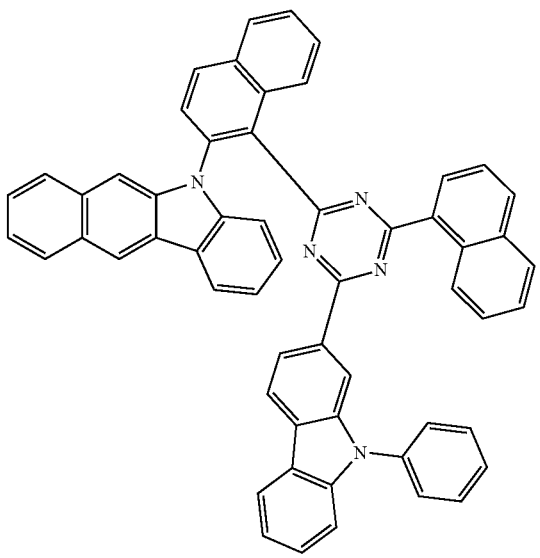
102
-continued
271
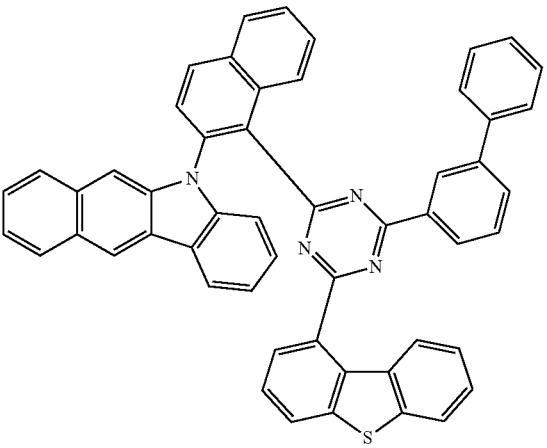
272
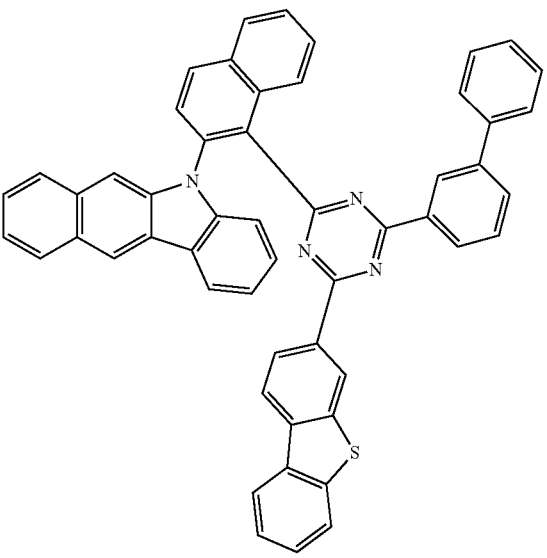
273
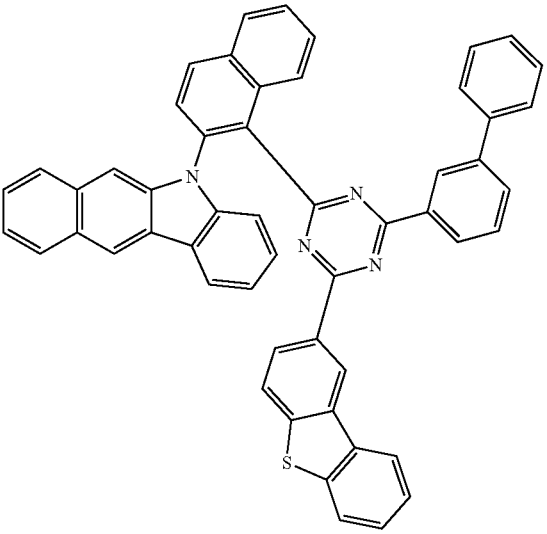

274
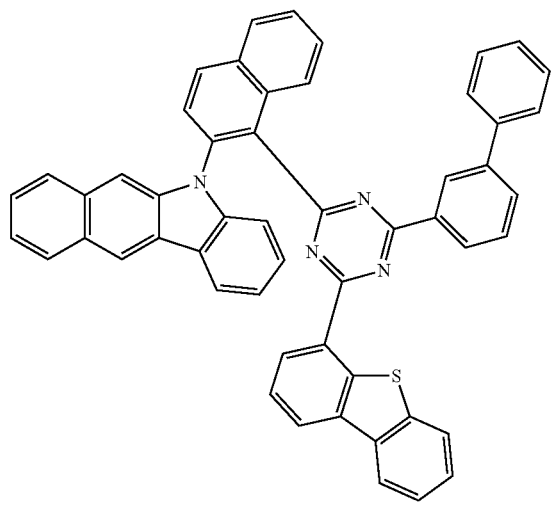
275
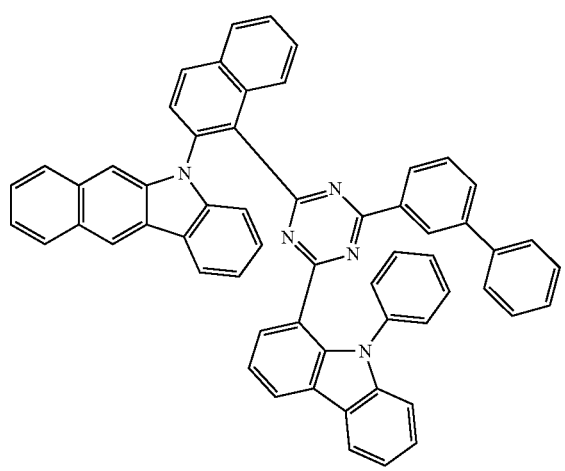
276
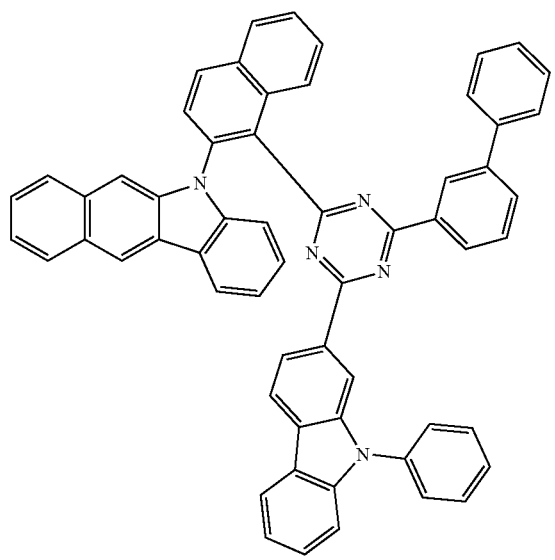
277
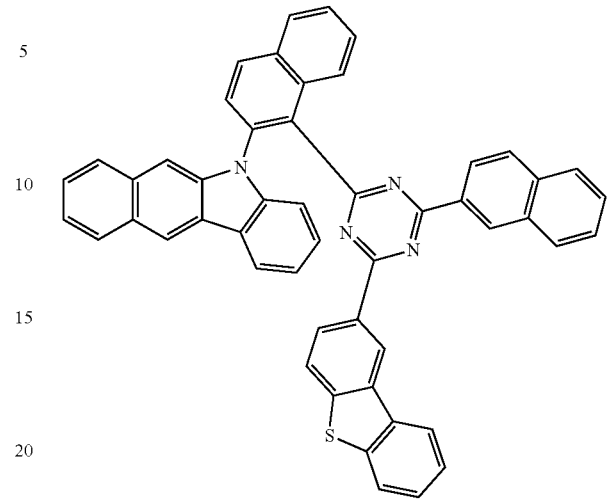
278
279
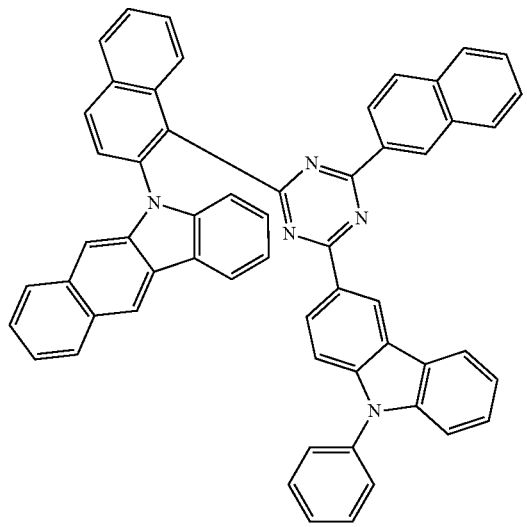

280
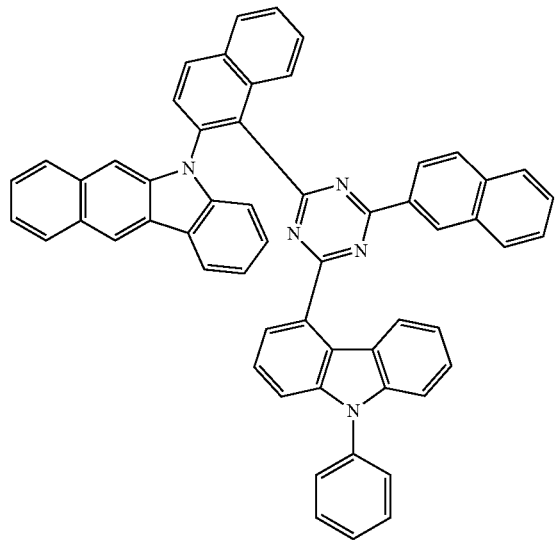
281
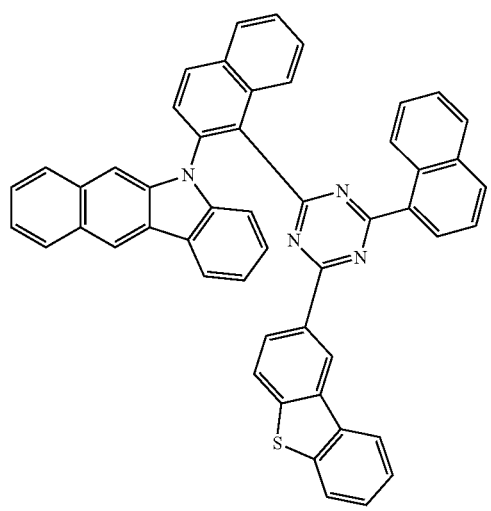
282
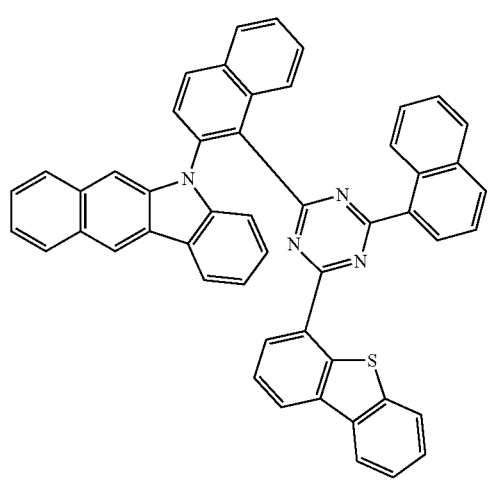
283
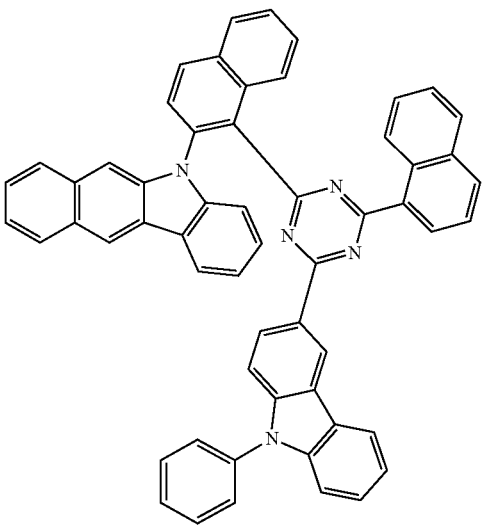
284
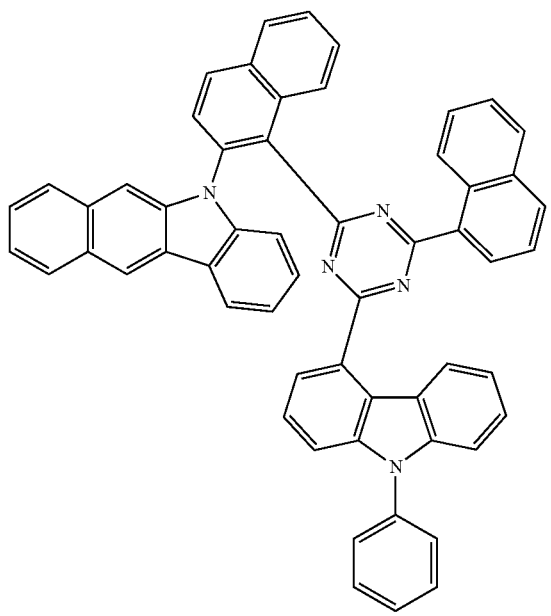

285
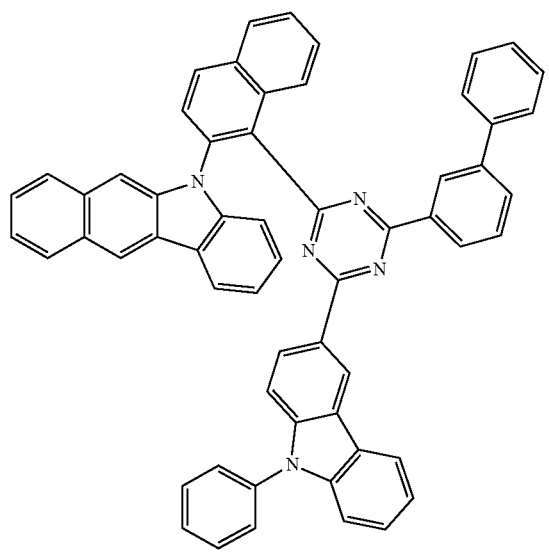
286
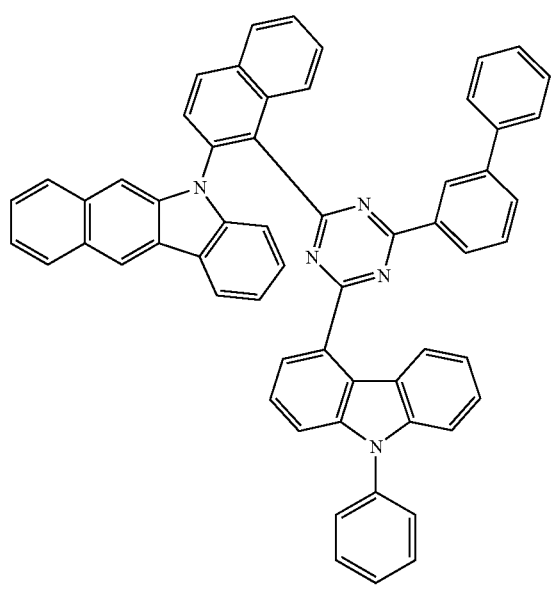
287
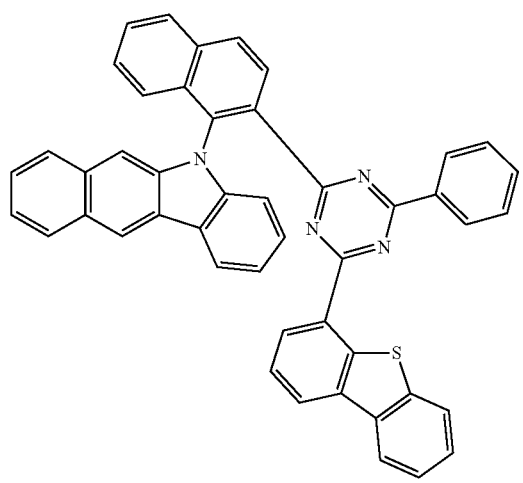
288
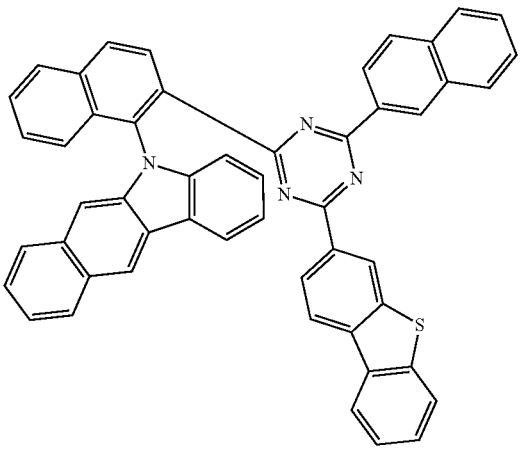
289
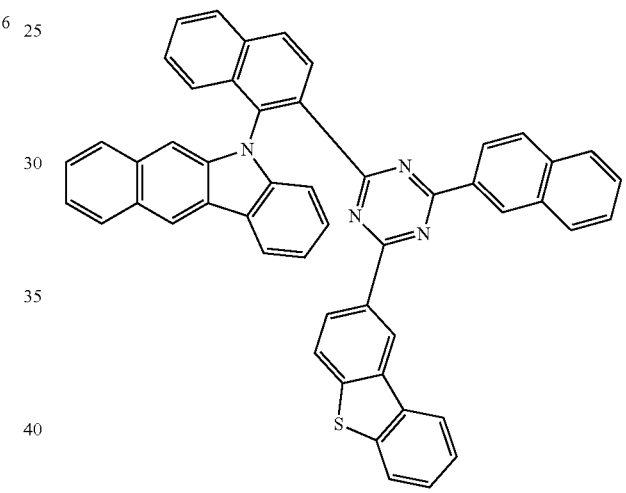
290
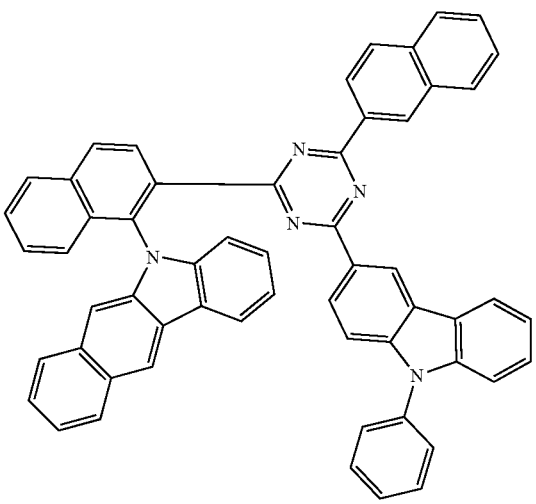

291

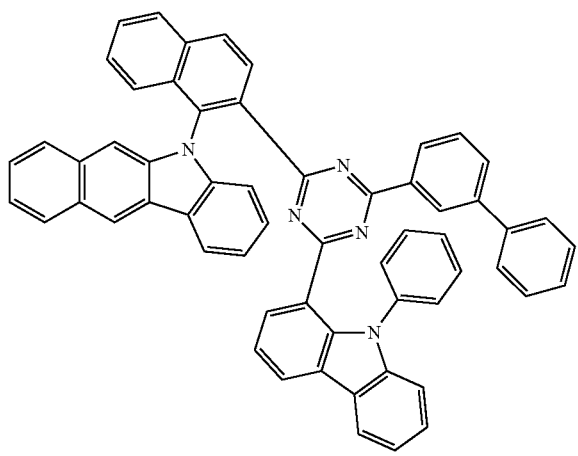

292

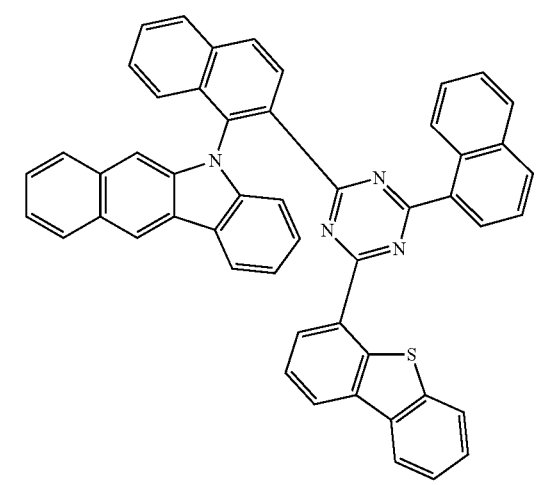

293

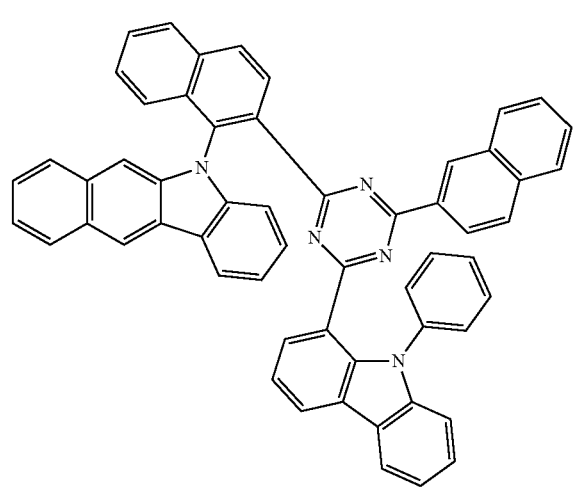

294

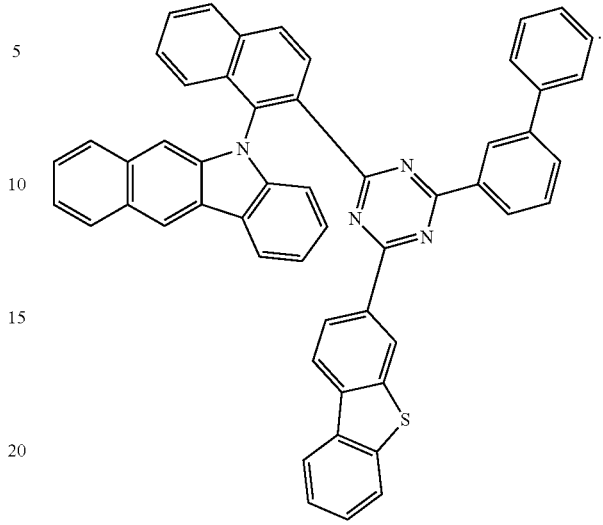

Further, the present specification provides an organic light emitting device including the above-described compound.

An exemplary embodiment of the present specification provides an organic light emitting device including: a first electrode; a second electrode provided to face the first electrode; and an organic material layer having one or more organic material layers provided between the first electrode and the second electrode, in which one or more layers of the organic material layers include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element can be further included.

The organic material layer of the organic light emitting device of the present specification can also be composed of a single-layered structure, but can be composed of a multi-layered structure in which an organic material layer having two or more layers is stacked. For example, the organic light emitting device of the present invention can have a structure including a hole injection layer, a hole transport layer, a light emitting layer, an electron transport layer, an electron injection layer, and the like as organic material layers. However, the structure of the organic light emitting device is not limited thereto, and can include a fewer number of organic layers.

In an exemplary embodiment of the present specification, the organic material layer includes a hole injection layer or a hole transport layer, and the hole injection layer or the hole transport layer includes the compound.

In an exemplary embodiment of the present specification, the organic material layer includes a light emitting layer, and the light emitting layer includes the compound.

In an exemplary embodiment of the present specification, the organic material layer includes an electron transport layer or an electron injection layer, and the electron transport layer or the electron injection layer includes the compound.

In an exemplary embodiment of the present specification, the organic light emitting device further includes one or two or more layers selected from the group consisting of a hole injection layer, a hole transport layer, an electron transport layer, an electron injection layer, an electron blocking layer, and a hole blocking layer.

In an exemplary embodiment of the present application, the organic light emitting device includes: a first electrode; a second electrode provided to face the first electrode; a light emitting layer provided between the first electrode and the second electrode; and an organic material layer having two or more layers provided between the light emitting layer and the first electrode, or between the light emitting layer and the second electrode, in which at least one of the two or more layers of the organic material layer includes the compound.

In an exemplary embodiment of the present application, as the two or more layers of the organic material layer, two or more can be selected from the group consisting of an electron transport layer, an electron injection layer, a layer which transports and injects electrons simultaneously, and a hole blocking layer.

In an exemplary embodiment of the present application, the organic material layer includes two or more electron transport layers, and at least one of the two or more electron transport layers includes the compound.

Specifically, in an exemplary embodiment of the present specification, the compound can also be included in one layer of the two or more electron transport layers, and can be included in each of the two or more electron transport layers.

In addition, in an exemplary embodiment of the present application, when the compound is included in each of the two or more electron transport layers, the other materials except for the compound can be the same as or different from each other.

In an exemplary embodiment of the present specification, the organic material layer further includes a hole injection layer or a hole transport layer, which includes a compound including an arylamino group, a carbazolyl group, or a benzocarbazolyl group, in addition to the organic material layer including the compound.

In another exemplary embodiment, the organic light emitting device can be a normal type organic light emitting device in which a first electrode, an organic material layer having one or more layers, and a second electrode are sequentially stacked on a substrate.

In still another exemplary embodiment, the organic light emitting device can be an inverted type organic light emitting device in which a second electrode, an organic material layer having one or more layers, and a first electrode are sequentially stacked on a substrate.

For example, the structure of the organic light emitting device according to an exemplary embodiment of the present specification is exemplified in FIGS. 1 and 2.

FIG. 1 exemplifies a structure of an organic light emitting device in which a substrate 1, a first electrode 2, a light emitting layer 3, and a second electrode 4 are sequentially stacked. In the structure described above, the compound can be included in the light emitting layer 3.

FIG. 2 exemplifies a structure of an organic light emitting device in which the substrate 1, the first electrode 2, a hole injection layer 5, a hole transport layer 6, the light emitting layer 3, an electron transport layer 7, and the second electrode 4 are sequentially stacked. In the structure described above, the compound can be included in one or more layers of the hole injection layer 5, the hole transport layer 6, the light emitting layer 3, and the electron transport layer 7.

In the structure described above, the compound can be included in one or more layers of the hole injection layer, the hole transport layer, the light emitting layer, and the electron transport layer.

The organic light emitting device of the present specification can be manufactured by the materials and methods known in the art, except that one or more layers of the organic material layer include the compound of the present specification, that is, the compound.

When the organic light emitting device includes a plurality of organic material layers, the organic material layers can be formed of the same material or different materials.

The organic light emitting device of the present specification can be manufactured by the materials and methods known in the art, except that one or more layers of the organic material layer include the compound, that is, the compound of Formula 1.

For example, the organic light emitting device of the present specification can be manufactured by sequentially stacking a first electrode, an organic material layer, and a second electrode on a substrate. In this case, the organic light emitting device can be manufactured by depositing a metal or a metal oxide having conductivity, or an alloy thereof on a substrate to form a first electrode, forming an organic material layer including a hole injection layer, a hole transport layer, a light emitting layer, and an electron transport layer thereon, and then depositing a material, which can be used as a second electrode, thereon, by using a physical vapor deposition (PVD) method such as sputtering or e-beam evaporation. In addition to the method described above, an organic light emitting device can be made by sequentially depositing a second electrode material, an organic material layer, and a first electrode material on a substrate.

Further, the compound of Formula 1 can be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method described above, an organic light emitting device can also be made by sequentially depositing a second electrode material, an organic material layer, and a first electrode material on a substrate (International Publication No. WO 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the first electrode material, materials having a high work function are usually preferred so as to facilitate the injection of holes into an organic material layer. Specific examples of the first electrode material which can be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methyl-thiophene), poly

[3,4-(ethylene-1,2-dioxy)thiophene] (PEDOT), polypyrrole, and polyaniline; and the like, but are not limited thereto.

As the second electrode material, materials having a low work function are usually preferred so as to facilitate the injection of electrons into an organic material layer. Specific examples of the second electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

The hole injection layer is a layer which injects holes from an electrode, and a hole injection material is preferably a compound which has a capability of transporting holes and thus has an effect of injecting holes at a first electrode and an excellent effect of injecting holes into a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the first electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transport layer is a layer which accepts holes from a hole injection layer and transports the holes to a light emitting layer, and a hole transport material is suitably a material having high hole mobility which can accept holes from a first electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The light emitting material is a material which can emit light in a visible light region by accepting and combining holes and electrons from a hole transport layer and an electron transport layer, respectively, and preferably a material having high quantum efficiency for fluorescence or phosphorescence. Specific examples thereof include an 8-hydroxy-quinoline aluminum complex ($Alq_3$), a carbazole-based compound, a dimerized styryl compound, BAlq, a 10-hydroxybenzoquinoline-metal compound, benzoxazole-based, benzothiazole-based and benzimidazole-based compounds, a poly(p-phenylenevinylene) (PPV)-based polymer, a spiro compound, polyfluorene, rubrene, and the like, but are not limited thereto.

The light emitting layer can include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a dibenzofuran derivative, a ladder-type furan compound, a pyrimidine derivative, and the like, but the examples are not limited thereto.

The electron transporting layer is a layer which accepts electrons from an electron injection layer and transports the electrons to a light emitting layer, and an electron transport material is suitably a material having high electron mobility which can proficiently accept electrons from a second electrode and transfer the electrons to a light emitting layer. Specific examples thereof include: an Al complex of 8-hydroxyquinoline, a complex including $Alq_3$, an organic radical compound, a hydroxyflavone-metal complex, and the like, but are not limited thereto. The electron transport layer can be used with any desired cathode material, as used according to the related art. In particular, appropriate examples of the cathode material include a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and the electron injection material is preferably a compound which has a capability of transporting electrons, an effect of injecting electrons from a second electrode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxy-quinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a second electrode, and can be generally formed under the same conditions as those of the hole injection layer. Specific examples thereof include an oxadiazole derivative or a triazole derivative, a phenanthroline derivative, BCP, an aluminum complex, and the like, but are not limited thereto.

A dopant according to an exemplary embodiment of the present specification can be selected from the following structural formulae:

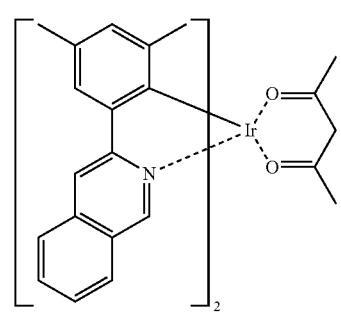

Dp-1

Dp-2 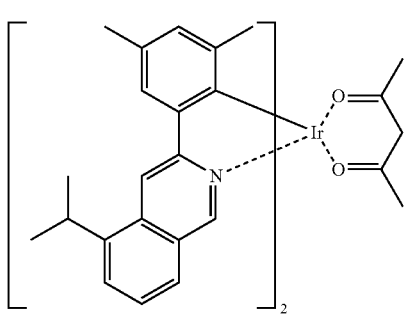
Dp-3 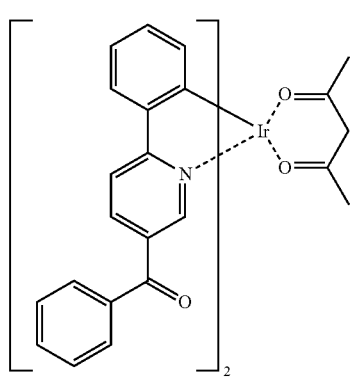
Dp-4 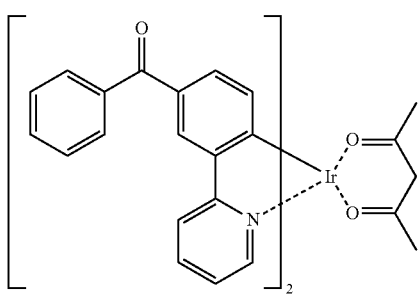
Dp-5 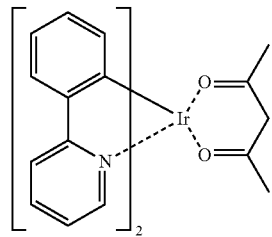
Dp-6 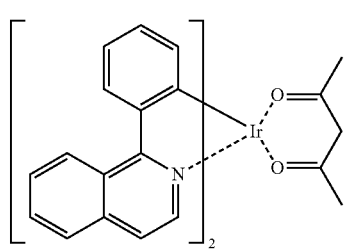
Dp-7 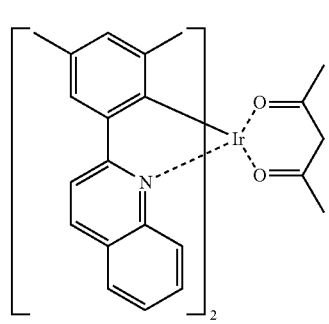
Dp-8 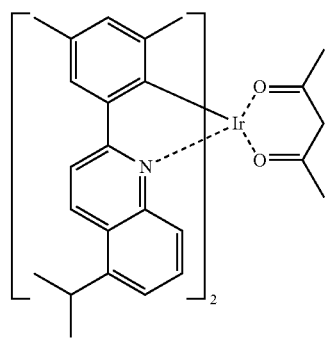
Dp-9 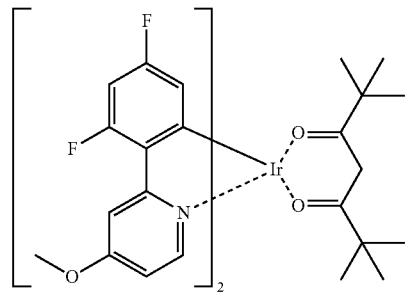
Dp-10 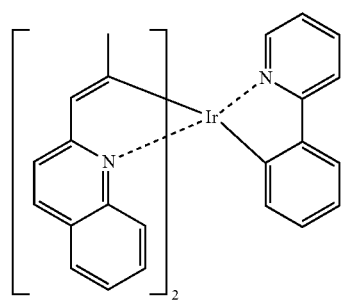
Dp-11 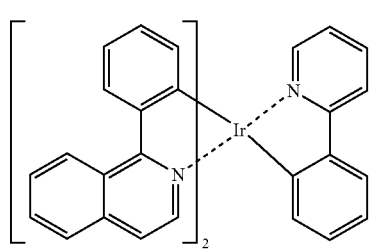

Dp-12
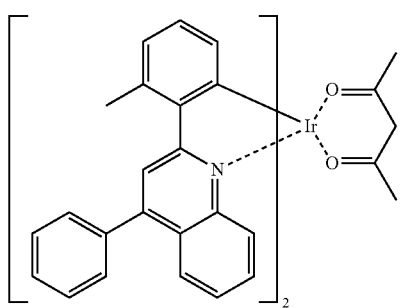
DP-13
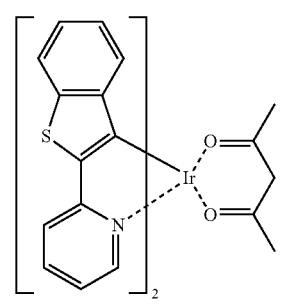
Dp-14
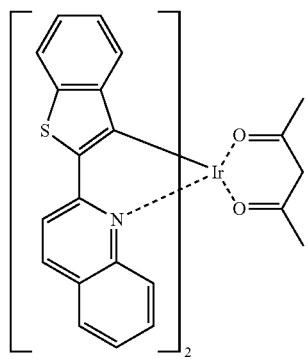
Dp-15
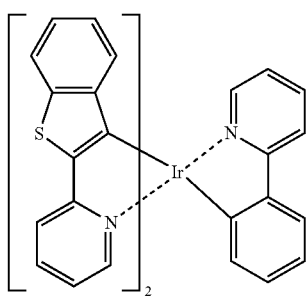
DP-13
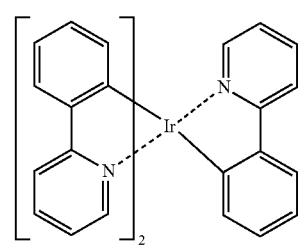
Dp-14
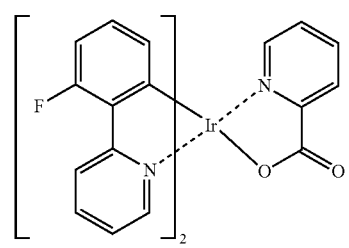
Dp-15
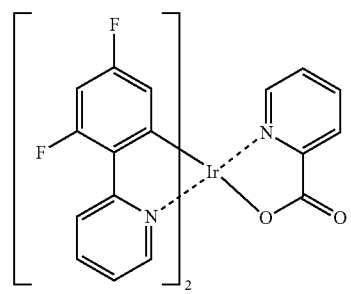
Dp-16
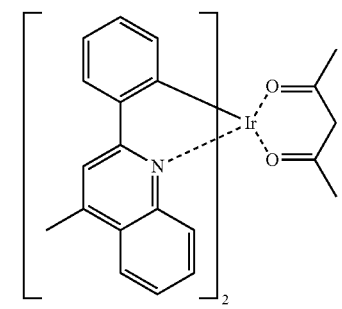
Dp-17
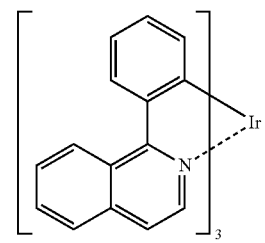
Dp-18
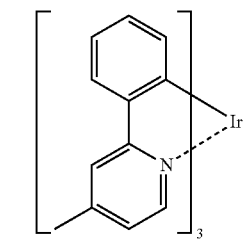
Dp-19
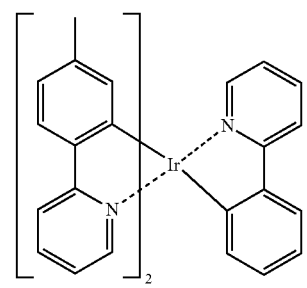

Dp-20
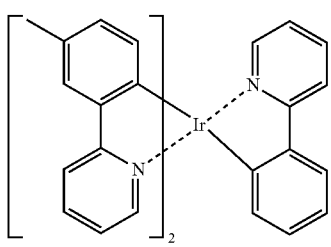
Dp-21
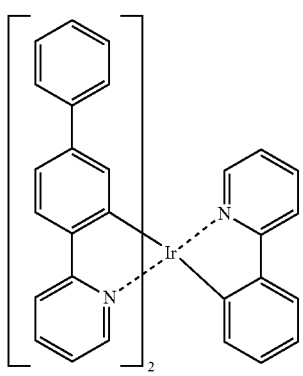
Dp-22
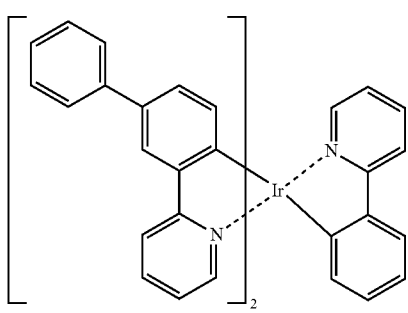
Dp-23
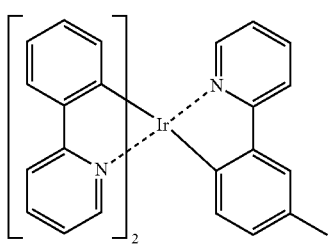
Dp-24
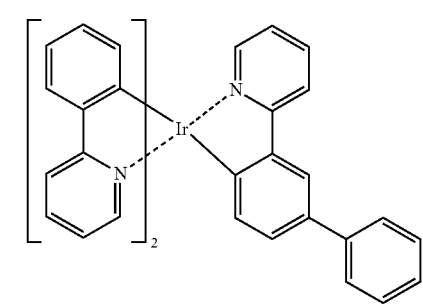
Dp-25
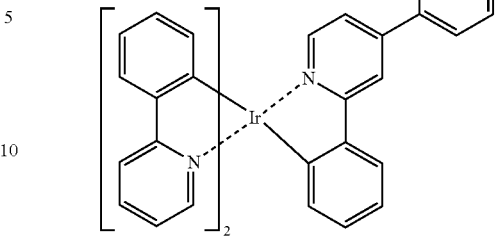
Dp-26
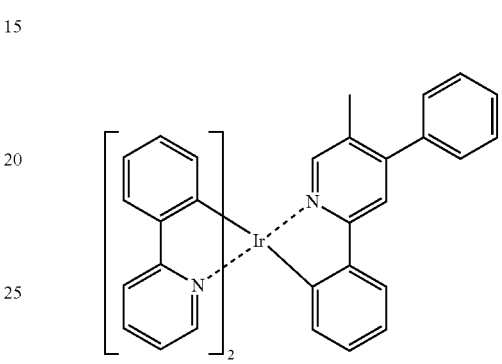
Dp-27
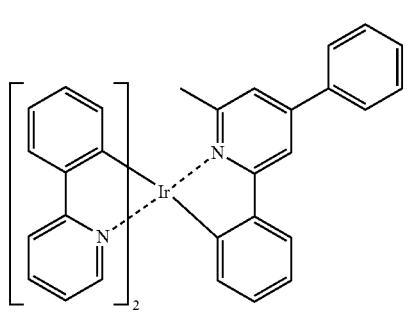
Dp-28
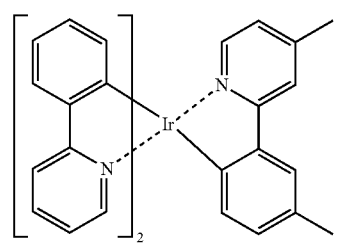
Dp-29
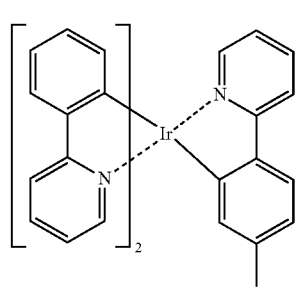

Dp-30 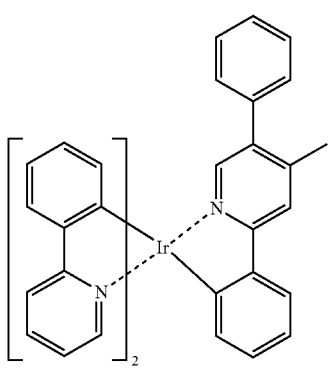

Dp-31 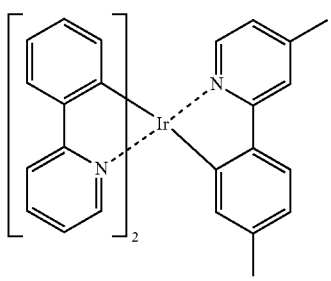

Dp-32 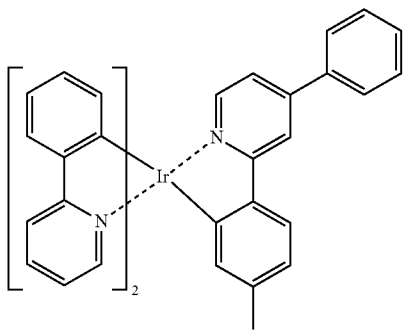

Dp-33 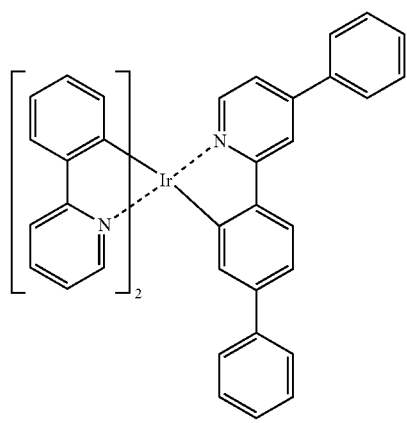

Dp-34 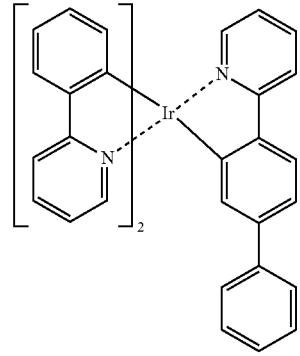

Dp-35 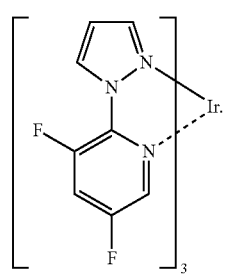

The above-specified structures are dopant compounds, and the dopant compounds are not limited thereto.

The organic light emitting device according to the present specification can be a top emission type, a bottom emission type, or a dual emission type according to the materials to be used.

MODE FOR INVENTION

The preparation method of the compound of Formula 1 and the manufacture of an organic light emitting device using the same will be specifically described in the following Examples. However, the following Examples are provided for exemplifying the present invention, and the scope of the present invention is not limited thereby.

The compound of the present invention was prepared by using a Buchwald-Hartwig coupling reaction, a Heck coupling reaction, a Suzuki coupling reaction, and the like as a representative reaction, and all the compounds were purified, and then subjected to sublimation purification, and a device evaluation was performed.

Preparation Example 1

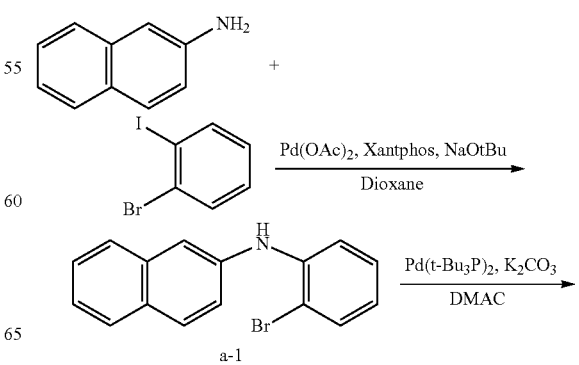

-continued

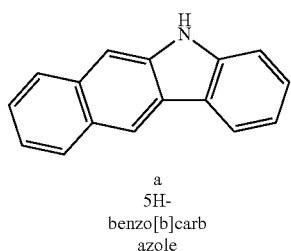

a
5H-benzo[b]carbazole

1) Preparation of Formula a-1

300.0 g (1.0 eq) of naphthalen-2-amine, 592.7 g (1.0 eq) of 1-bromo-2-iodobenzene, 302.0 g (1.5 eq) of NaOtBu, 4.70 g (0.01 eq) of Pd(OAc)$_2$, and 12.12 g (0.01 eq) of Xantphos were dissolved in 5 L of 1,4-dioxane, and the resulting solution was stirred under reflux. After 3 hours, when the reaction was completed, the solvent was removed by reducing pressure. Thereafter, the resulting product was completely dissolved in ethyl acetate and washed with water, and approximately 70% of the solvent was removed again by reducing pressure. Hexane was put thereinto in a reflux state, and crystals were precipitated, cooled, and then filtered. The resulting product was subjected to column chromatography to obtain 443.5 g (yield 71%) of Compound a-1. [M+H]=299

2) Preparation of Formula a (5H-benzo[b]carbazole)

443.5 g (1.0 eq) of Formula a-1, 8.56 g (0.01 eq) of Pd(t-Bu$_3$P)$_2$, and 463.2 g (2.00 eq) of K$_2$CO$_3$ were put into 4 L of dimethylacetamide, and the resulting mixture was stirred under reflux. After 3 hours, crystals were precipitated by pouring water into the reactant, and filtered. After the filtered solid was completely dissolved in 1,2-dichlorobenzene, the resulting solution was washed with water, crystals were precipitated by concentrating the solution in which the product was dissolved, under reduced pressure, cooled, and then filtered. The resulting product was purified by column chromatography to obtain 174.8 g (yield 48%) of Formula a (5H-benzo[b]carbazole). [M+H]=218

FIGS. 3 and 4 illustrate 1H-NMR and mass analysis results for confirming Formula a.

Synthesis Example 1

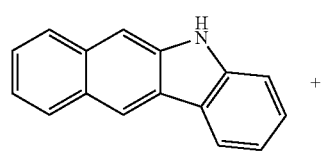

+

-continued

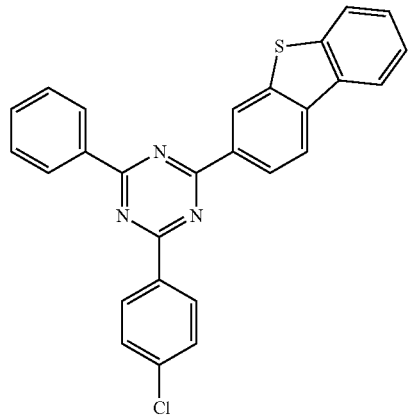

2-1

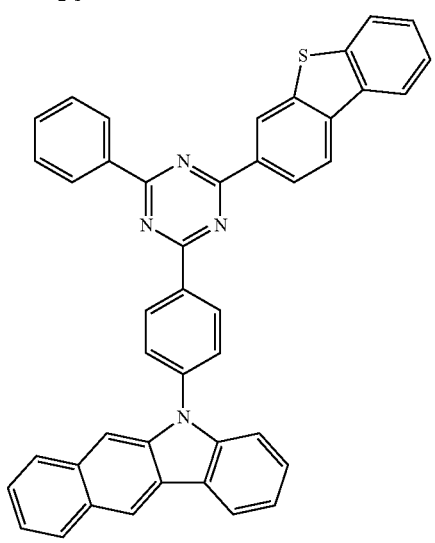

2

10.0 g (1.0 eq) of Formula a, 22.76 g (1.1 eq) of Intermediate 2-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 19.48 g (yield 67%) of Compound 2. [M+H]=631

Synthesis Example 2

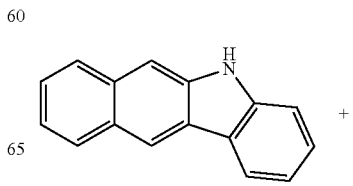

+

-continued

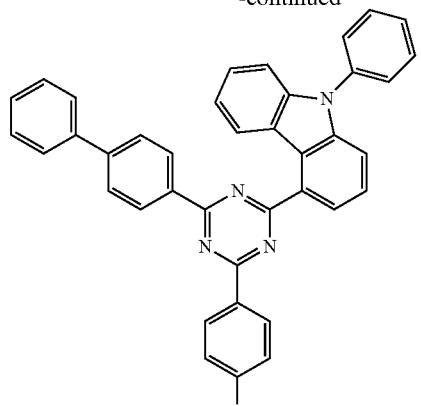

22-1

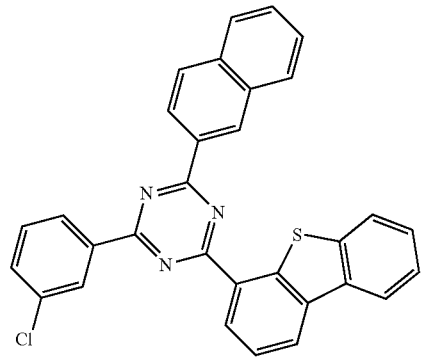

74-1

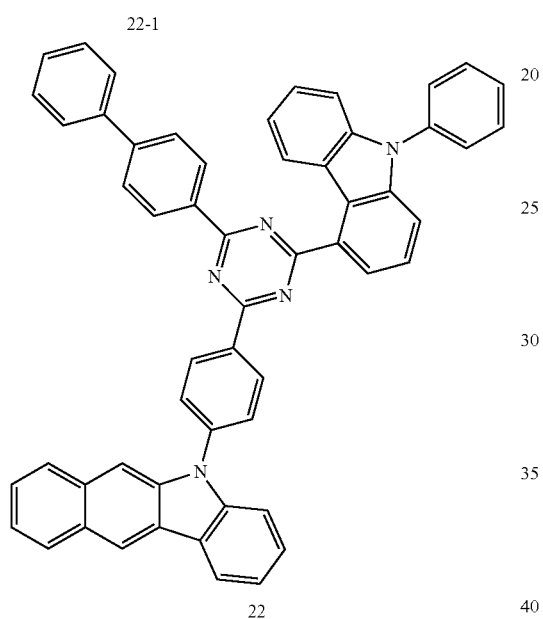

22

10.0 g (1.0 eq) of Formula a, 29.65 g (1.1 eq) of Intermediate 22-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 25.06 g (yield 71%) of Compound 22. [M+H]=766

Synthesis Example 3

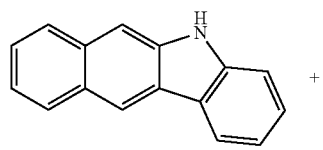 +

74

10.0 g (1.0 eq) of Formula a, 25.34 g (1.1 eq) of Intermediate 74-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 22.90 g (yield 73%) of Compound 74. [M+H]=681

Synthesis Example 4

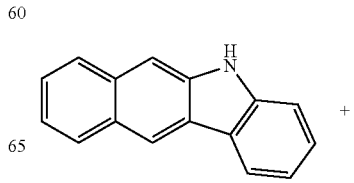 +

127
-continued

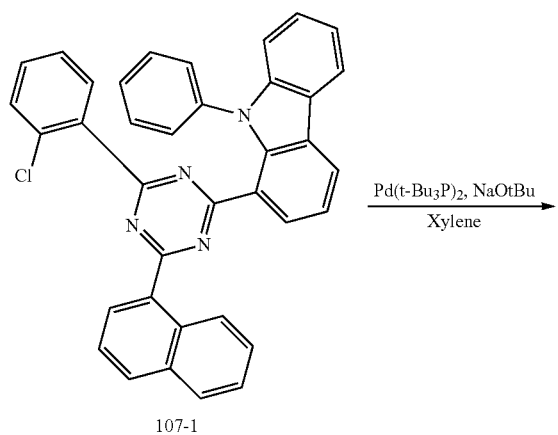
107-1

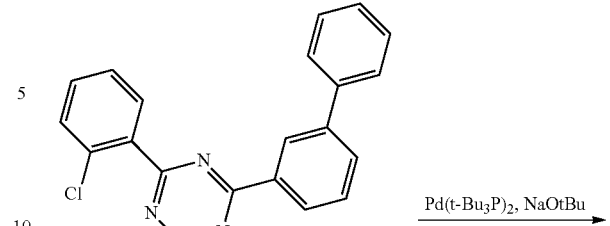

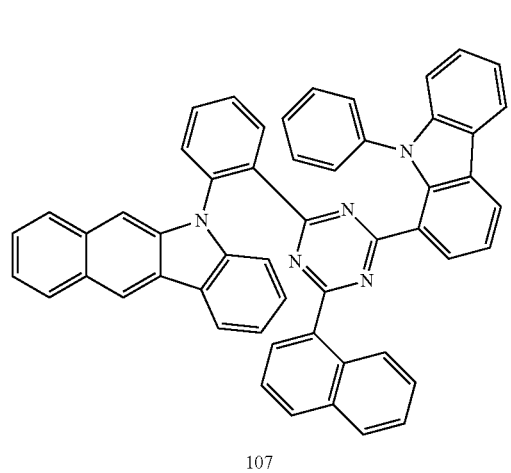
107

10.0 g (1.0 eq) of Formula a, 28.33 g (1.1 eq) of Intermediate 107-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 23.87 g (yield 70%) of Compound 107. [M+H]=740

Synthesis Example 5

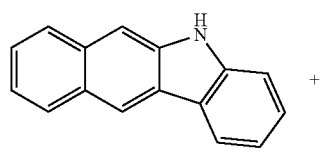 +

128
-continued

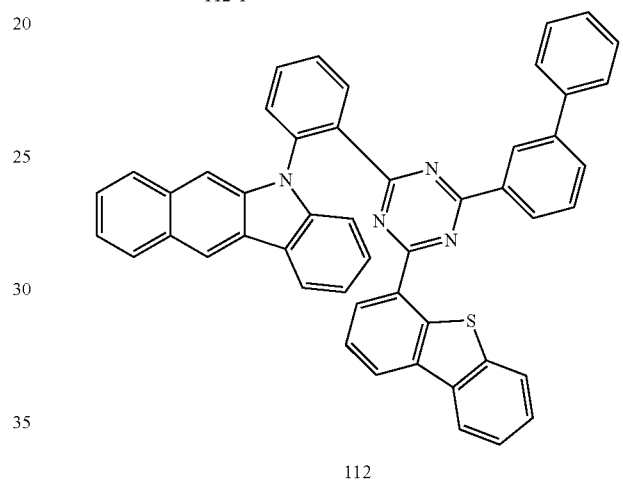
112-1

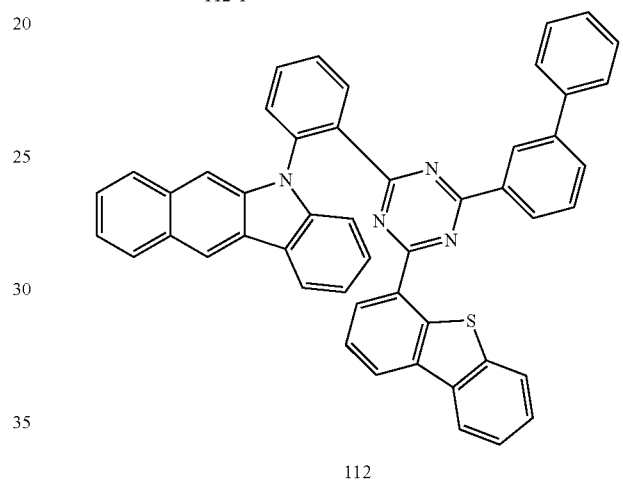
112

10.0 g (1.0 eq) of Formula a, 26.66 g (1.1 eq) of Intermediate 112-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 20.85 g (yield 64%) of Compound 112. [M+H]=707

Synthesis Example 6

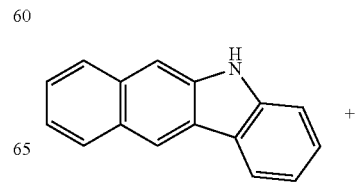 +

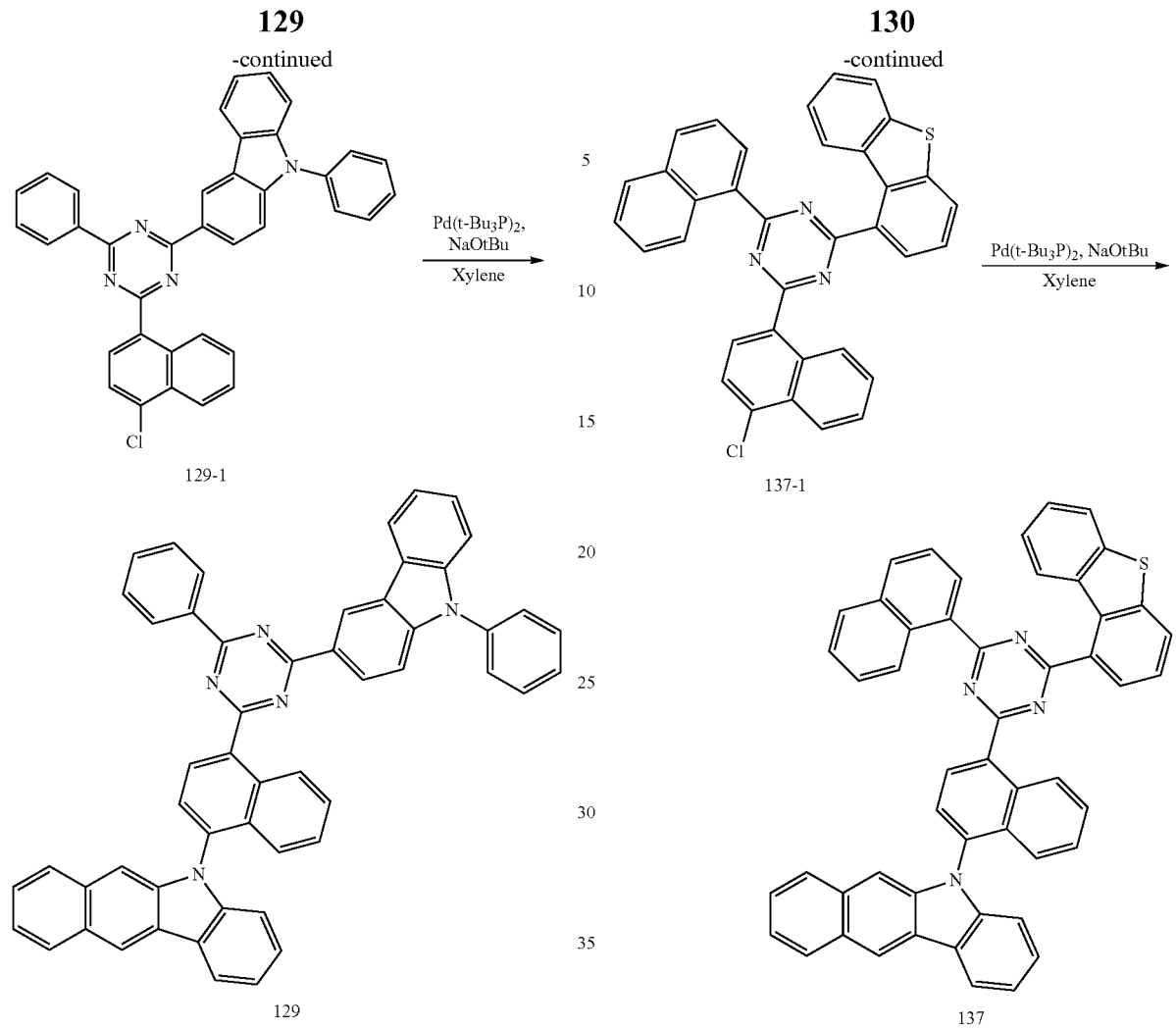

10.0 g (1.0 eq) of Formula a, 28.33 g (1.1 eq) of Intermediate 129-1, 8.84 g (2.0 eq) of NaOtBu, and 0.12 g (0.005 eq) of Pd(t-Bu₃P)₂ were dissolved in 250 ml of xylene, and the resulting solution was stirred under reflux. After 3 hours, when the reaction was completed, the solvent was removed by reducing pressure. Thereafter, the product was completely dissolved in CHCl₃, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 21.14 g (yield 62%) of Compound 129. [M+H]=740

10.0 g (1.0 eq) of Formula a, 27.88 g (1.1 eq) of Intermediate 137-1, 8.84 g (2.0 eq) of NaOtBu, and 0.12 g (0.005 eq) of Pd(t-Bu₃P)₂ were dissolved in 250 ml of xylene, and the resulting solution was stirred under reflux. After 3 hours, when the reaction was completed, the solvent was removed by reducing pressure. Thereafter, the product was completely dissolved in CHCl₃, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 21.89 g (yield 65%) of Compound 137. [M+H]=731

Synthesis Example 7

Synthesis Example 8

131
-continued

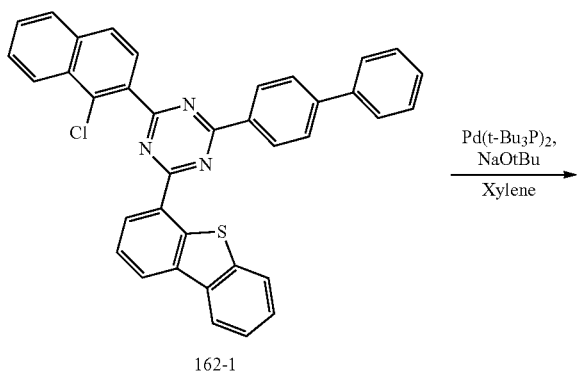

162-1

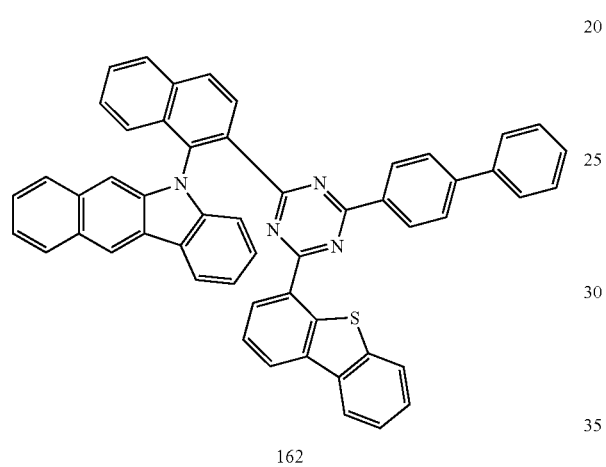

162

132
-continued

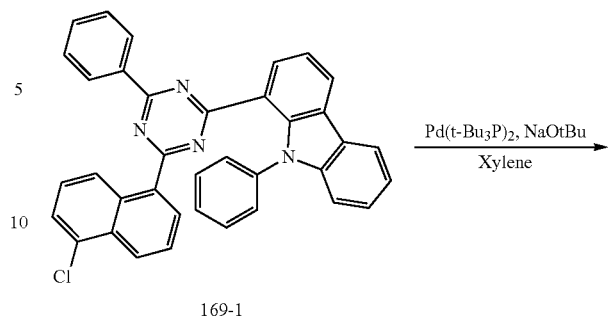

169-1

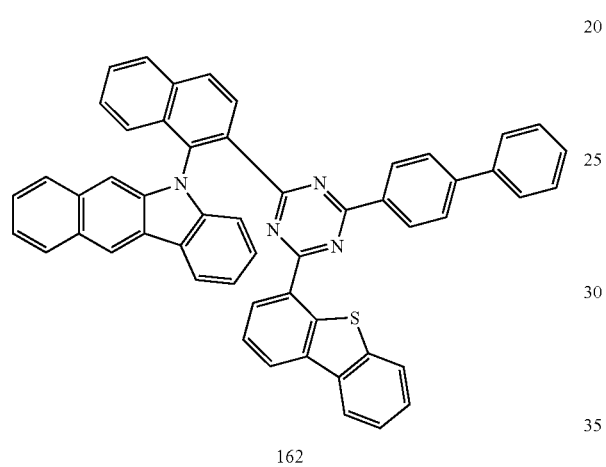

169

10.0 g (1.0 eq) of Formula a, 29.19 g (1.1 eq) of Intermediate 162-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 21.27 g (yield 61%) of Compound 162. [M+H]=757

Synthesis Example 9

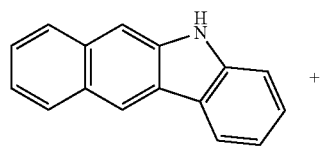 +

10.0 g (1.0 eq) of Formula a, 28.33 g (1.1 eq) of Intermediate 169-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 21.82 g (yield 64%) of Compound 169. [M+H]=740

Synthesis Example 10

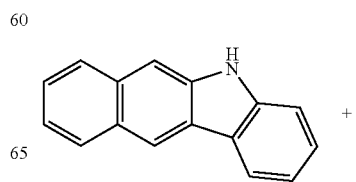 +

-continued

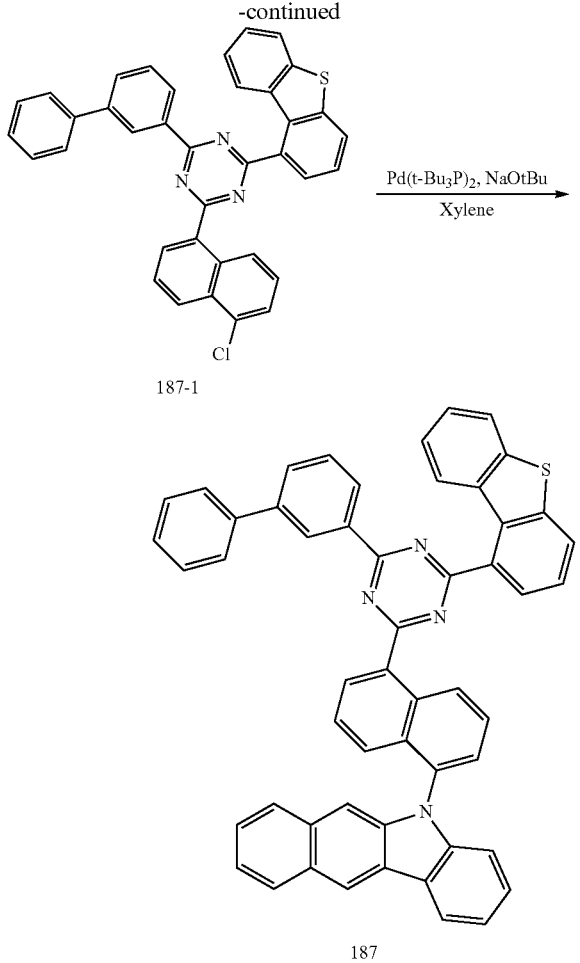

187-1

187

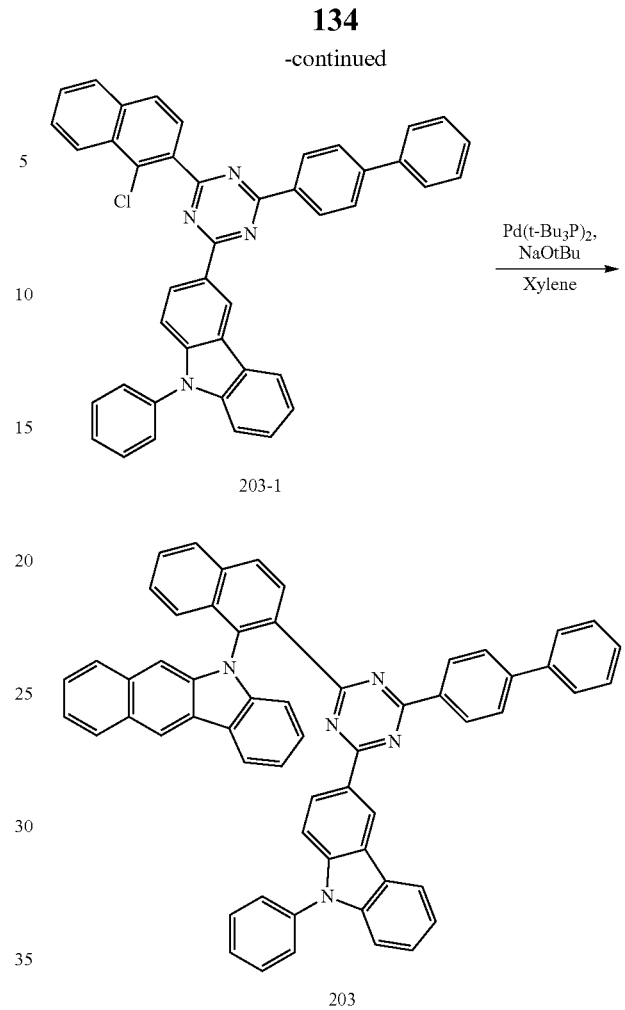

203-1

203

10.0 g (1.0 eq) of Formula a, 29.19 g (1.1 eq) of Intermediate 187-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 23.37 g (yield 67%) of Compound 187. [M+H]=757

10.0 g (1.0 eq) of Formula a, 32.18 g (1.1 eq) of Intermediate 203-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 23.69 g (yield 63%) of Compound 203. [M+H]=816

Synthesis Example 11

Synthesis Example 12

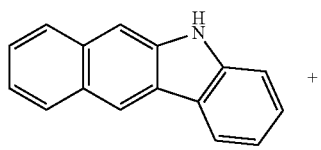 +

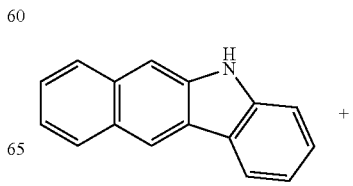 +

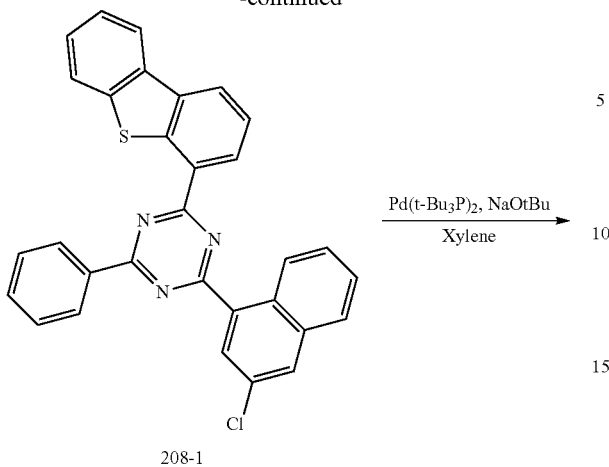

208-1

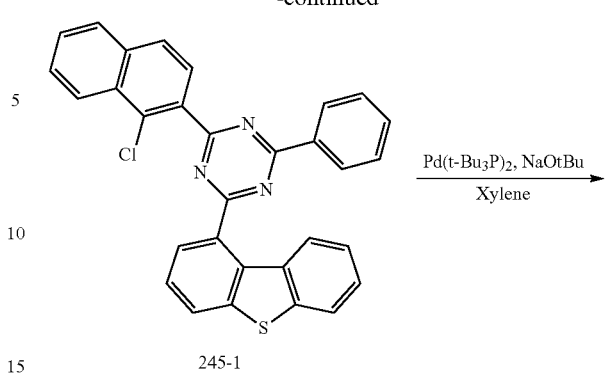

245-1

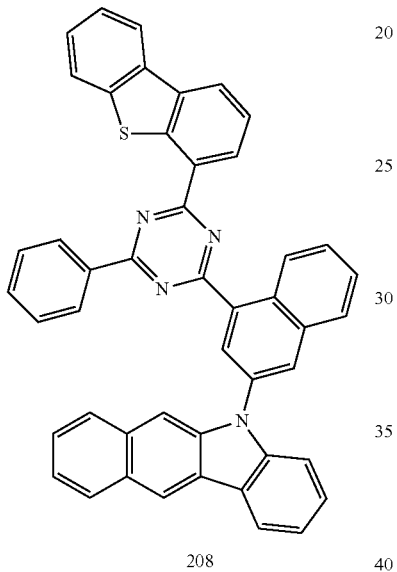

208

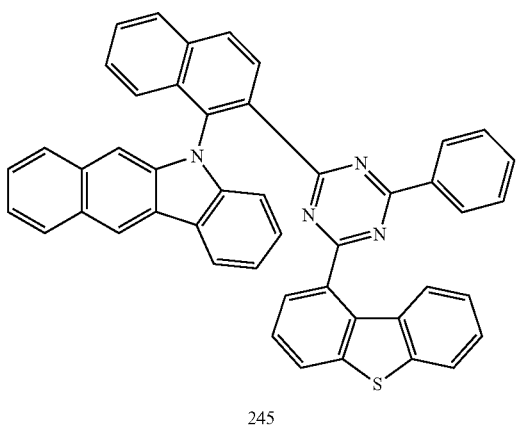

245

10.0 g (1.0 eq) of Formula a, 25.34 g (1.1 eq) of Intermediate 208-1, 8.84 g (2.0 eq) of NaOtBu, and 0.12 g (0.005 eq) of Pd(t-Bu₃P)₂ were dissolved in 250 ml of xylene, and the resulting solution was stirred under reflux. After 3 hours, when the reaction was completed, the solvent was removed by reducing pressure. Thereafter, the product was completely dissolved in CHCl₃, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 21.02 g (yield 67%) of Compound 208. [M+H]=681

Synthesis Example 13

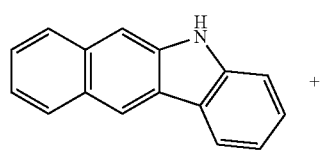

10.0 g (1.0 eq) of Formula a, 25.34 g (1.1 eq) of Intermediate 245-1, 8.84 g (2.0 eq) of NaOtBu, and 0.12 g (0.005 eq) of Pd(t-Bu₃P)₂ were dissolved in 250 ml of xylene, and the resulting solution was stirred under reflux. After 3 hours, when the reaction was completed, the solvent was removed by reducing pressure. Thereafter, the product was completely dissolved in CHCl₃, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 20.39 g (yield 65%) of Compound 245. [M+H]=681

Synthesis Example 14

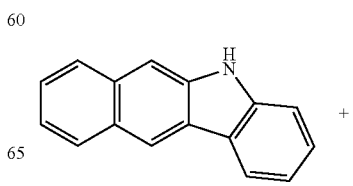

-continued

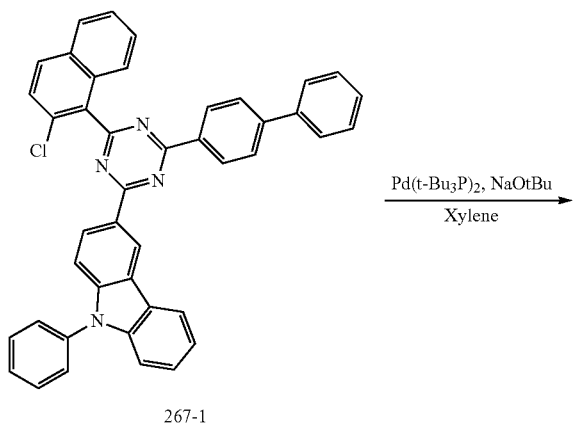

267-1

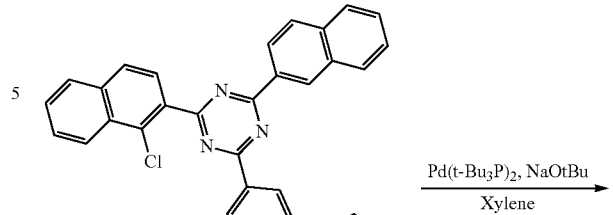

-continued

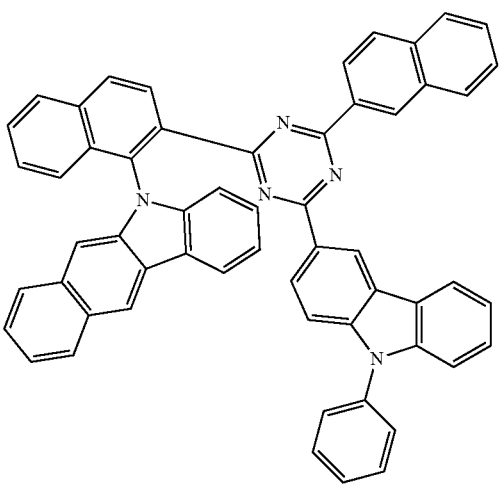

290-1

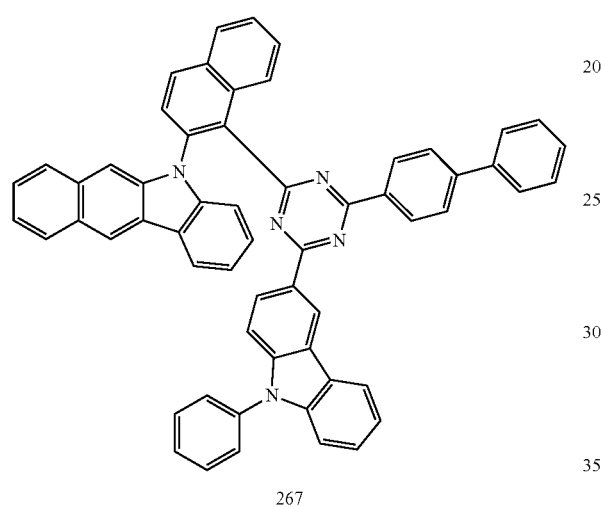

267

10.0 g (1.0 eq) of Formula a, 32.18 g (1.1 eq) of Intermediate 267-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 24.06 g (yield 64%) of Compound 267. [M+H]=816

Synthesis Example 15

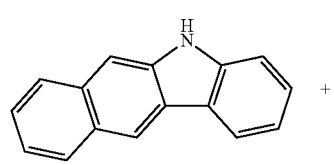

290

10.0 g (1.0 eq) of Formula a, 30.87 g (1.1 eq) of Intermediate 290-1, 8.84 g (2.0 eq) of NaOtBu, and 0.12 g (0.005 eq) of Pd(t-Bu$_3$P)$_2$ were dissolved in 250 ml of xylene, and the resulting solution was stirred under reflux. After 3 hours, when the reaction was completed, the solvent was removed by reducing pressure. Thereafter, the product was completely dissolved in CHCl$_3$, the resulting solution was washed with water, and approximately 50% of the solvent was removed again by reducing pressure. Ethyl acetate then was put thereinto in a reflux state, and crystals were precipitated, cooled, and then filtered. The resulting product was subjected to column chromatography to obtain 22.20 g (yield 61%) of Compound 290. [M+H]=790

Comparative Example 1

A glass substrate thinly coated with indium tin oxide (ITO) to have a thickness of 1,000 Å was put into distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted by using isopropyl alcohol, acetone, and methanol solvents, and the resulting product was dried and then transported to a plasma washing machine. Furthermore, the substrate was washed by using an oxygen plasma for 5 minutes, and then was transported to a vacuum deposition machine.

The following HI-1 compound was formed to have a thickness of 1,150 Å as a hole injection layer on the thus prepared ITO transparent electrode, and the hole injection layer was p-doped with the following A-1 compound at a concentration of 1.5%. The following HT-1 compound was vacuum deposited on the hole injection layer, thereby forming a hole transport layer having a film thickness of 800 Å.

Subsequently, the following EB-1 compound was vacuum deposited to have a film thickness of 150 Å on the hole transport layer, thereby forming an electron blocking layer. Subsequently, the following RH-1 compound and the following Dp-7 compound were vacuum deposited at a weight ratio of 98:2 on the EB-1 deposition film, thereby forming a red light emitting layer having a thickness of 400 Å. The following HB-1 compound was vacuum deposited to have a thickness of 30 Å on the light emitting layer, thereby forming a hole blocking layer. Subsequently, the following ET-1 compound and the following LiQ compound were vacuum deposited at a weight ratio of 2:1 on the hole blocking layer, thereby forming an electron injection and transport layer having a thickness of 300 Å. Lithium fluoride (LiF) and aluminum were sequentially deposited on the electron injection and transport layer to have a thickness of 12 Å and 1,000 Å, respectively, thereby forming a negative electrode.

HI-1

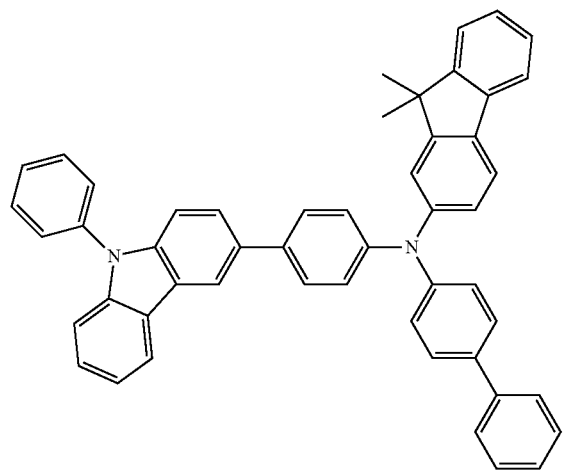

A-1

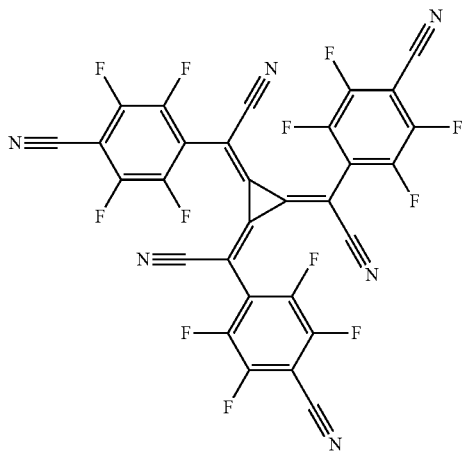

HT-1

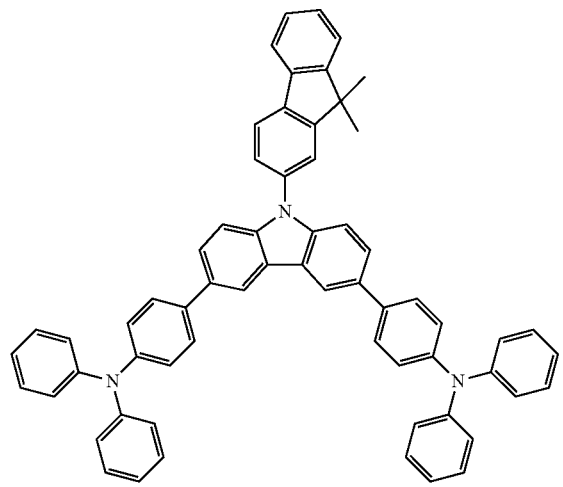

EB-1

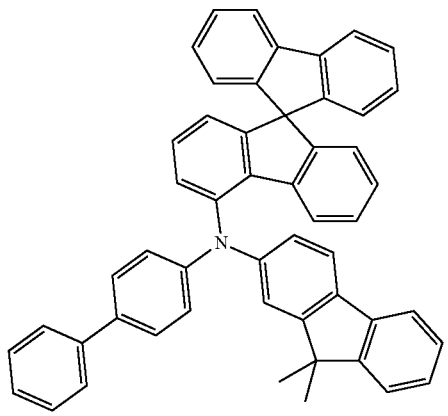

RH-1
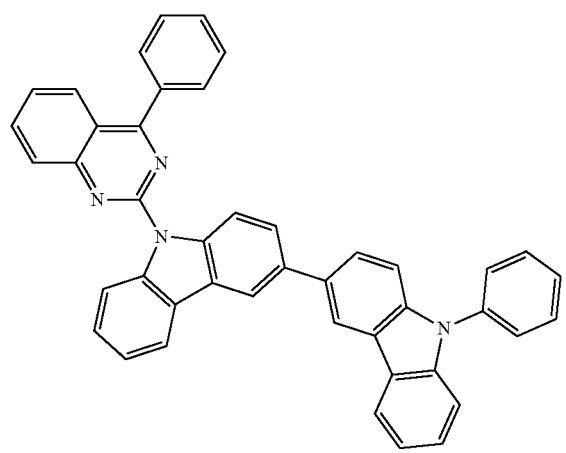
Dp-7
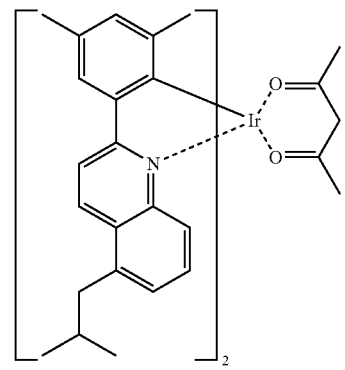
HB-1
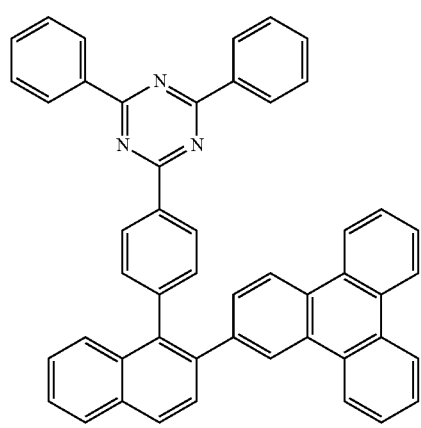
ET-1
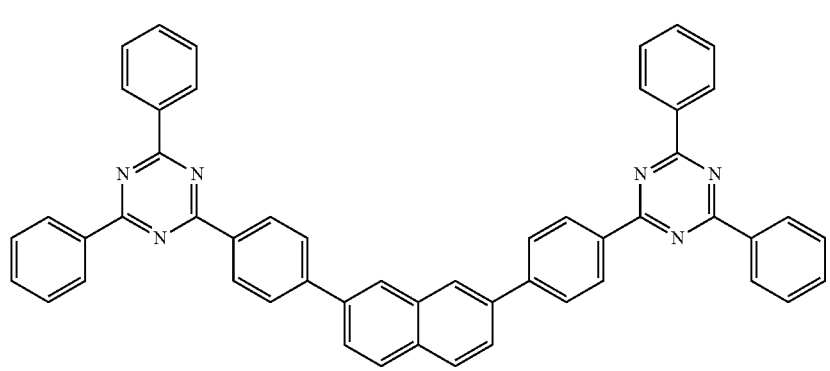
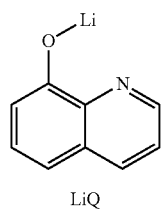
LiQ
RH-2
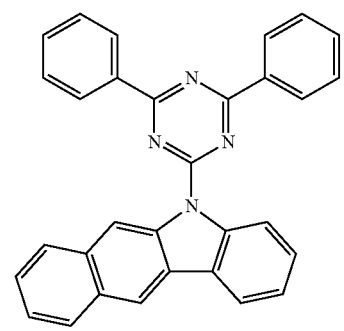

-continued
RH-3
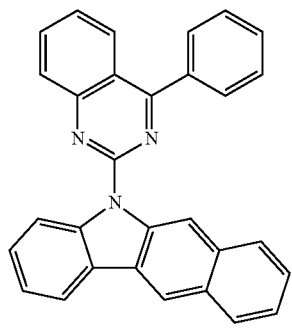
RH-4
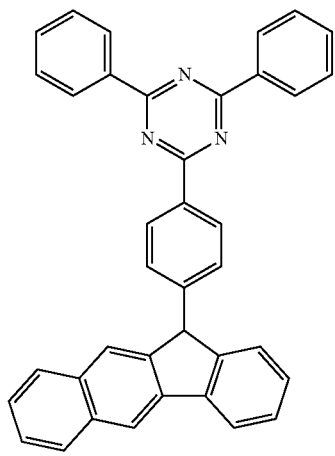
RH-5
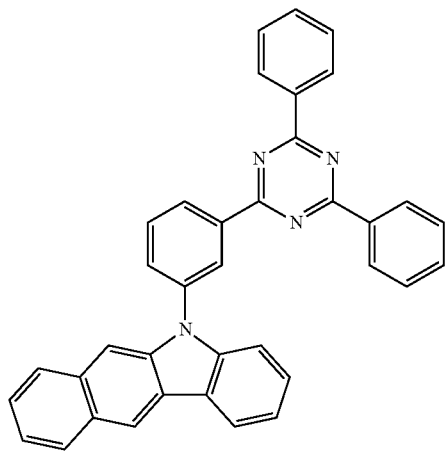
RH-6
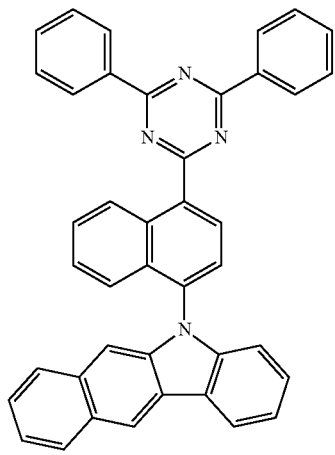
RH-7
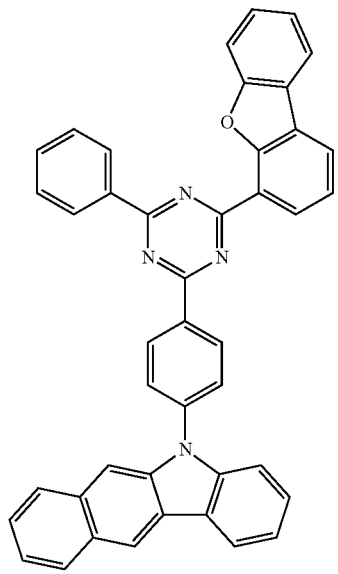
RH-8
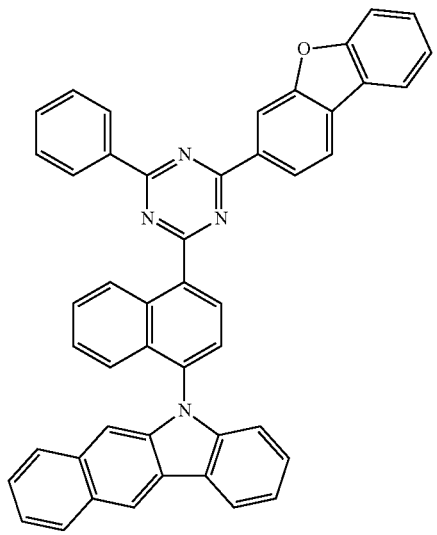

-continued
RH-9
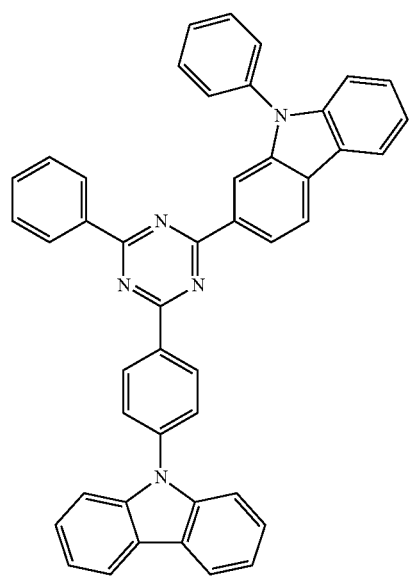
RH-10
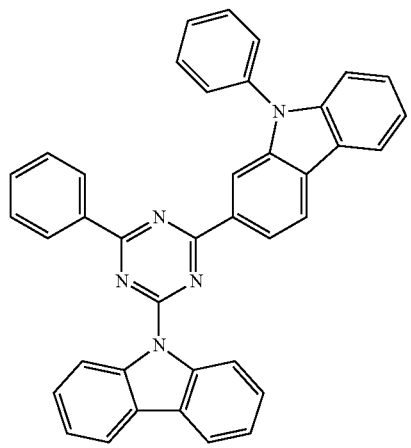
RH-11
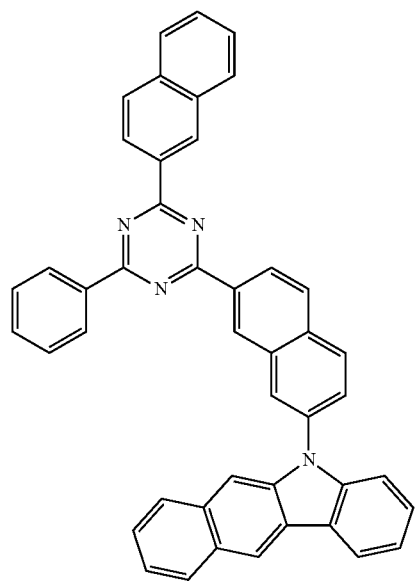
RH-12
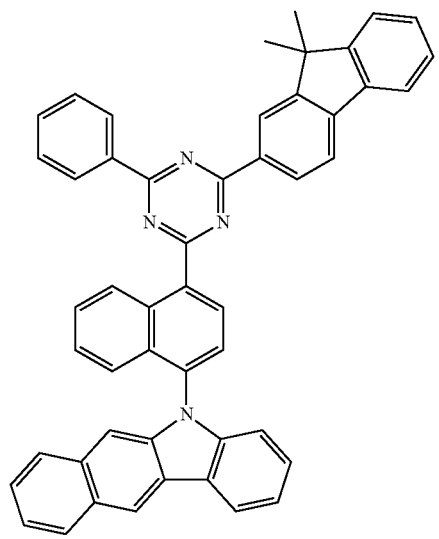

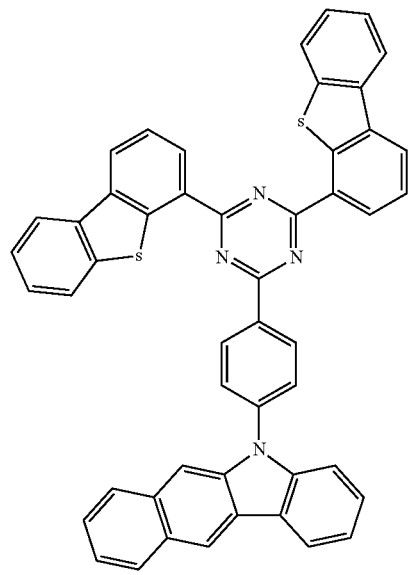

RH-13

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

Examples 1 to 15

Organic light emitting devices were manufactured in the same manner as in Comparative Example 1, except that in the organic light emitting device in Comparative Example 1, the compounds described in the following Table 1 were used instead of RH-1.

Comparative Examples 2 to 13

Organic light emitting devices were manufactured in the same manner as in Comparative Example 1, except that in the organic light emitting device in Comparative Examples 2 to 13, the compounds described in the following Table 1 were used instead of RH-1.

When current was applied to the organic light emitting devices manufactured in Examples 1 to 15 and Comparative Examples 1 to 13, the voltage, efficiency, and service life of each organic light emitting device were measured, and the results thereof are shown in the following Table 1. T98 means the time taken for the luminance to be reduced to 98% of the initial luminance (5,000 nit).

TABLE 1

| Classification | Material | Driving voltage (V) | Efficiency (cd/A) | Service life T98 (hr) | Light emission color |
|---|---|---|---|---|---|
| Comparative Example 1 | RH-1 | 4.51 | 30.5 | 171 | Red |
| Example 1 | Compound 2 | 4.17 | 35.5 | 253 | Red |
| Example 2 | Compound 22 | 4.24 | 37.7 | 243 | Red |
| Example 3 | Compound 74 | 3.97 | 39.8 | 301 | Red |
| Example 4 | Compound 107 | 3.99 | 40.7 | 290 | Red |
| Example 5 | Compound 112 | 3.89 | 37.1 | 287 | Red |
| Example 6 | Compound 129 | 3.90 | 37.8 | 275 | Red |
| Example 7 | Compound 137 | 4.10 | 37.6 | 285 | Red |
| Example 8 | Compound 162 | 4.07 | 38.0 | 277 | Red |
| Example 9 | Compound 169 | 4.21 | 37.9 | 271 | Red |
| Example 10 | Compound 187 | 3.95 | 39.1 | 267 | Red |
| Example 11 | Compound 203 | 4.13 | 35.1 | 260 | Red |
| Example 12 | Compound 208 | 4.10 | 37.1 | 251 | Red |
| Example 13 | Compound 245 | 3.96 | 39.4 | 269 | Red |
| Example 14 | Compound 267 | 3.85 | 40.0 | 258 | Red |
| Example 15 | Compound 290 | 3.97 | 38.7 | 250 | Red |
| Comparative Example 2 | RH-2 | 4.33 | 34.2 | 105 | Red |
| Comparative Example 3 | RH-3 | 4.75 | 30.1 | 131 | Red |
| Comparative Example 4 | RH-4 | 4.50 | 31.5 | 101 | Red |
| Comparative Example 5 | RH-5 | 4.48 | 30.0 | 87 | Red |
| Comparative Example 6 | RH-6 | 4.31 | 33.5 | 137 | Red |
| Comparative Example 7 | RH-7 | 4.57 | 31.7 | 84 | Red |
| Comparative Example 8 | RH-8 | 4.33 | 32.5 | 178 | Red |
| Comparative Example 9 | RH-9 | 4.59 | 26.7 | 54 | Red |
| Comparative Example 10 | RH-10 | 4.54 | 25.3 | 84 | Red |
| Comparative Example 11 | RH-11 | 4.39 | 29.5 | 71 | Red |
| Comparative Example 12 | RH-12 | 4.37 | 27.7 | 77 | Red |
| Comparative Example 13 | RH-13 | 4.48 | 28.3 | 80 | Red |

When current was applied to the organic light emitting devices manufactured in Examples 1 to 15 and Comparative Examples 1 to 13, the results of Table 1 were obtained. A material widely used in the related art was used for the red organic light emitting device in Comparative Example 1, and the red organic light emitting device has a structure in which Compound [EB-1] and RH-1/Dp-7 are used as an electron blocking layer and a red light emitting layer, respectively. In Comparative Examples 2 to 13, the organic light emitting devices were manufactured by using RH-2 to RH-13 instead of RH-1. Referring to the results in Table 1, it was observed that when the compound of the present invention was used as a host of the red light emitting layer, the driving voltage was reduced by about 30% and the efficiency was increased by 25% or more as compared to the materials in the Comparative Examples, and it could be seen that energy was transferred well from the host to the red dopant. Further, it could be seen that service life characteristics could be significantly improved two times or more while maintaining high efficiency. It can be ultimately determined that the reason is because the compound of the present invention has higher stability for electrons and holes than the compounds in the Comparative Examples. In conclusion, it can be confirmed that when the compound of the present invention is used as a host of a red light emitting layer, the driving voltage, light emitting efficiency, and service life characteristics of the organic light emitting device can be improved.

The invention claimed is:
1. A compound of Formula 1:

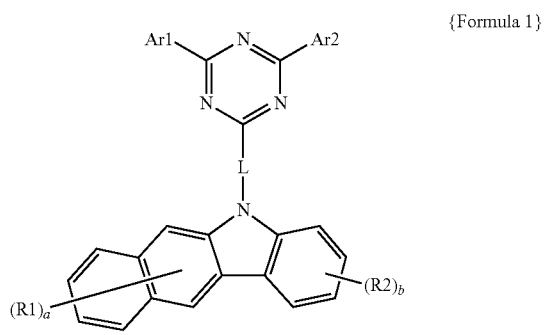

{Formula 1} wherein in Formula 1:
L is a direct bond or a phenylene group; and
one of Ar1 and Ar2 is a substituted or unsubstituted aryl group having 6 to 15 carbon atoms, and the other is a substituent of Formula 2:

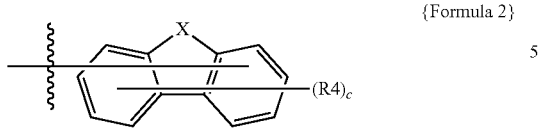

{Formula 2} wherein in Formulae 1 and 2:
X is S or NR3;
R1 is hydrogen, deuterium, a halogen group, a substituted or unsubstituted silyl group, a substituted or unsubstituted alkyl group, a substituted or unsubstituted amine group, a substituted or unsubstituted arylamine group, a substituted or unsubstituted alkylamine group, a substituted or unsubstituted aryl group, or a substituted or unsubstituted heterocyclic group;
R2 is hydrogen, deuterium, a halogen group, a substituted or unsubstituted silyl group, a substituted or unsubstituted alkyl group, or a substituted or unsubstituted amine group;

R3 and R4 are each independently hydrogen, deuterium, a halogen group, a substituted or unsubstituted silyl group, a substituted or unsubstituted alkyl group, a substituted or unsubstituted amine group, a substituted or unsubstituted arylamine group, a substituted or unsubstituted alkylamine group, a substituted or unsubstituted aryl group, or a substituted or unsubstituted heterocyclic group;
a is an integer from 0 to 6;
b is an integer from 0 to 4;
c is an integer from 0 to 7;
when a to c are each 2 or more, two or more substituents in the parenthesis are the same as or different from each other; and
when c is 2 or more, adjacent R4's are optionally bonded to each other to form a ring.

2. The compound of claim 1, wherein R3 is a substituted or unsubstituted aryl group.

3. The compound of claim 1, wherein R1 and R2 are hydrogen.

4. The compound of claim 1, wherein the compound of Formula 1 is selected from among the following compounds:

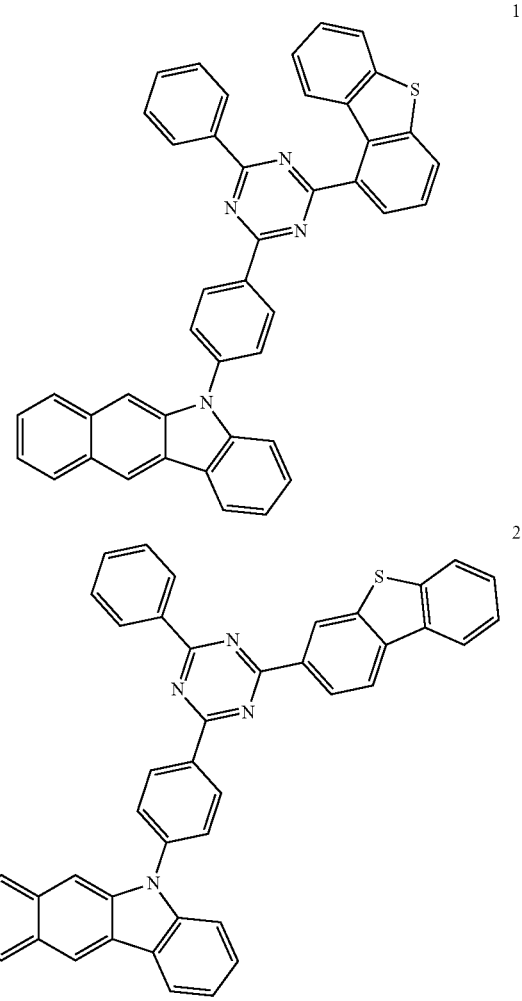

-continued
3
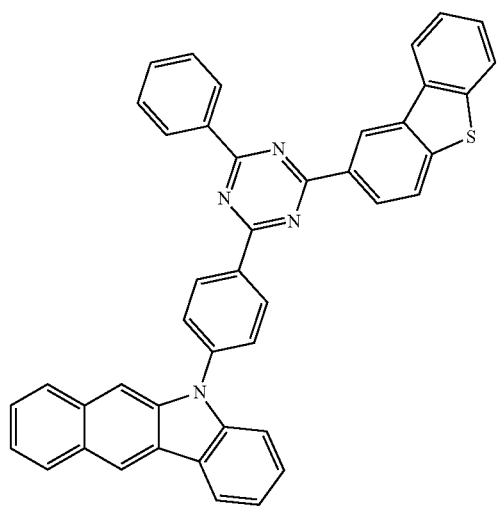
4
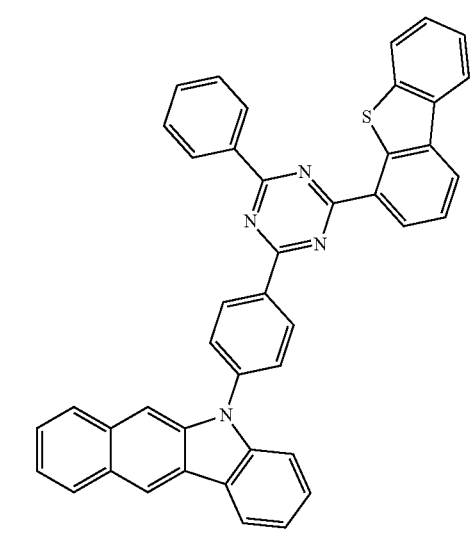
5
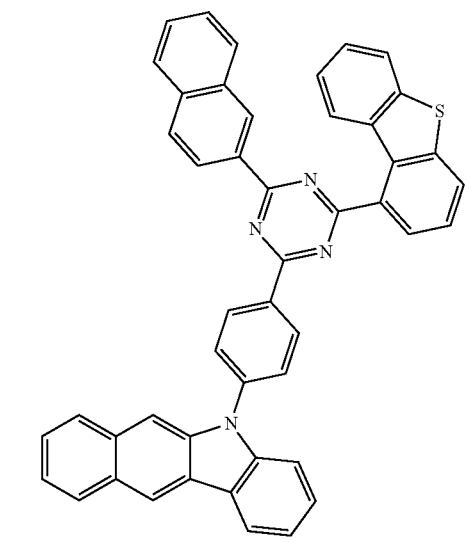
-continued
6
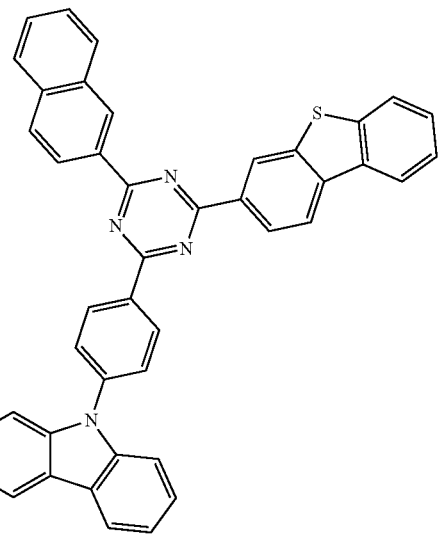
7
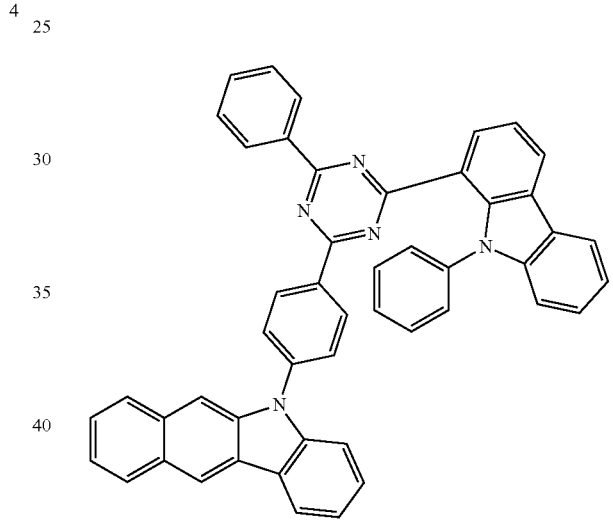
8
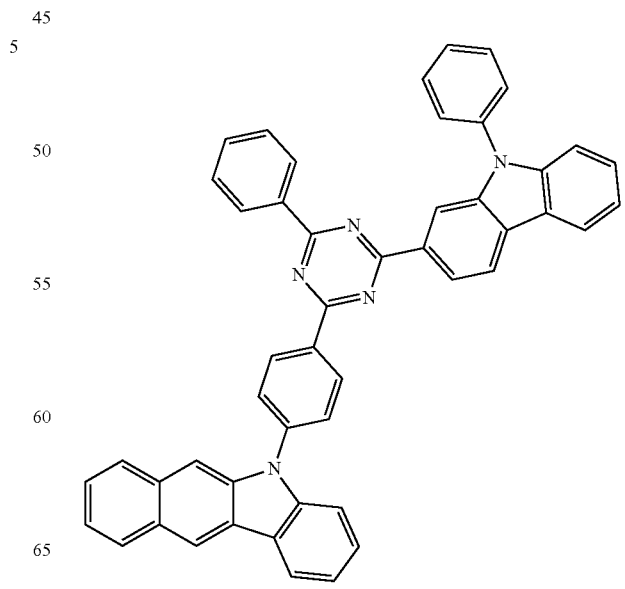

9
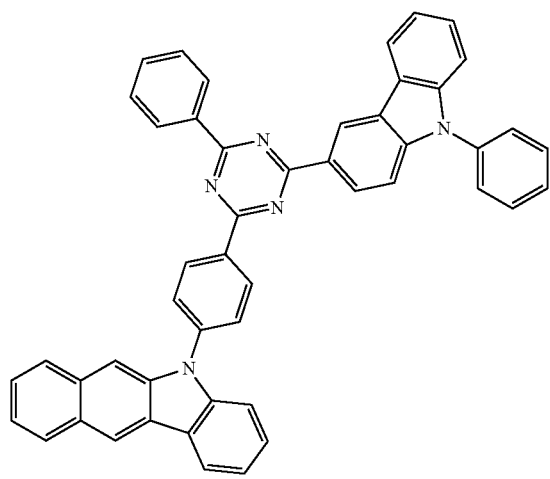
10
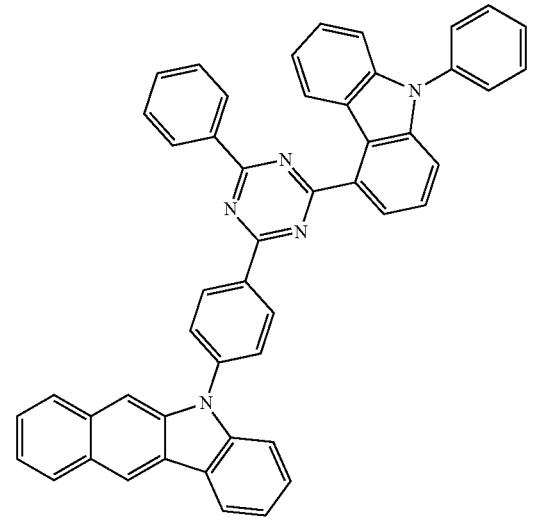
12
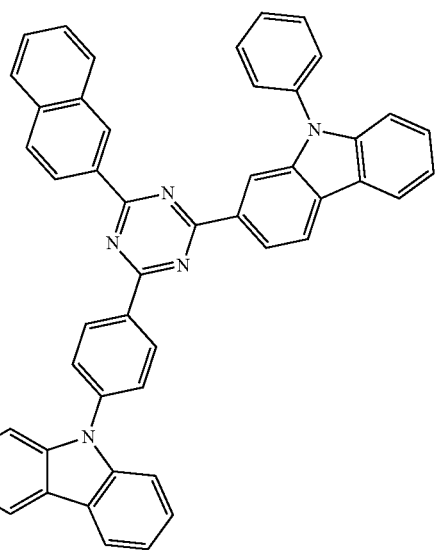
13
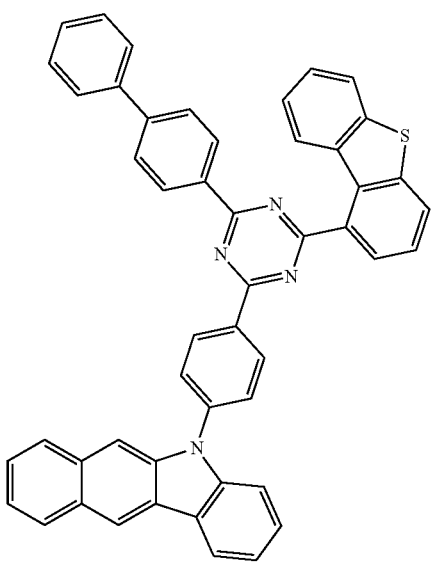

-continued
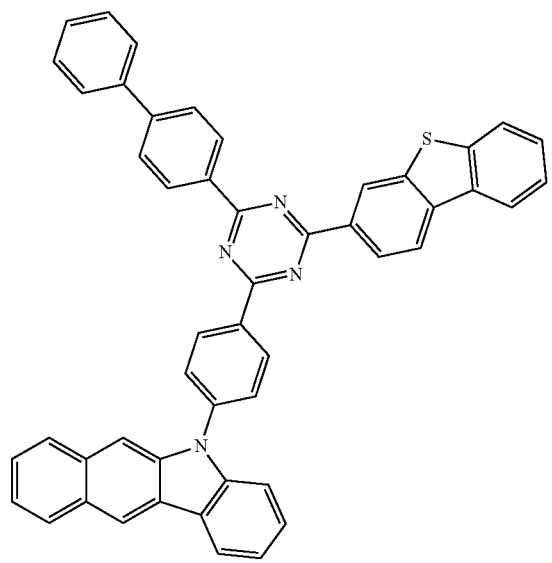
14
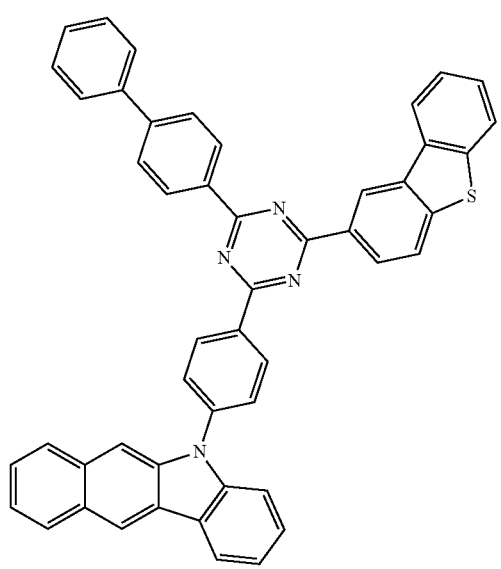
15
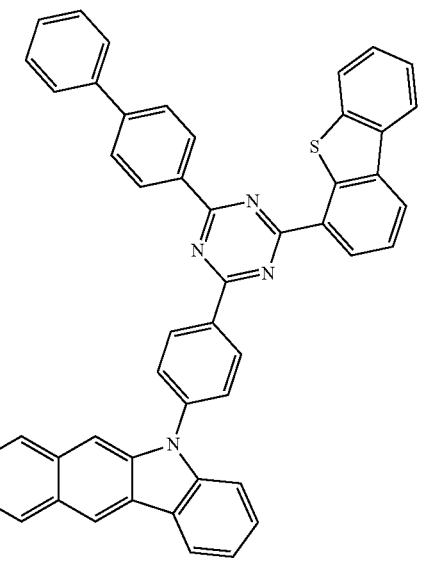
16
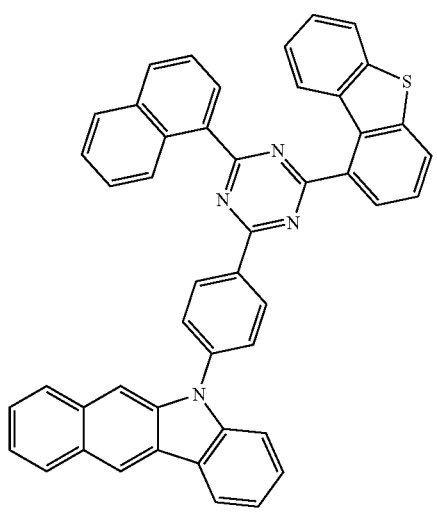
17
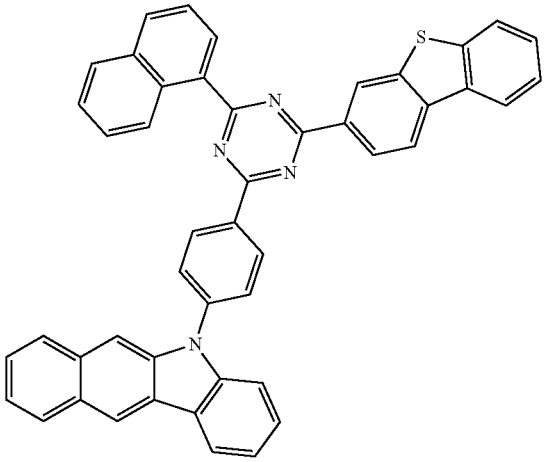
18

-continued
19
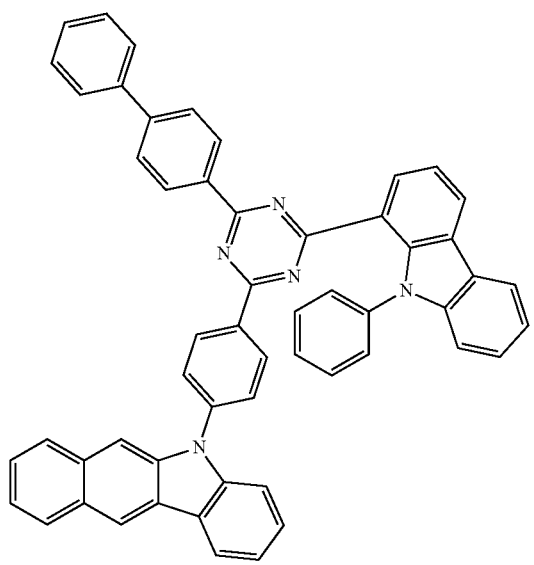
20
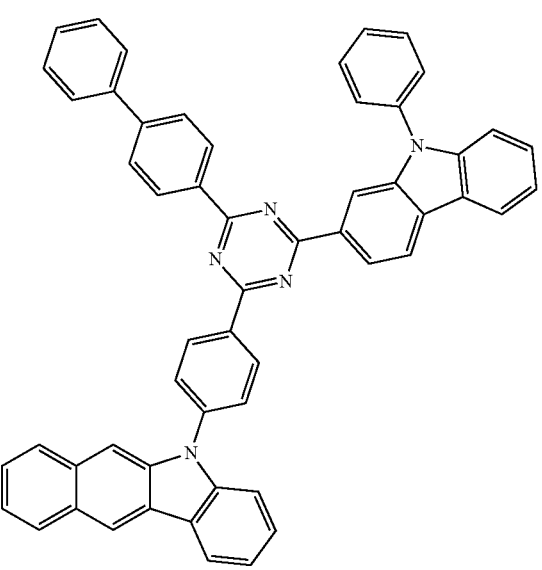
-continued
21
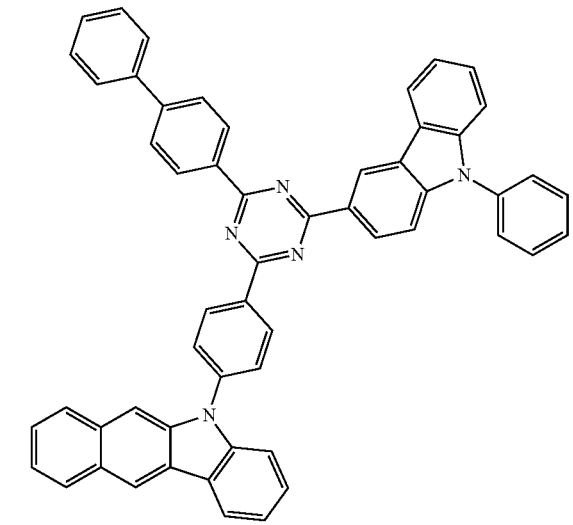
22
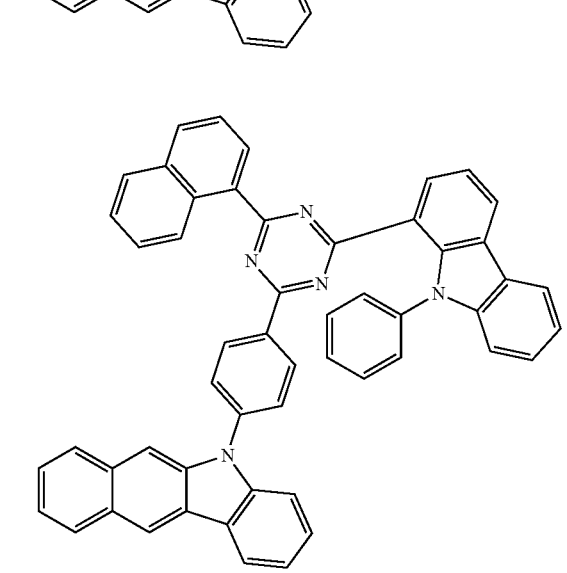
23

-continued
24
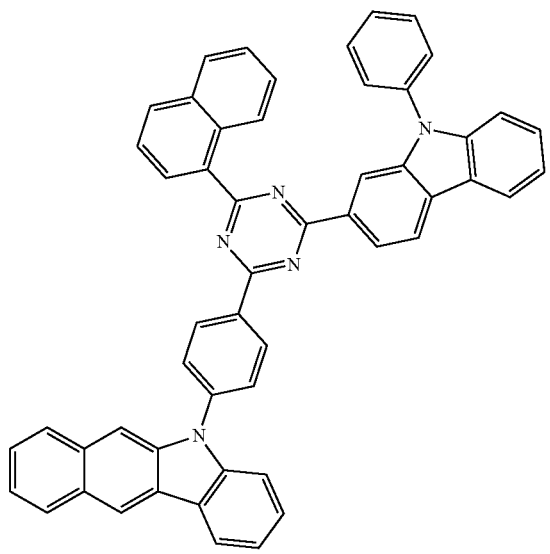
25
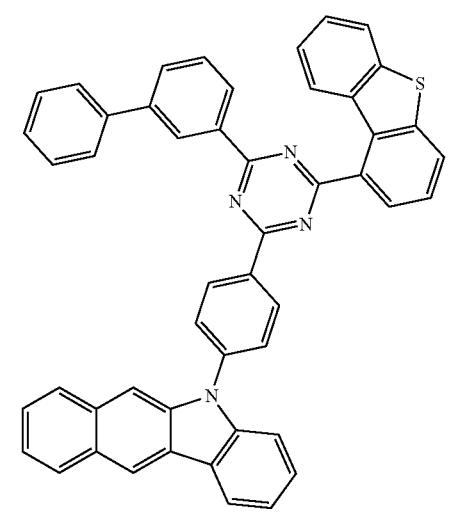
26
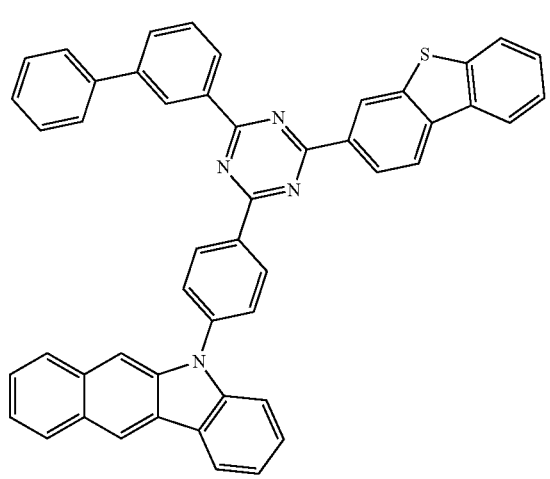
-continued
27
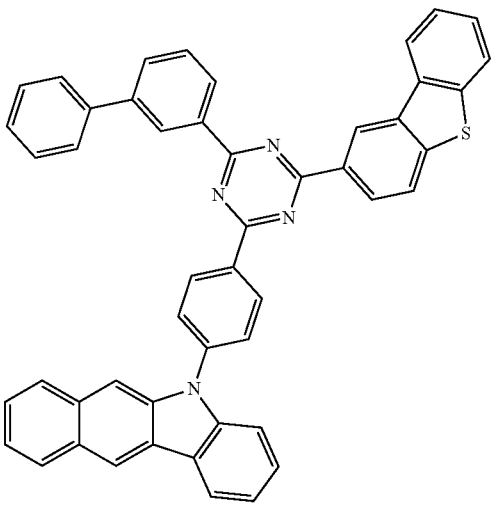
28
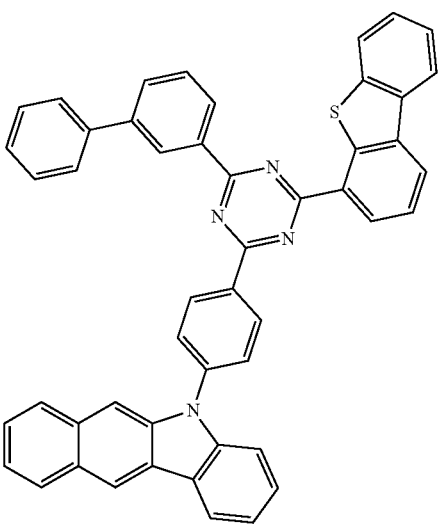
29
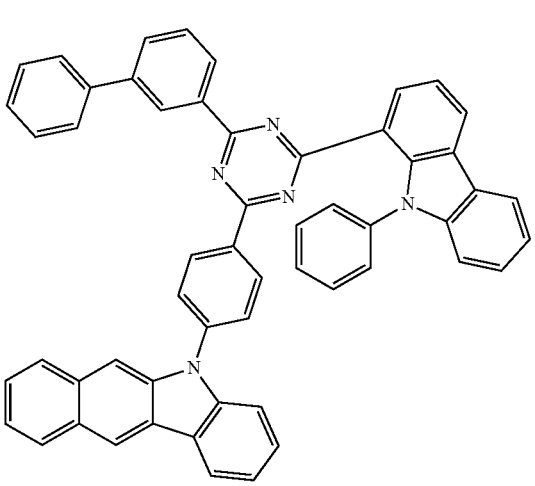

161
30
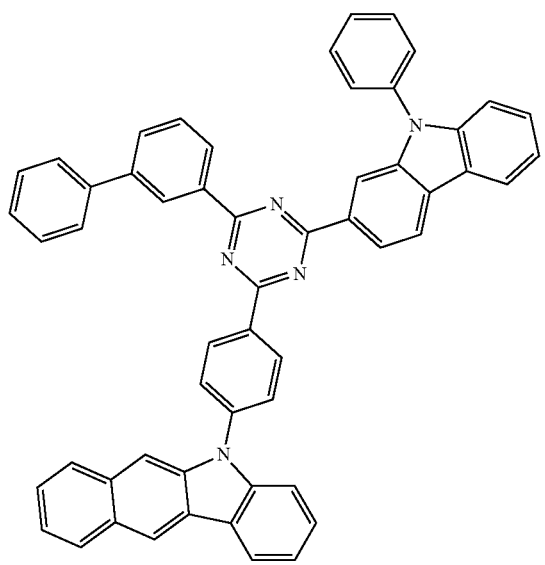
31
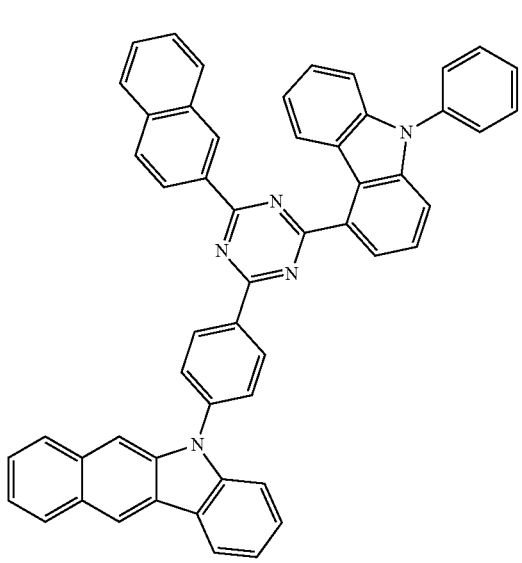
32
162
33
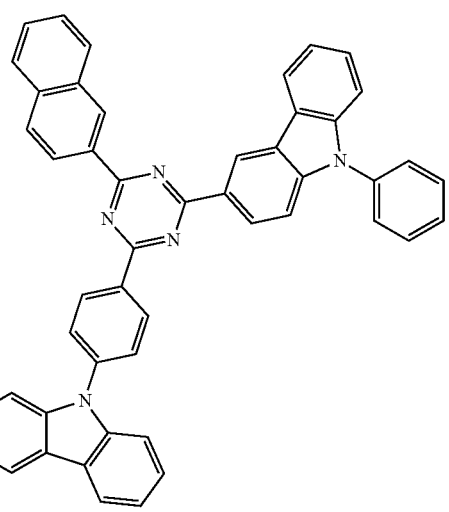
34
35
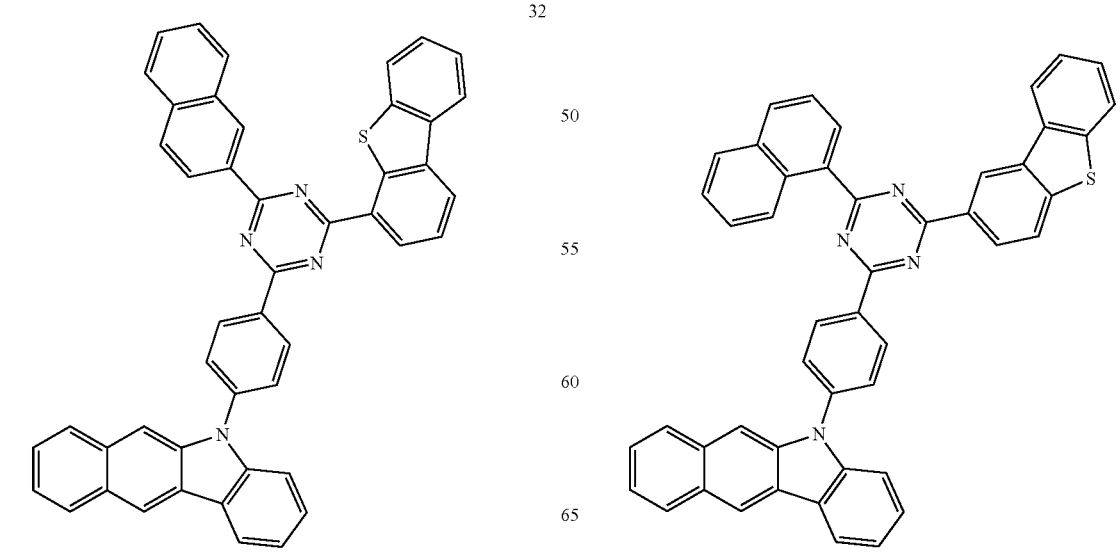

36
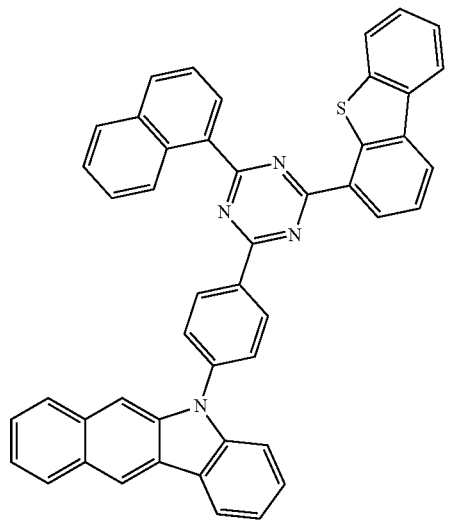
39
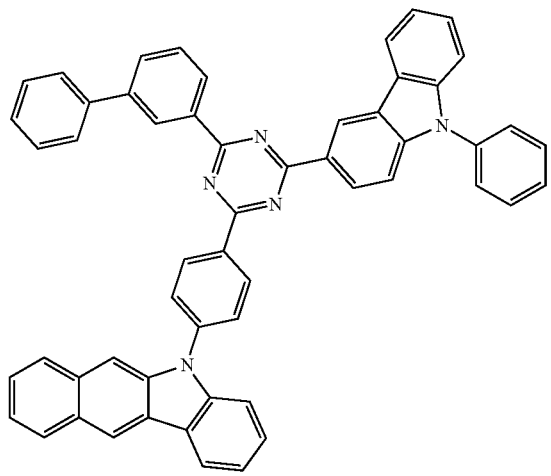
37
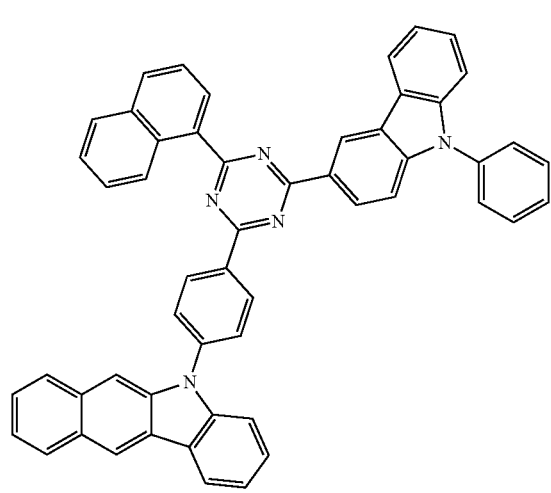
40
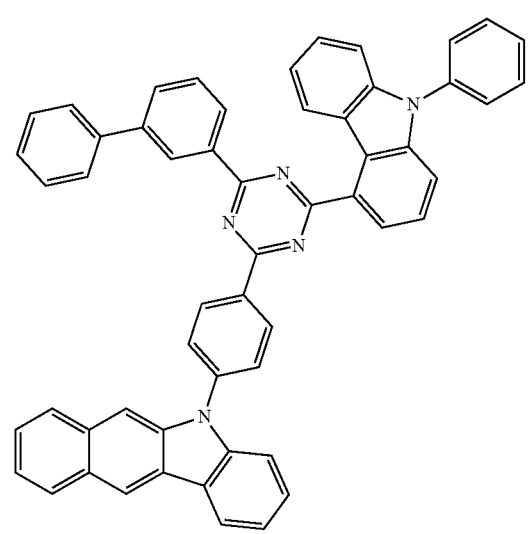
38
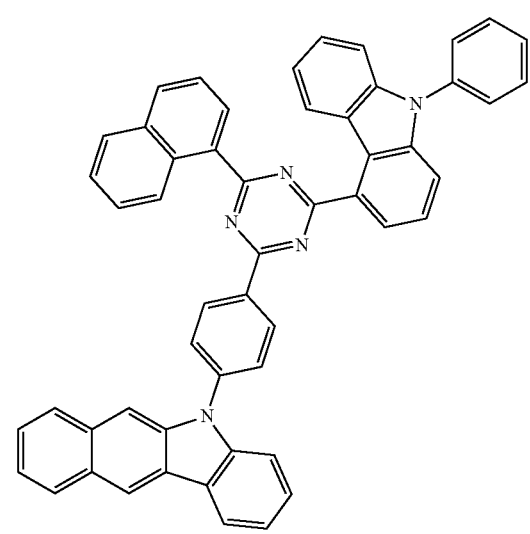
41
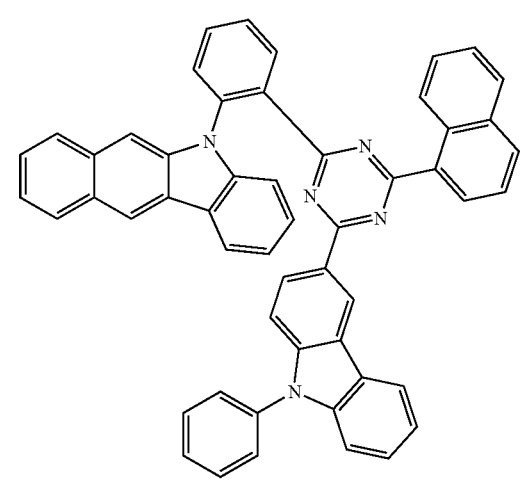

42
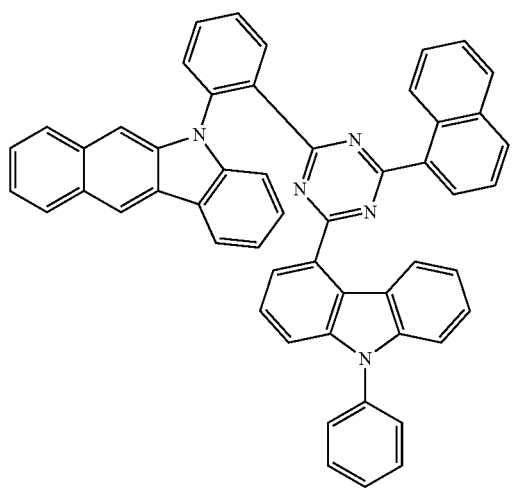
43
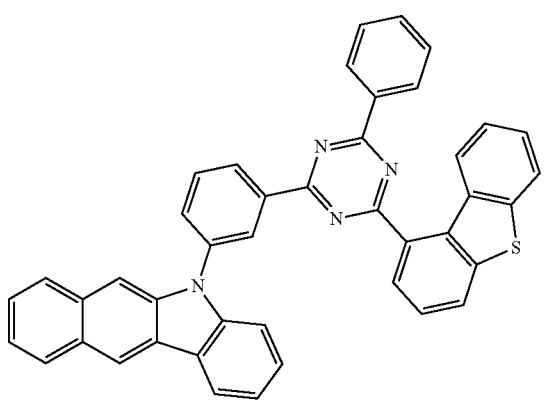
44
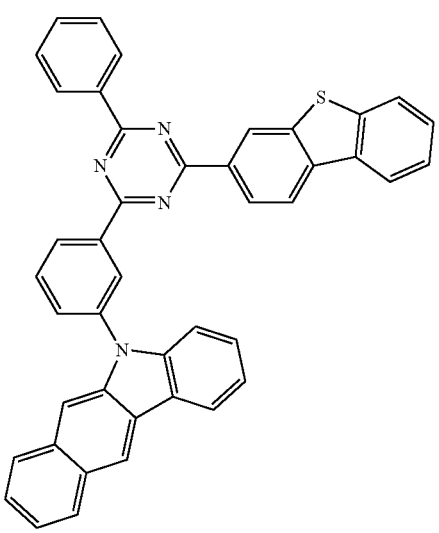
45
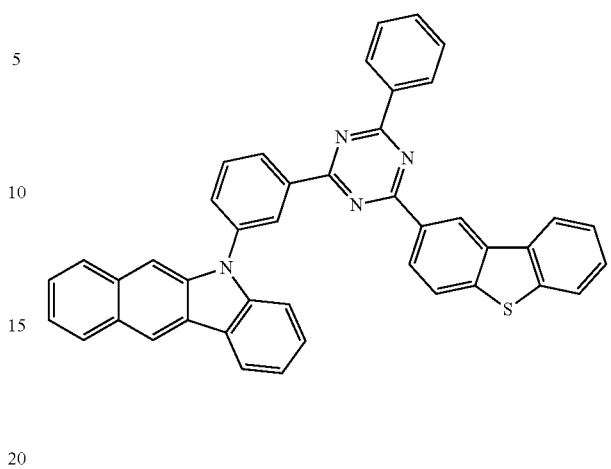
46
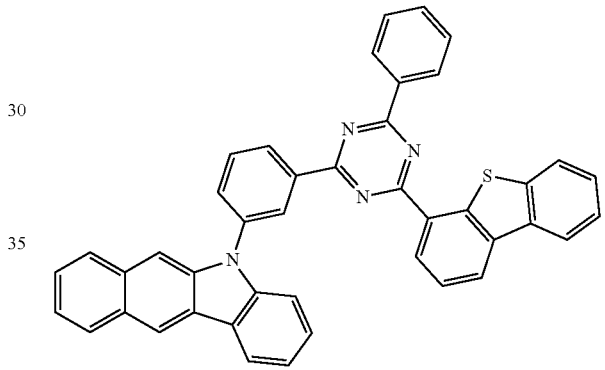
47
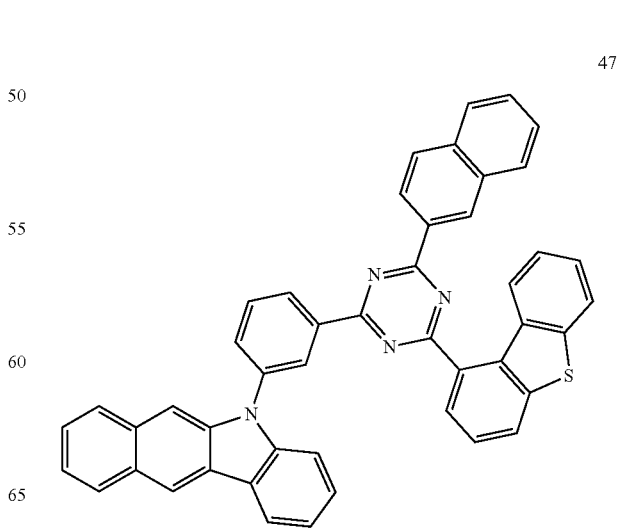

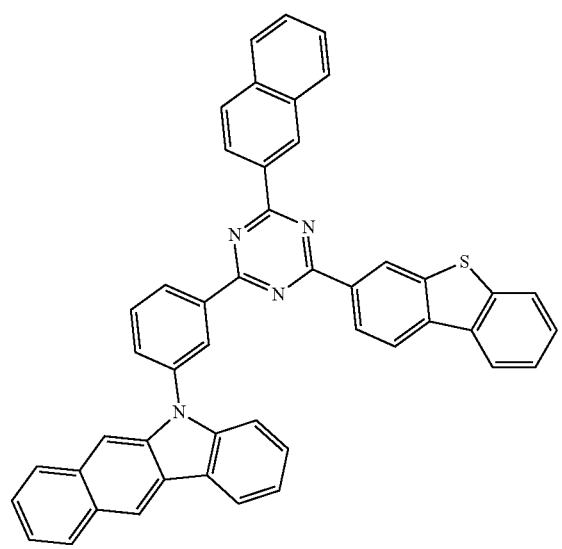
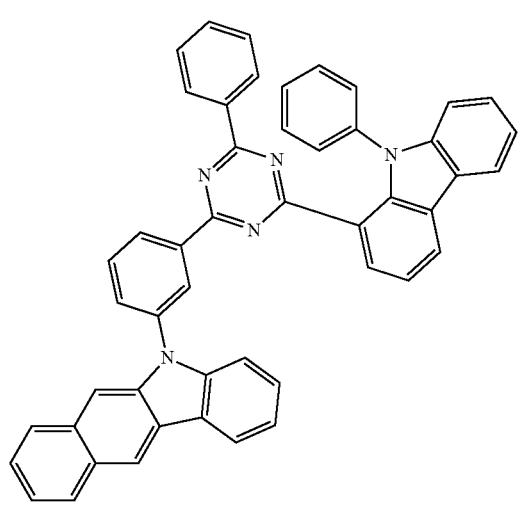
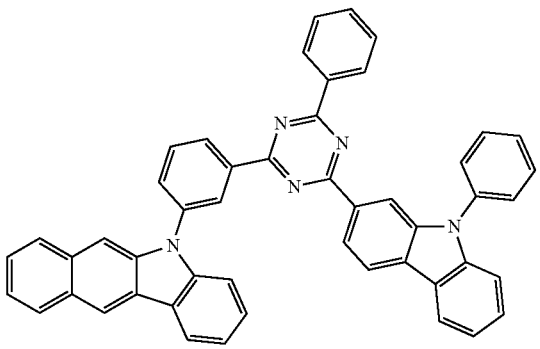
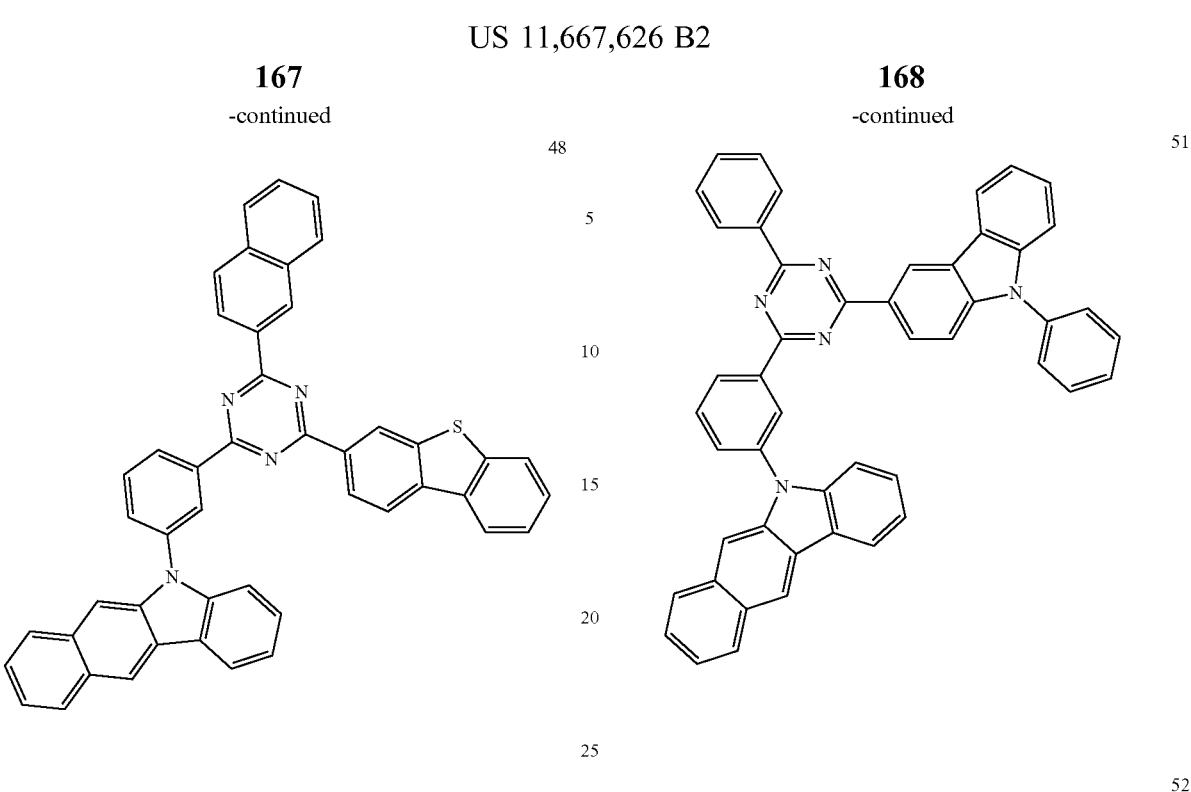

54
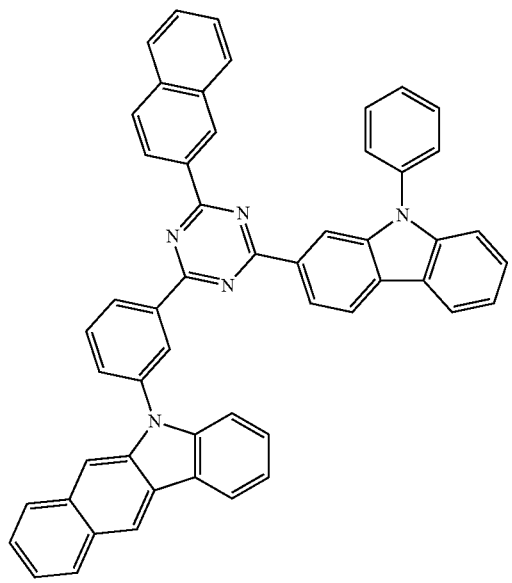
55
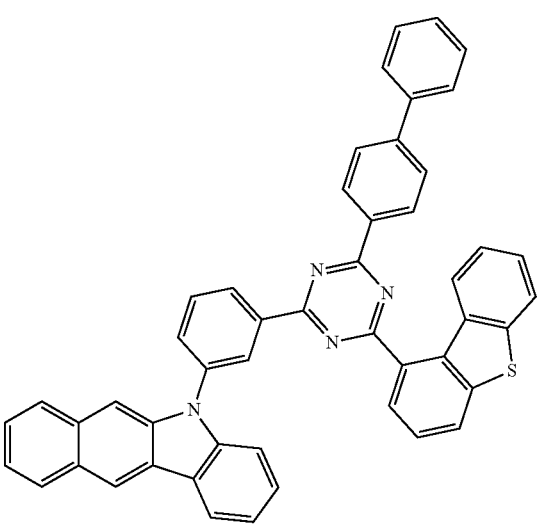
56
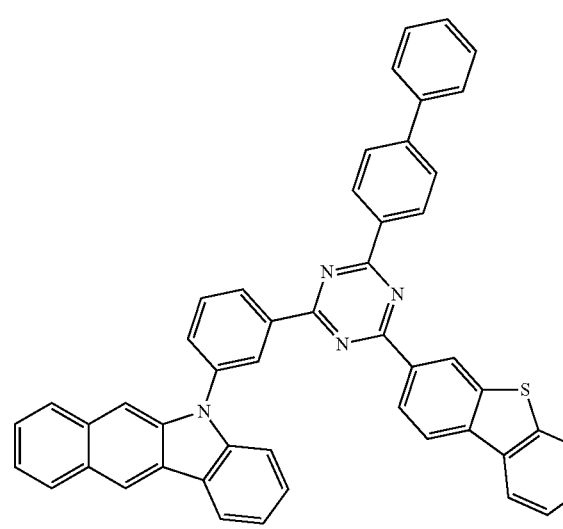
57
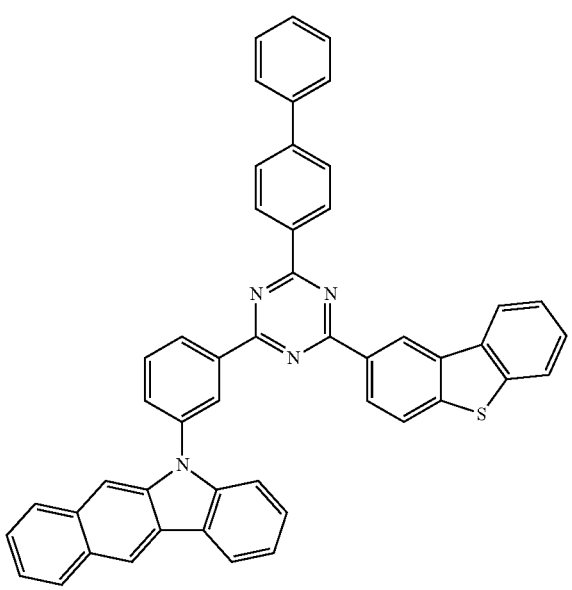
58
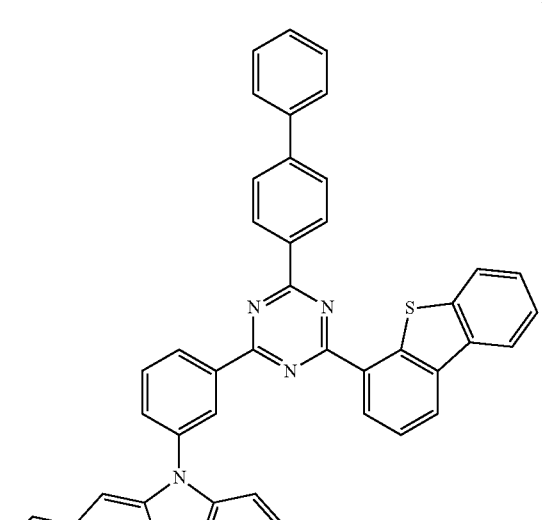
59
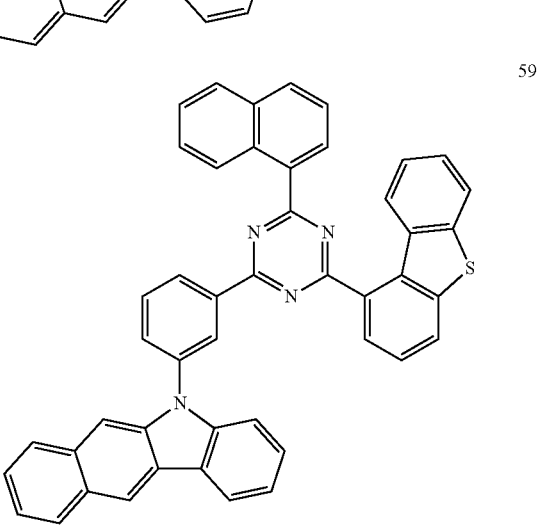

171
-continued
60
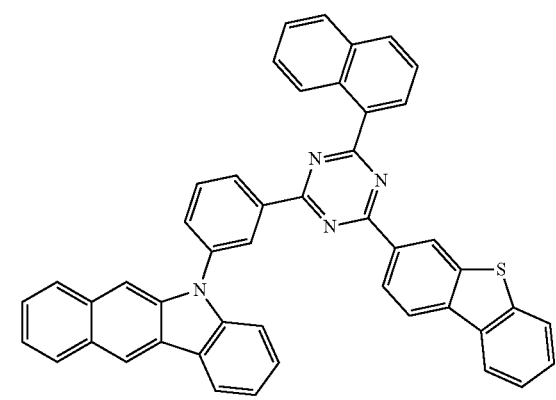
61
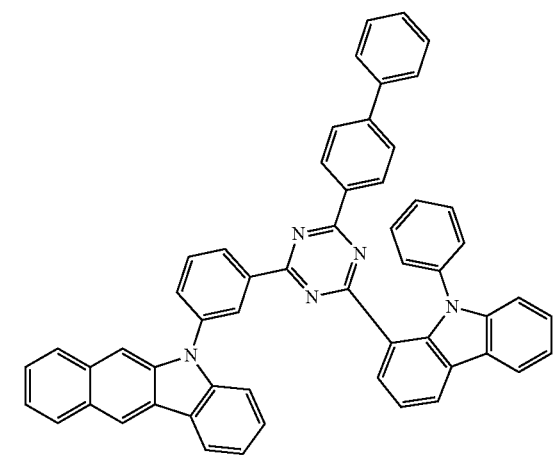
62
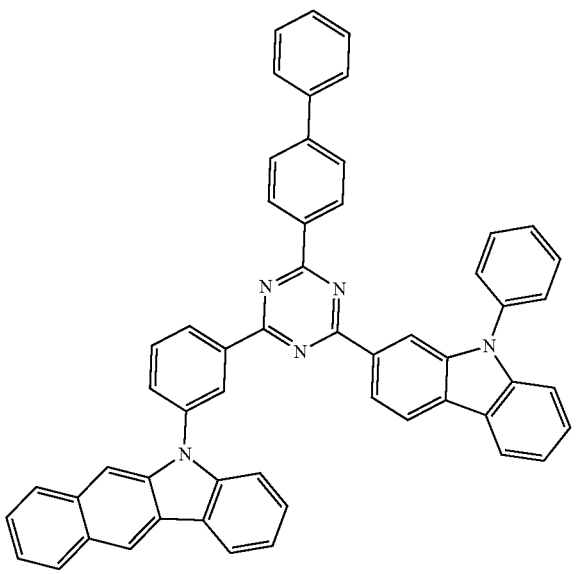
172
-continued
63
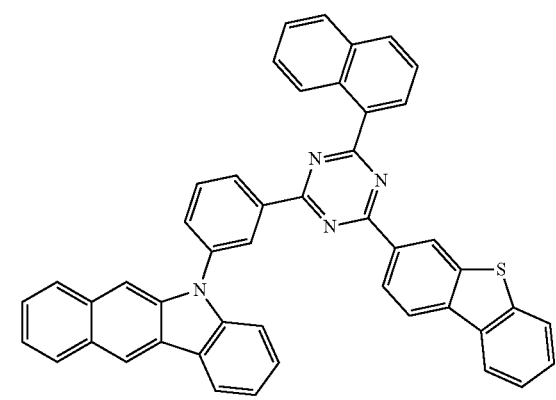
64
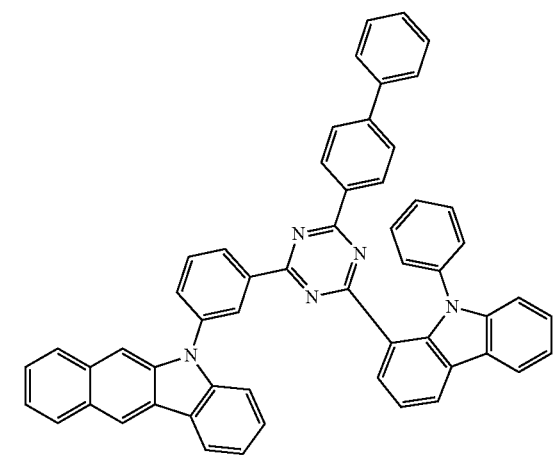
65
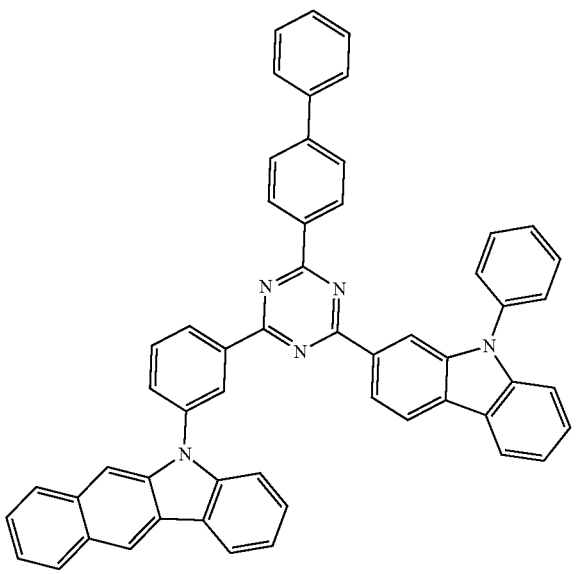

66
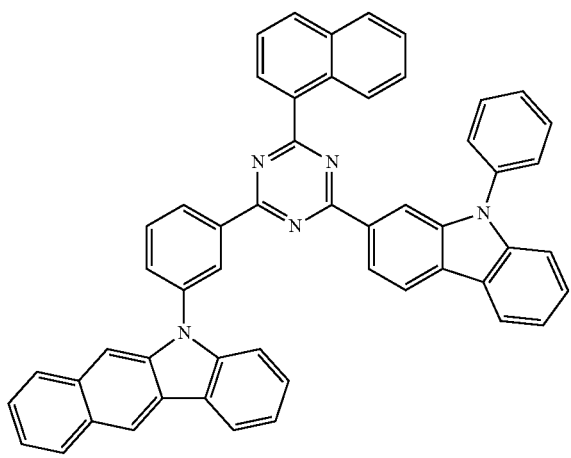
69
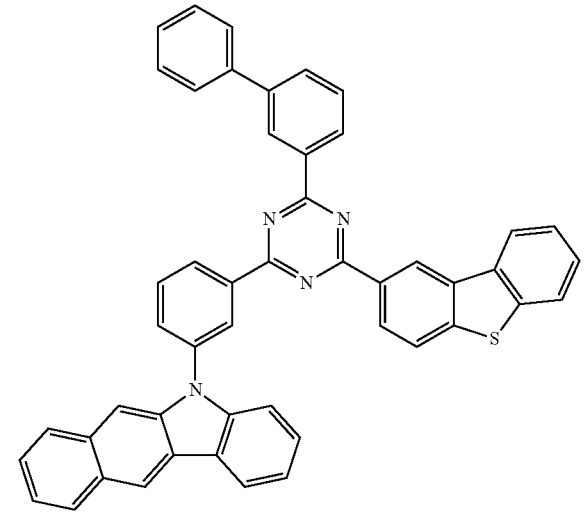
67
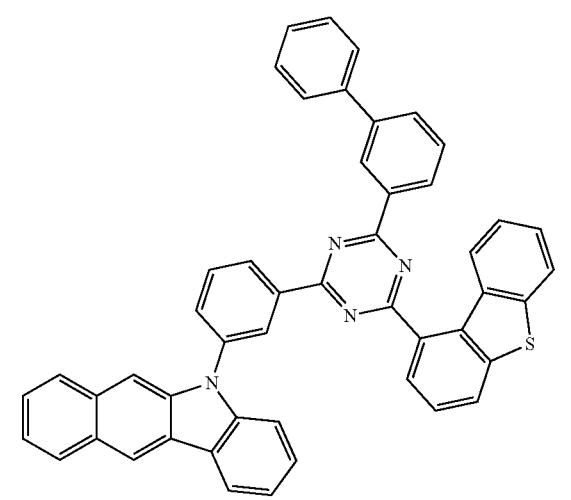
70
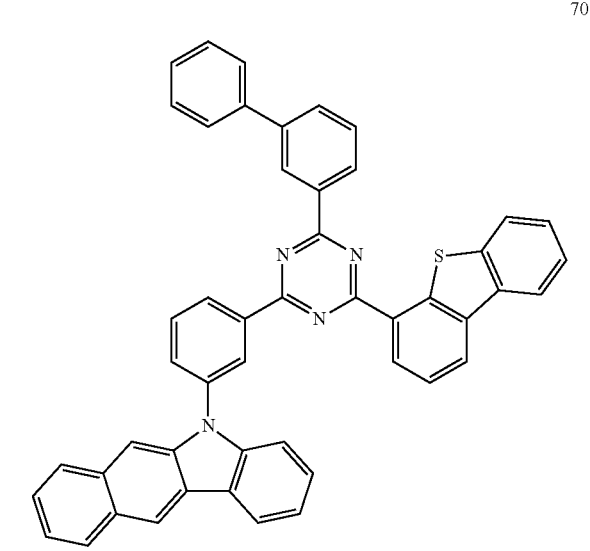
68
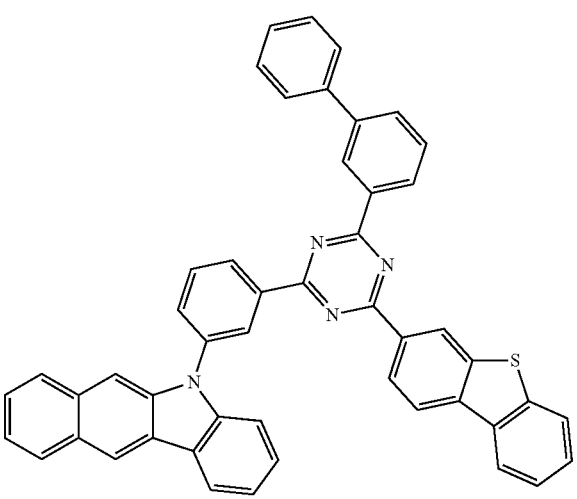
71
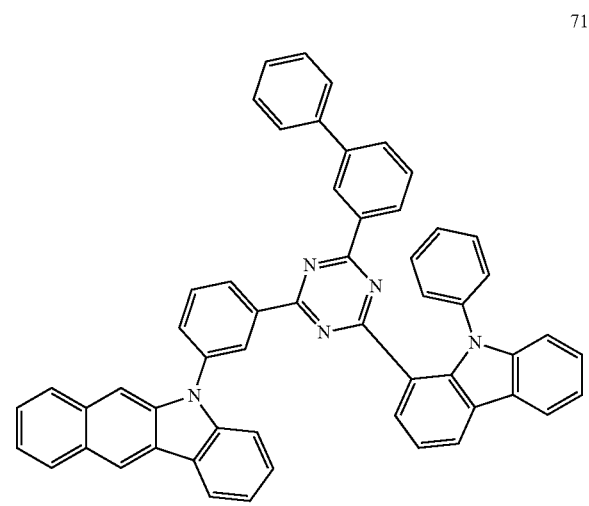

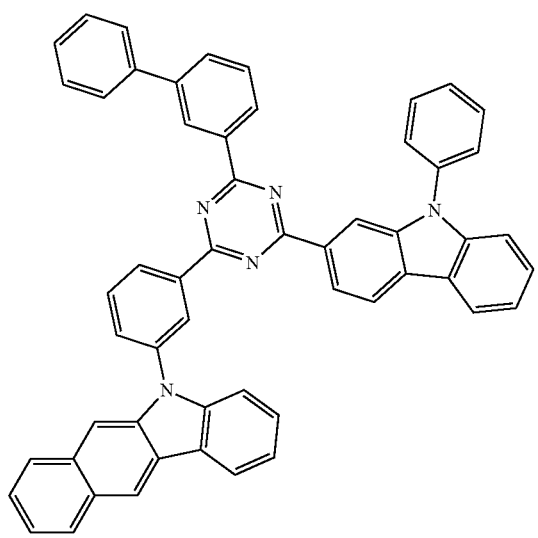
72
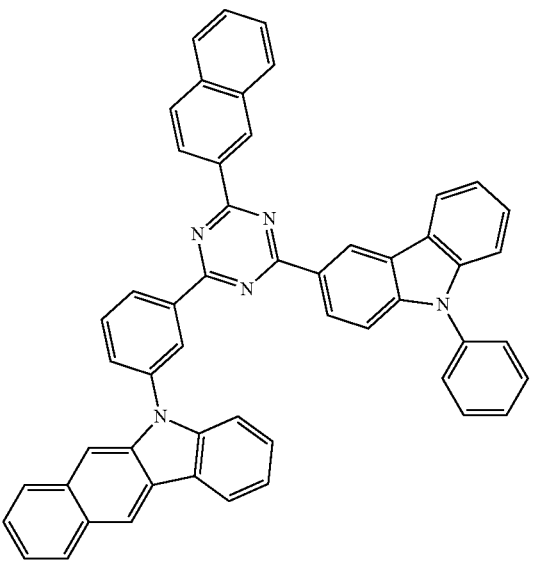
75
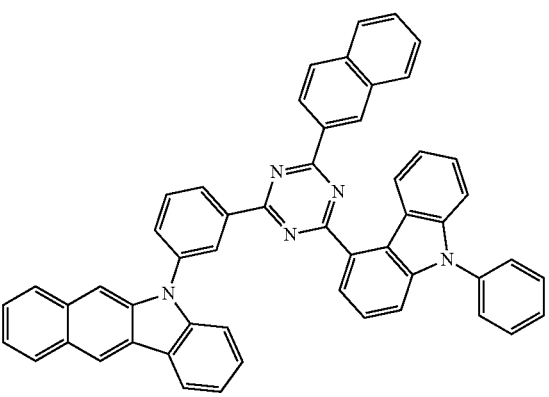
76
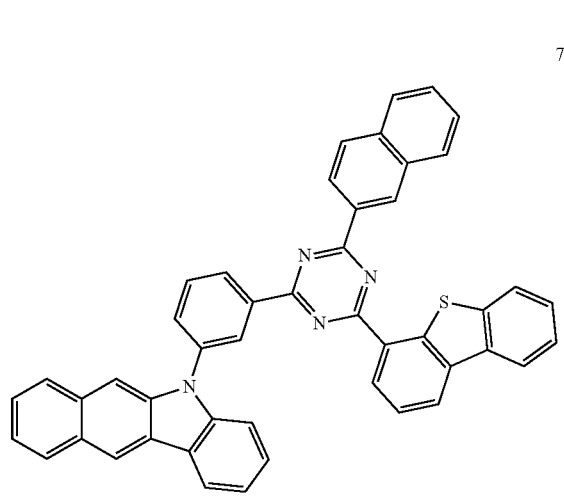
73
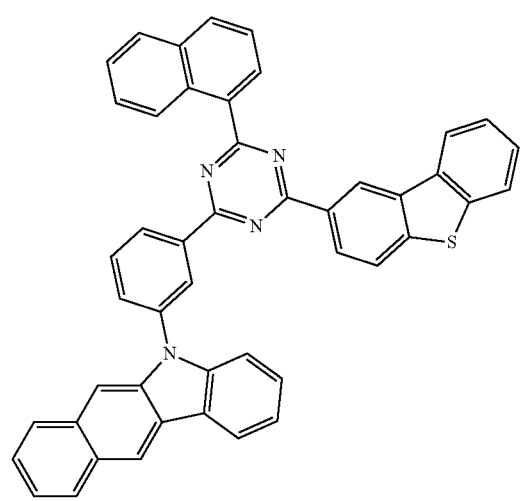
77
74

177
-continued
78
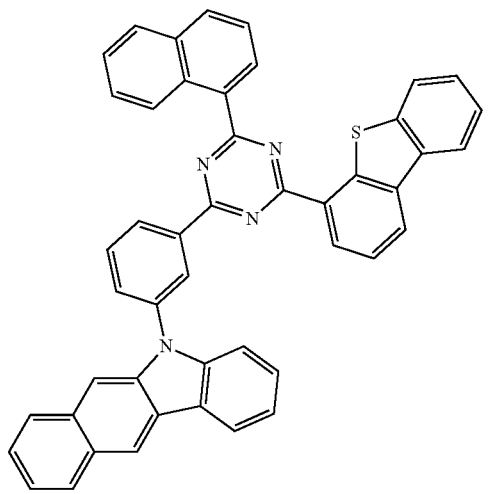
79
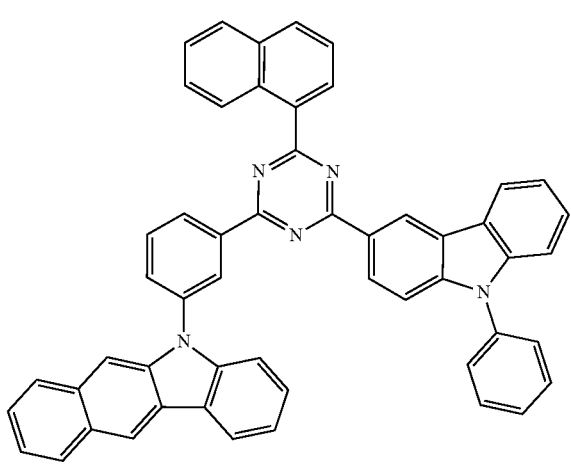
80
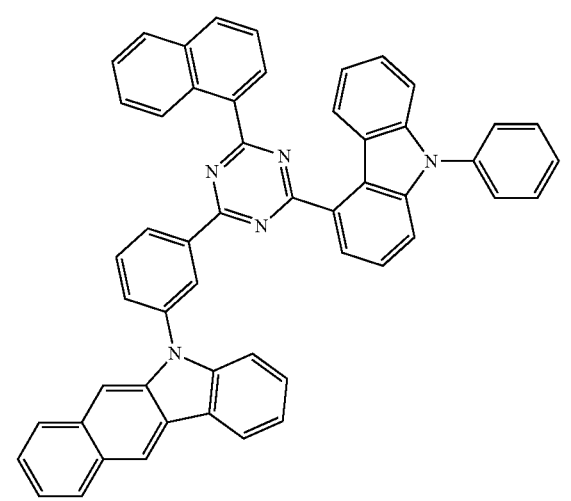
178
-continued
81
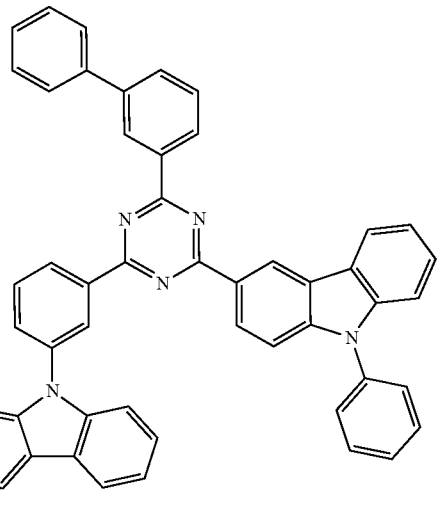
82
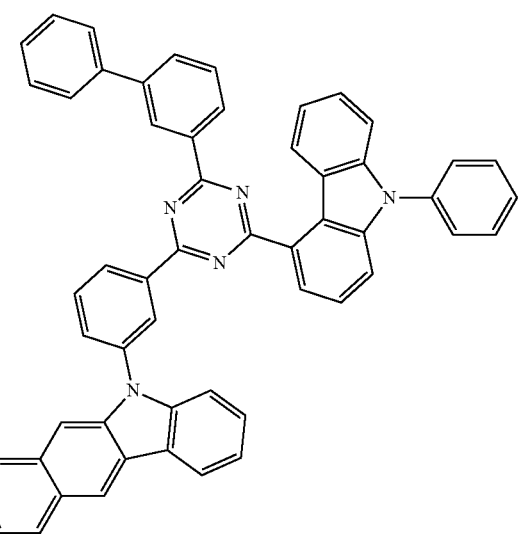
83
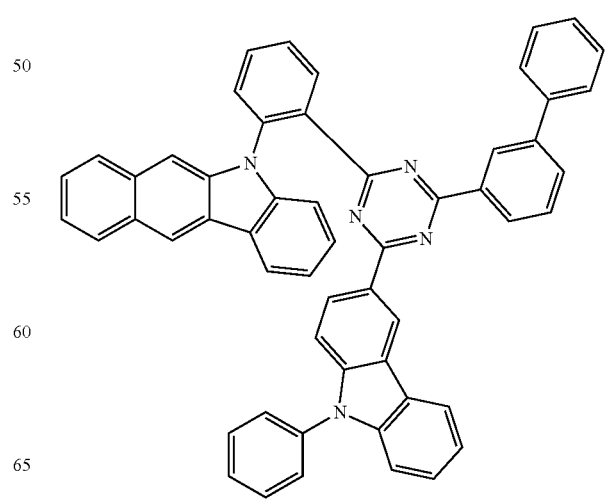

84
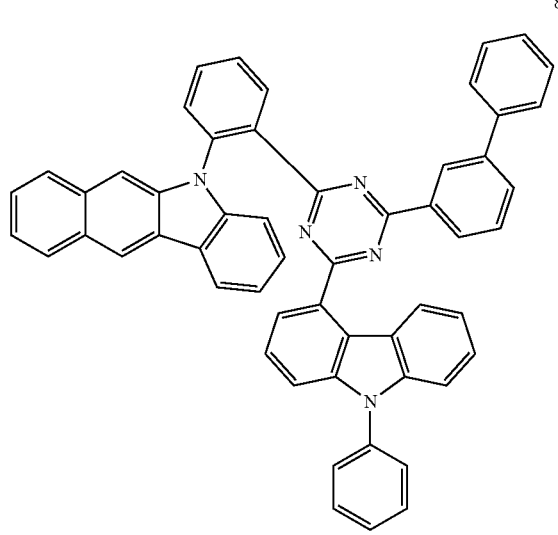
85
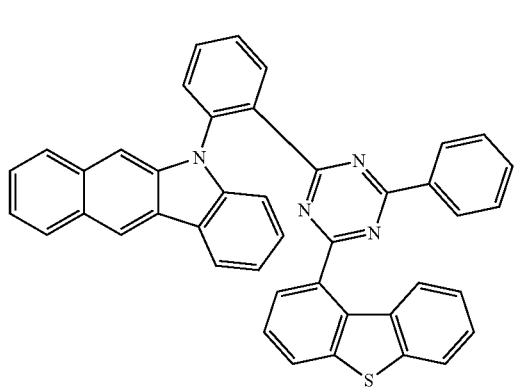
86
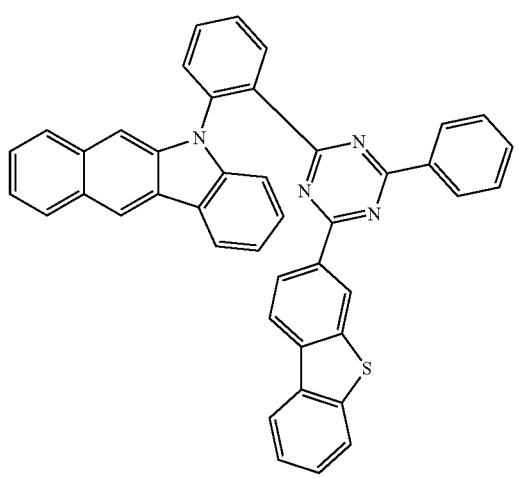
87
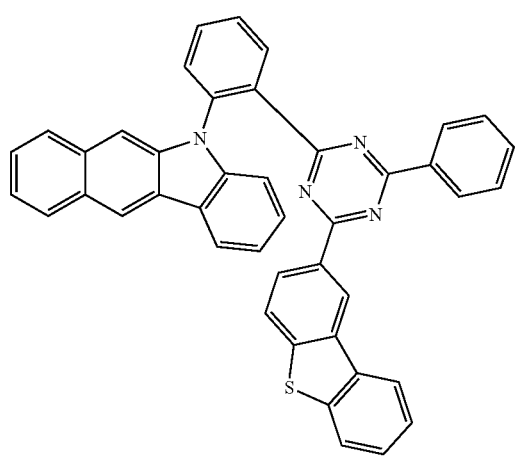
88
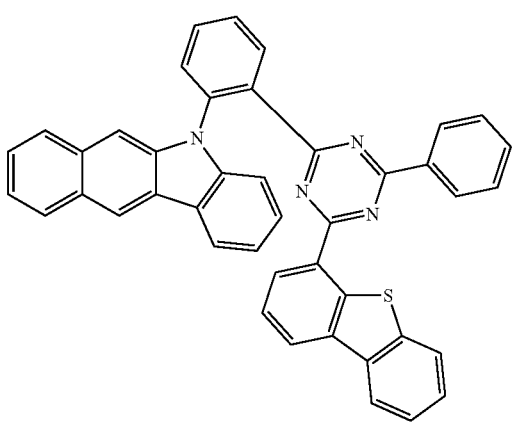
89
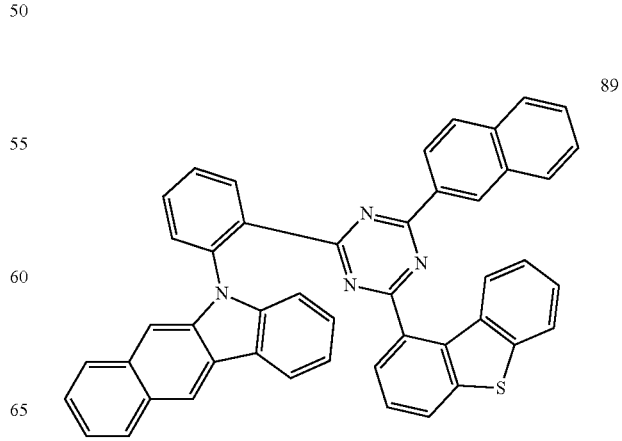

-continued
90
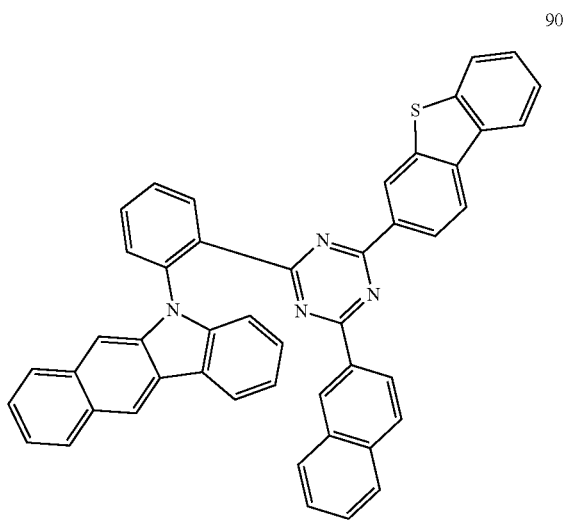
93
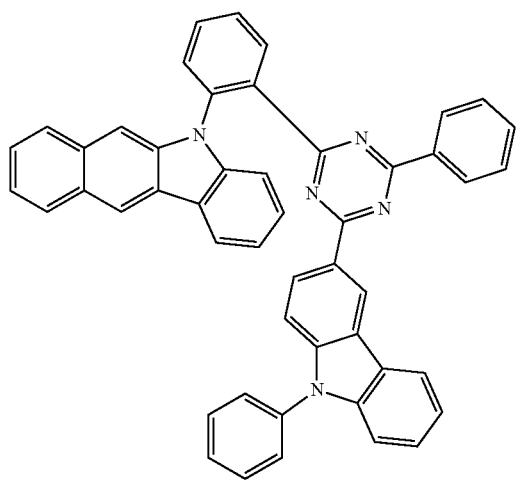
91
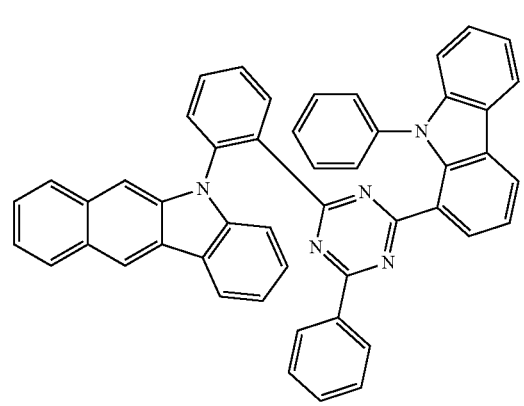
94
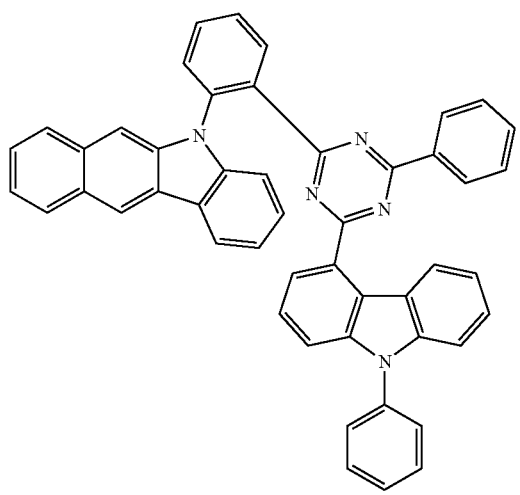
92
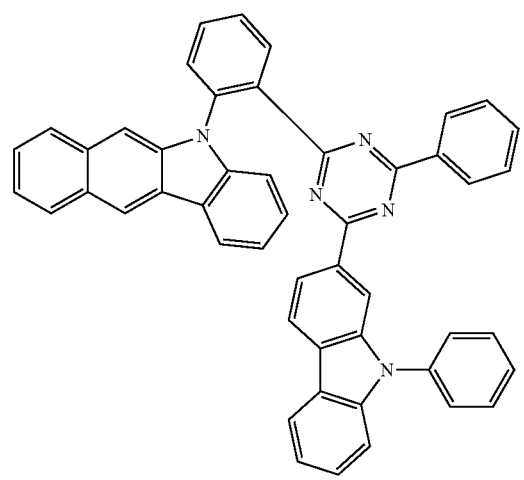
95
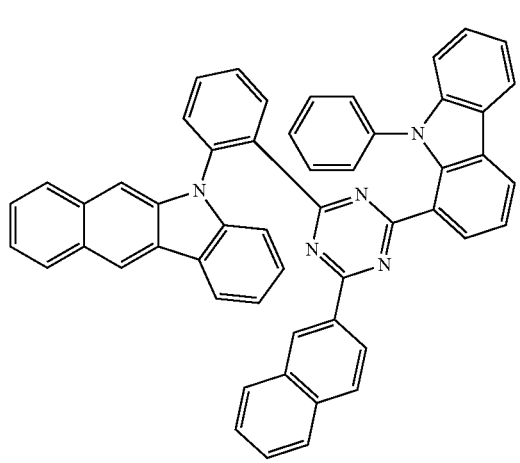

96
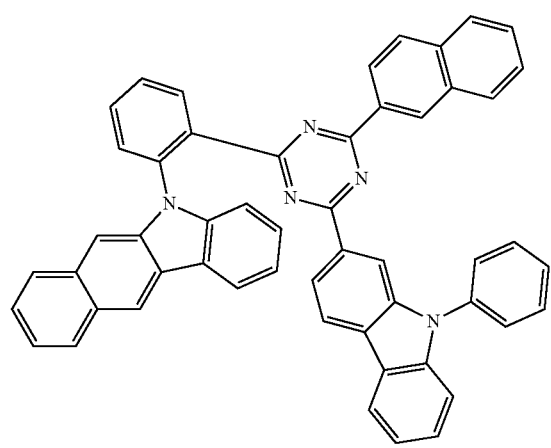
97
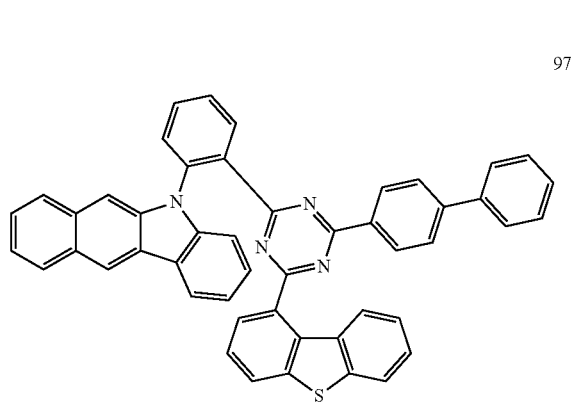
98
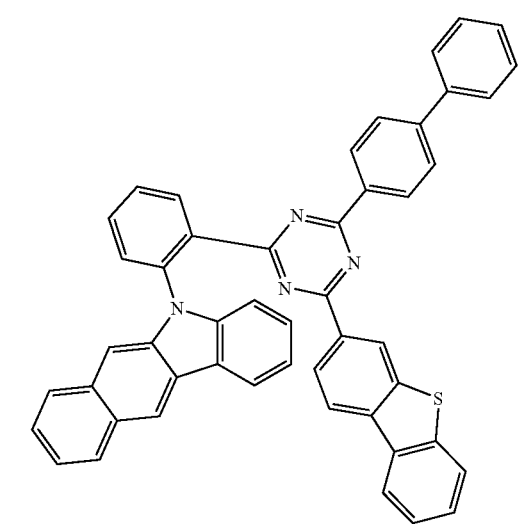
99
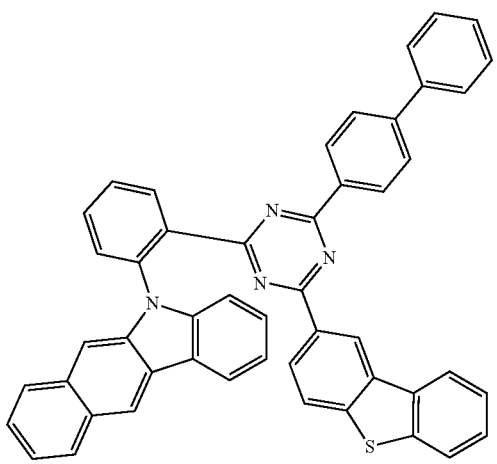
100
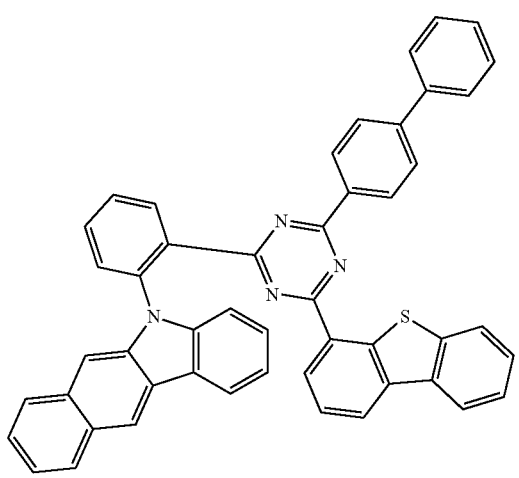
101
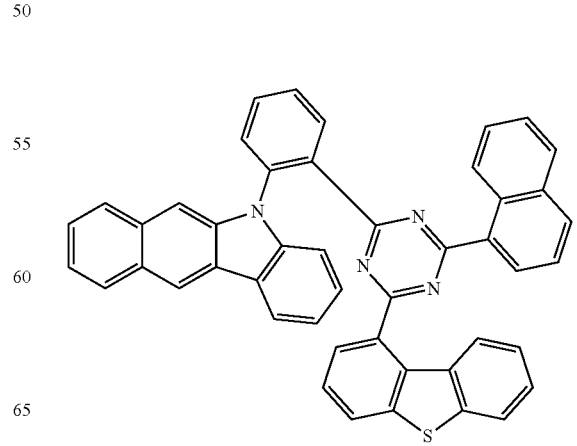

185
-continued
102
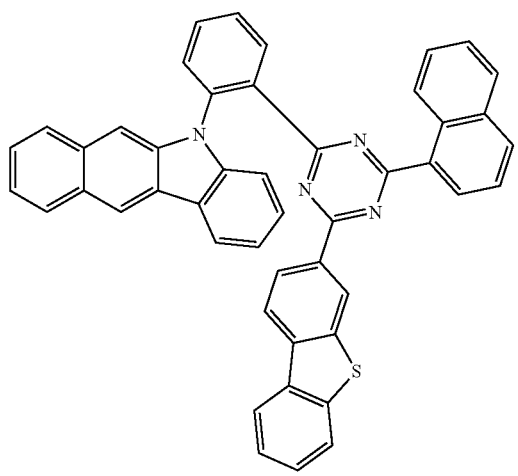
103
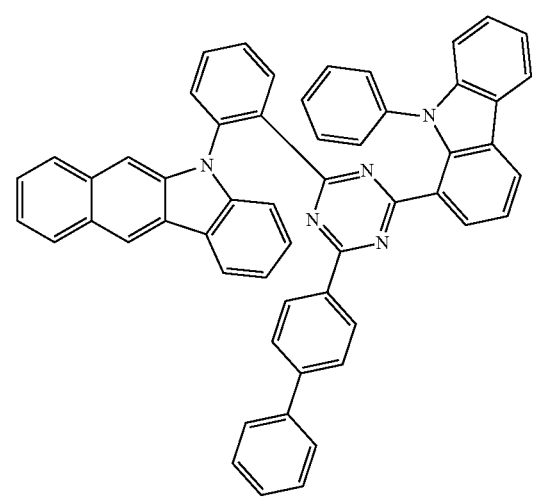
104
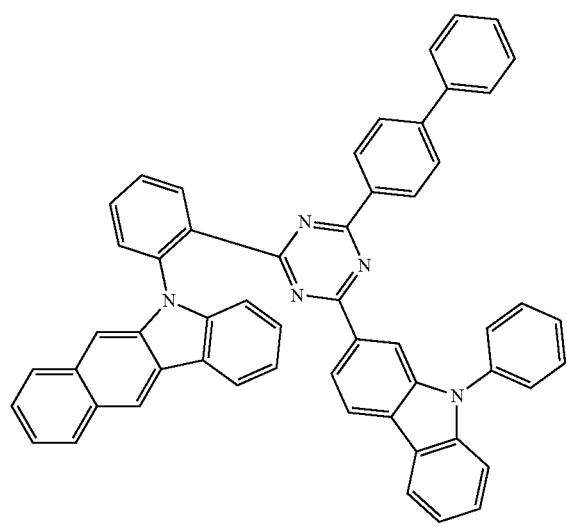
186
-continued
105
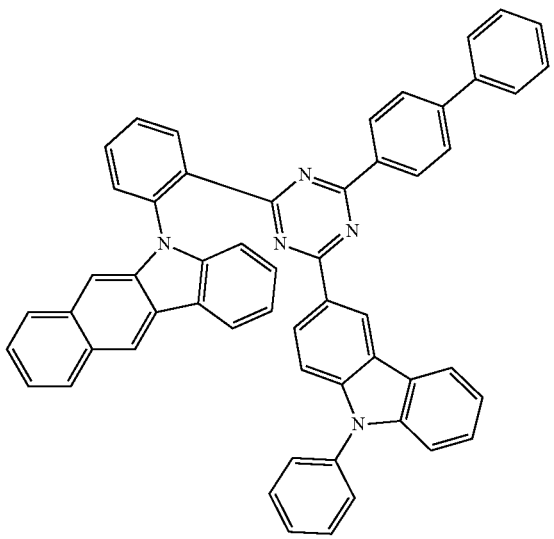
106
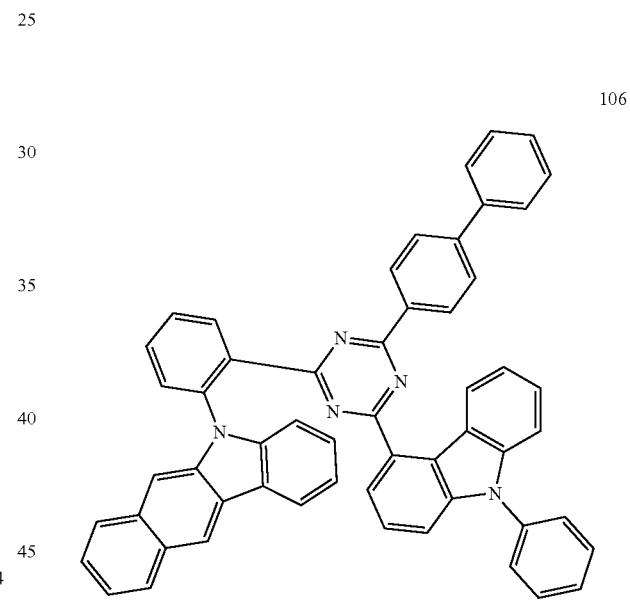
107
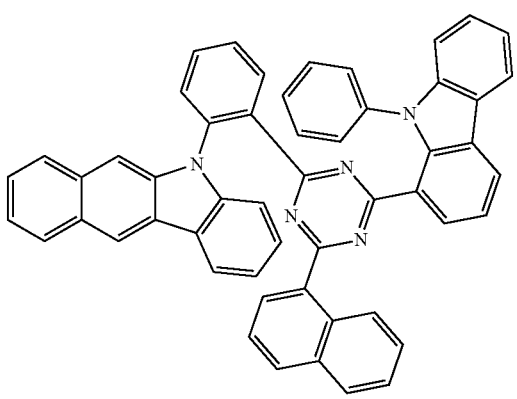

108
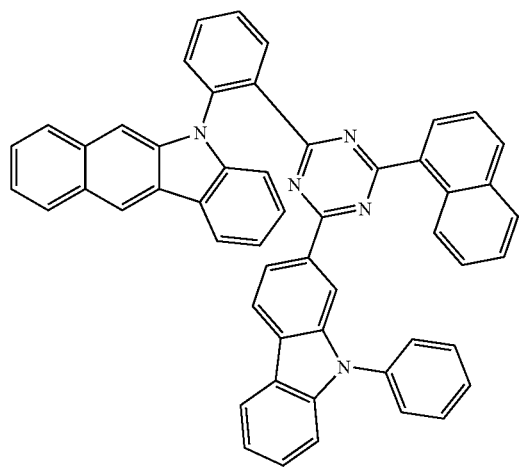
111
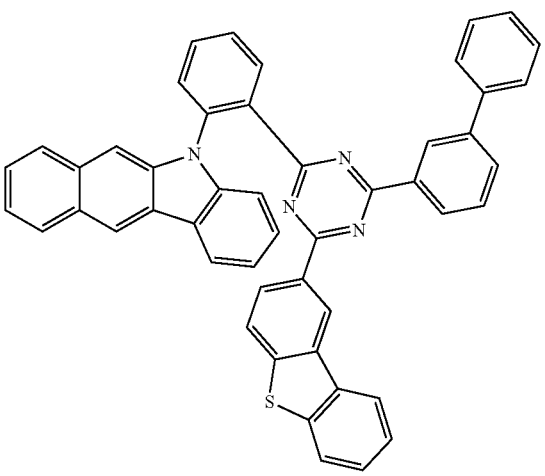
109
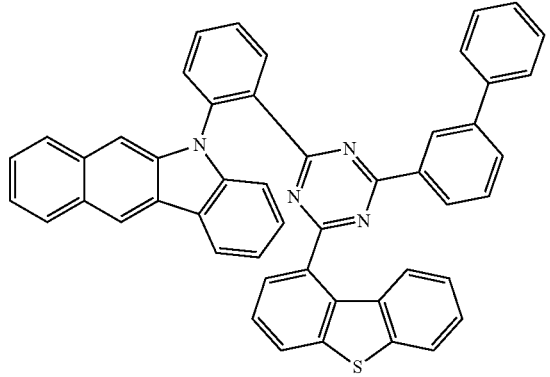
112
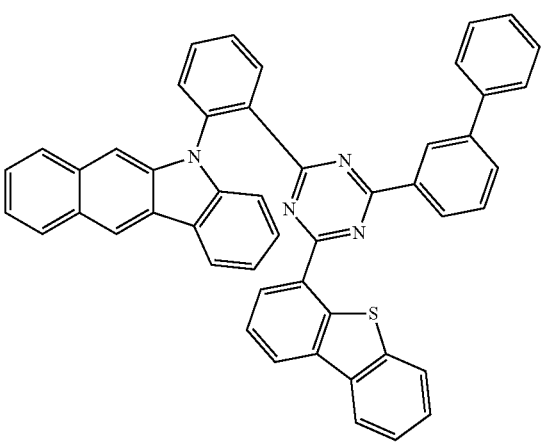
110
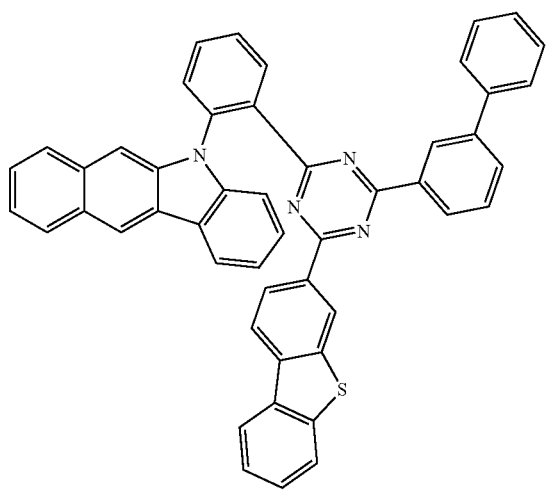
113
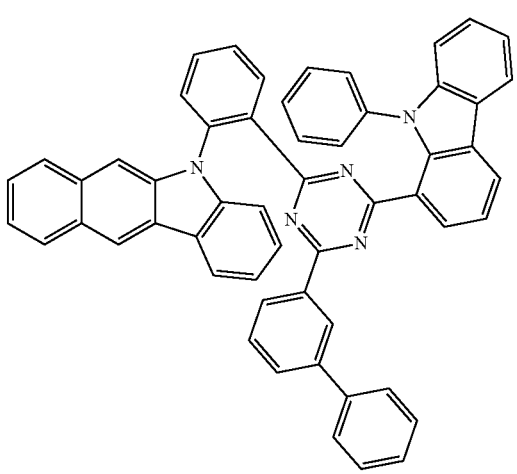

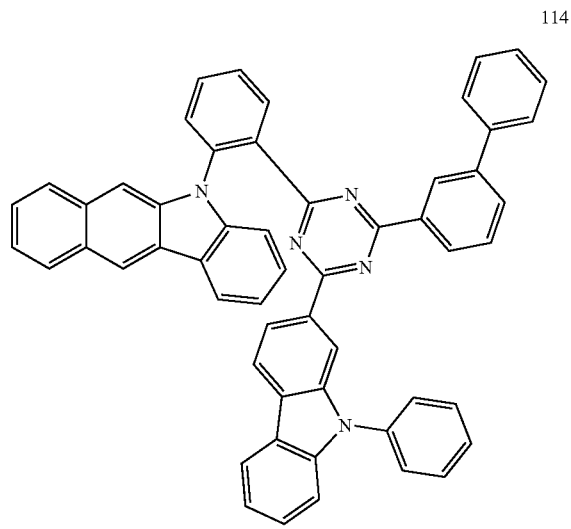
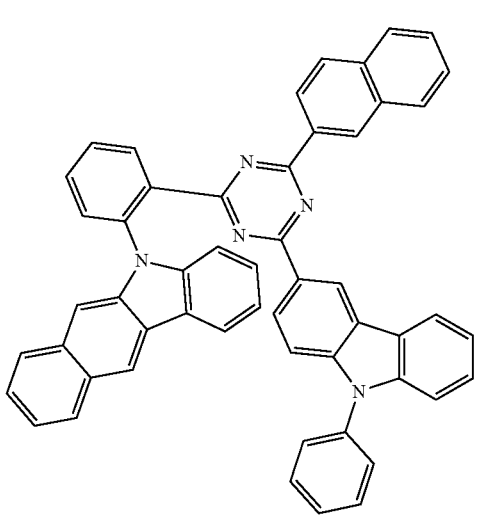
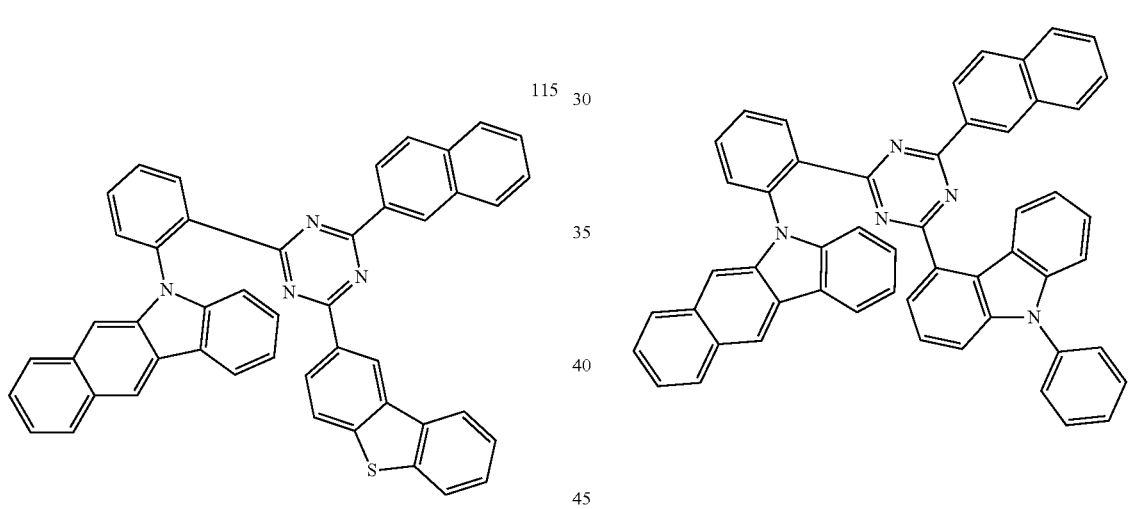
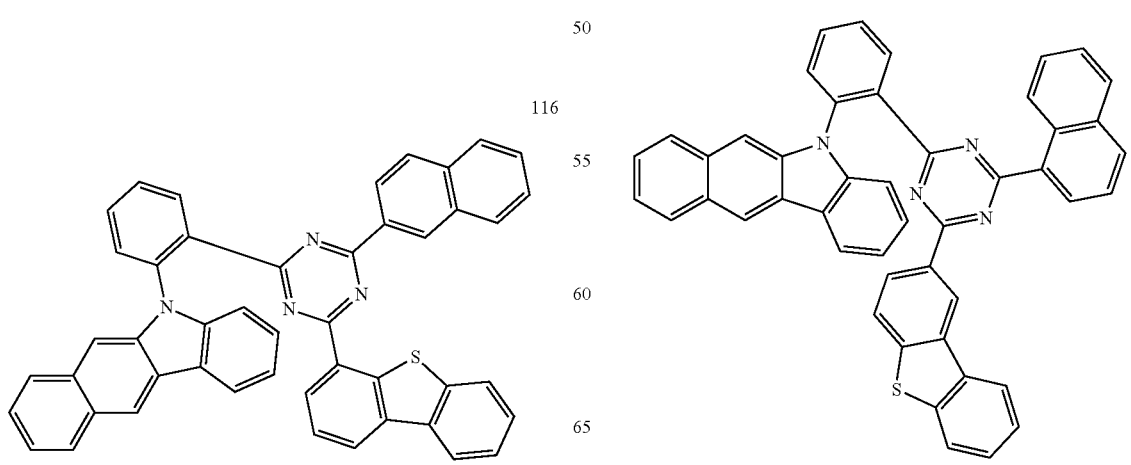

-continued

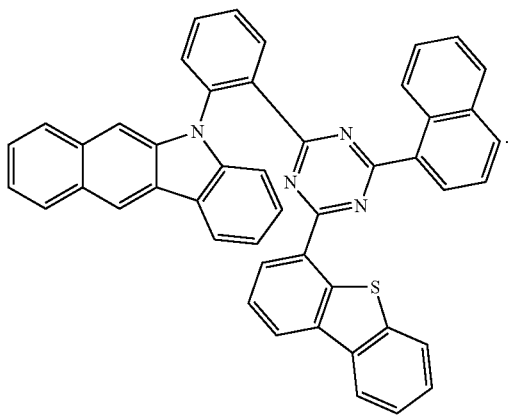

5. An organic light emitting device, comprising:
a first electrode;
a second electrode provided to face the first electrode; and
an organic material layer having one or more layers provided between the first electrode and the second electrode,
wherein one or more layers of the organic material layer comprise the compound of Formula 1 according to claim 1.

6. The organic light emitting device of claim 5, wherein the organic material layer comprises a hole injection layer or a hole transport layer, and
the hole injection layer or the hole transport layer comprises the compound of Formula 1.

7. The organic light emitting device of claim 5, wherein the organic material layer comprises a light emitting layer, and
the light emitting layer comprises the compound of Formula 1.

8. The organic light emitting device of claim 5, wherein the organic material layer comprises an electron transport layer or an electron injection layer, and
the electron transport layer or the electron injection layer comprises the compound of Formula 1.

9. The organic light emitting device of claim 5, wherein the organic light emitting device further comprises one or two or more layers selected from the group consisting of a hole injection layer, a hole transport layer, an electron transport layer, an electron injection layer, an electron blocking layer, and a hole blocking layer.

10. An organic light emitting device, comprising:
a first electrode;
a second electrode provided to face the first electrode; and
an organic material layer having one or more layers provided between the first electrode and the second electrode,
wherein one or more layers of the organic material layer comprise the compound of Formula 1 according to claim 2.

11. An organic light emitting device, comprising:
a first electrode;
a second electrode provided to face the first electrode; and
an organic material layer having one or more layers provided between the first electrode and the second electrode,
wherein one or more layers of the organic material layer comprise the compound of Formula 1 according to claim 3.

12. An organic light emitting device, comprising:
a first electrode;
a second electrode provided to face the first electrode; and
an organic material layer having one or more layers provided between the first electrode and the second electrode,
wherein one or more layers of the organic material layer comprise the compound of Formula 1 according to claim 4.

* * * * *